United States Patent
Skardal et al.

(10) Patent No.: US 12,038,432 B2
(45) Date of Patent: Jul. 16, 2024

(54) ORGANOIDS RELATED TO IMMUNOTHERAPY AND METHODS OF PREPARING AND USING THE SAME

(71) Applicant: Wake Forest University Health Sciences, Winston-Salem, NC (US)

(72) Inventors: Aleksander Skardal, Dublin, OH (US); Konstantinos Votanopoulos, Winston-Salem, NC (US)

(73) Assignee: WAKE FOREST UNIVERSITY HEALTH SCIENCES, Winston-Salem, NC (US)

(*) Notice: Subject to any disclaimer, the term of this patent is extended or adjusted under 35 U.S.C. 154(b) by 977 days.

(21) Appl. No.: 16/966,406

(22) PCT Filed: Feb. 1, 2019

(86) PCT No.: PCT/US2019/016236
§ 371 (c)(1),
(2) Date: Jul. 30, 2020

(87) PCT Pub. No.: WO2019/152767
PCT Pub. Date: Aug. 8, 2019

(65) Prior Publication Data
US 2020/0363402 A1    Nov. 19, 2020

Related U.S. Application Data

(60) Provisional application No. 62/625,628, filed on Feb. 2, 2018.

(51) Int. Cl.
| | |
|---|---|
| G01N 33/50 | (2006.01) |
| A61K 35/17 | (2015.01) |
| A61P 35/00 | (2006.01) |
| C12N 5/071 | (2010.01) |
| C12N 5/078 | (2010.01) |
| C12N 5/09 | (2010.01) |

(52) U.S. Cl.
CPC ......... *G01N 33/5082* (2013.01); *A61K 35/17* (2013.01); *A61P 35/00* (2018.01); *C12N 5/0634* (2013.01); *C12N 5/0693* (2013.01); *C12N 5/0697* (2013.01); *G01N 33/5011* (2013.01)

(58) Field of Classification Search
None
See application file for complete search history.

(56) References Cited

U.S. PATENT DOCUMENTS

| | | | |
|---|---|---|---|
| 4,734,372 A | 3/1988 | Rotman | |
| 7,449,306 B2 | 11/2008 | Elson et al. | |
| 8,298,824 B2 | 10/2012 | Warren et al. | |
| 8,748,180 B2 | 6/2014 | Shuler et al. | |
| 9,506,024 B2 | 11/2016 | Marx et al. | |
| 2002/0168415 A1 | 11/2002 | Asina et al. | |
| 2004/0136971 A1 | 7/2004 | Scharp et al. | |
| 2006/0141620 A1 | 6/2006 | Brown et al. | |
| 2007/0275363 A1 | 11/2007 | Bertram et al. | |
| 2008/0044900 A1 | 2/2008 | Mooney et al. | |
| 2009/0076584 A1 | 3/2009 | Mao et al. | |
| 2010/0000304 A1 | 1/2010 | Kim et al. | |
| 2010/0159590 A1 | 6/2010 | Alley et al. | |
| 2011/0086382 A1 | 4/2011 | Marx | |
| 2011/0172611 A1 | 7/2011 | Yoo et al. | |
| 2011/0287470 A1 | 11/2011 | Stoppini | |
| 2012/0089238 A1 | 4/2012 | Kang et al. | |
| 2013/0295598 A1 | 11/2013 | Marx et al. | |
| 2014/0178988 A1 | 6/2014 | West et al. | |
| 2014/0342394 A1 | 11/2014 | Parker et al. | |
| 2015/0076584 A1 | 3/2015 | Pachamuthu et al. | |
| 2015/0079584 A1 | 3/2015 | Gevaert et al. | |
| 2015/0132847 A1 | 5/2015 | Lipke et al. | |
| 2015/0282885 A1 | 10/2015 | King et al. | |
| 2015/0377861 A1 | 12/2015 | Pant et al. | |
| 2017/0107483 A1 | 4/2017 | Pendergraft et al. | |
| 2017/0285003 A1 | 10/2017 | Hamilton et al. | |
| 2017/0307598 A1 | 10/2017 | Skardal et al. | |
| 2018/0000743 A1 | 1/2018 | Welker et al. | |
| 2018/0119107 A1* | 5/2018 | Neal | C12N 5/0693 |
| 2018/0273904 A1 | 9/2018 | Skardal | |
| 2018/0291350 A1 | 10/2018 | Murphy et al. | |
| 2018/0320141 A1 | 11/2018 | Atala et al. | |
| 2019/0106673 A1 | 4/2019 | Skardal | |
| 2019/0187129 A1 | 6/2019 | Skardal et al. | |
| 2019/0345096 A1 | 11/2019 | Welker et al. | |

(Continued)

FOREIGN PATENT DOCUMENTS

| | | |
|---|---|---|
| DE | 69927685 T2 | 2/2006 |
| EP | 2712918 A1 | 4/2014 |

(Continued)

OTHER PUBLICATIONS

Purwada, A., Singh, A. Immuno-engineered organoids for regulating the kinetics of B-cell development and antibody production. Nat Protoc 12, 168-182 (2017). E-pub date: Dec. 22, 2016. https://doi.org/10.1038/nprot.2016.157 (Year: 2016).*

Janeway CA Jr, Travers P, Walport M, et al. Immunobiology: The Immune System in Health and Disease.5th edition. New York: Garland Science; 2001. (Year: 2001).*

Vinogradov S, Warren G, Wei X. Macrophages associated with tumors as potential targets and therapeutic intermediates. Nanomedicine (Lond). Apr. 2014;9(5):695-707. doi: 10.2217/nnm.14.13. PMID: 24827844; Pmcid: PMC4149280. (Year: 2014).*

(Continued)

*Primary Examiner* — Allison M Fox
*Assistant Examiner* — Alyssa G Weston
(74) *Attorney, Agent, or Firm* — Myers Bigel, P.A.

(57) ABSTRACT

Described herein are organoids that include at least one type of immune cell along with systems and devices including the same. Methods of preparing and using such organoids, devices and systems are also described herein.

20 Claims, 18 Drawing Sheets

(56) References Cited

U.S. PATENT DOCUMENTS

| | | |
|---|---|---|
| 2019/0345439 A1 | 11/2019 | Skardal et al. |
| 2019/0375860 A1 | 12/2019 | Welker et al. |
| 2020/0048601 A1 | 2/2020 | Skardal et al. |
| 2020/0108172 A1 | 4/2020 | Skardal et al. |
| 2020/0376489 A1 | 12/2020 | Porada et al. |
| 2022/0064597 A1 | 3/2022 | Hidalgo et al. |

FOREIGN PATENT DOCUMENTS

| | | |
|---|---|---|
| JP | 2005104987 A | 4/2005 |
| JP | 2005343899 A | 12/2005 |
| JP | 2006503080 A | 1/2006 |
| JP | 2007515949 A | 6/2007 |
| JP | 2007244250 A | 9/2007 |
| JP | 2008054521 A | 3/2008 |
| JP | 2011528653 A | 11/2011 |
| JP | 2011530280 A | 12/2011 |
| JP | 2013519360 A | 5/2013 |
| JP | 2013532484 A | 8/2013 |
| JP | 2014033626 A | 2/2014 |
| JP | 2015510391 A | 4/2015 |
| JP | 2015167521 A | 9/2015 |
| JP | 2015535688 A | 12/2015 |
| WO | 9736495 A1 | 10/1997 |
| WO | 0059173 A1 | 10/2000 |
| WO | 2005050200 A2 | 6/2005 |
| WO | 2009007531 A2 | 1/2009 |
| WO | 2009146911 A2 | 12/2009 |
| WO | 2010016023 A1 | 2/2010 |
| WO | 2011088213 A1 | 7/2011 |
| WO | 2011098402 A1 | 8/2011 |
| WO | 2012016711 A1 | 2/2012 |
| WO | 2013040559 A1 | 3/2013 |
| WO | 2013086486 A1 | 6/2013 |
| WO | 2013086502 A1 | 6/2013 |
| WO | 2013096741 A2 | 6/2013 |
| WO | 2014040026 A2 | 3/2014 |
| WO | 2014048637 A1 | 4/2014 |
| WO | 2015112624 A1 | 7/2015 |
| WO | 2015152954 A1 | 10/2015 |
| WO | 2015181185 A1 | 12/2015 |
| WO | 2016049363 A1 | 3/2016 |
| WO | 2016064648 A1 | 4/2016 |
| WO | 2016081554 | 5/2016 |
| WO | 2016100227 A1 | 6/2016 |
| WO | 2017059171 A1 | 4/2017 |
| WO | 2017059173 | 4/2017 |
| WO | 2017178572 | 10/2017 |
| WO | 2017205511 | 11/2017 |
| WO | 2018013589 | 1/2018 |
| WO | 2018027023 A1 | 2/2018 |
| WO | 2018071354 A1 | 4/2018 |
| WO | 2018071797 A1 | 4/2018 |
| WO | 2018081425 A1 | 5/2018 |
| WO | 2019028131 A1 | 2/2019 |
| WO | 2019152767 A1 | 8/2019 |

OTHER PUBLICATIONS

Caliari SR, Burdick JA. A practical guide to hydrogels for cell culture. Nat Methods. Apr. 28, 2016;13(5):405-14. doi: 10.1038/nmeth.3839. PMID: 27123816; PMCID: PMC5800304. (Year: 2016).*

Nyga et al. "The next level of 3D tumour models: immunocompetence" Drug Discovery Today, 21(9):1421-1428 (2016).

International Search Report and the Written Opinion of the International Searching Authority corresponding to International Patent Application No. PCT/US2019/016236 (12 pages) (mailed Apr. 15, 2019).

Amirabadi et al. "Cancer metastasis-on-a-chip" Poster session presented at conference; 18th annual poster contest; Technische Universiteit Eindhoven University of Technology (2 pages) (2013).

Bingle et al. "Macrophages promote angiogenesis in human breast tumour spheroids in vivo" British Journal of Cancer, 94(1):101-107 (2006).

Devarasetty et al. "A Metastasis-on-a-Chip System for Modeling Colon Carcinoma Migration and Invasion In Vitro" Tissue Engineering: Part A, 20(Supplement 1):S-15 Oral Abstract O-182 (2 pages) (2014 TERMIS-AM Conference).

Katt et al. "In Vitro Tumor Models: Advantages, Disadvantages, variables, and Selecting the Right Platform" Frontiers in Bioengineering and Biotechnology, 4(12):1-14 (2016).

Skardal et al. "A Reductionist Metastasis-on-a-Chip Platform for In Vitro Tumor Progression Modeling and Drug Screening" Biotechnology and Bioengineering, 113(9):2020-2032 (2016).

Skardal et al. "Liver-Tumor Hybrid Organoids for Modeling Tumor Growth and Drug Response In Vitro" Annals of Biomedical Engineering, 43(10):2361-2373 (2015).

Tsang et al. "Three-dimensional tissue fabrication" Advanced Drug Delivery Reviews 56:1635-1647 (2004).

Carey et al. "Leading malignant cells initiate collective epithelial cell invasion in a three-dimensional heterotypic tumor spheroid model" Clinical & Experimental Metastasis, 30:615-630 (2013).

Esch et al. "Body-on-a-chip simulation with gastrointestinal tract and liver tissues suggests that ingested nanoparticles have the potential to cause liver injury" Lab on a Chip, 14:3081-3092 (2014).

Hoffmann et al. "Impact of the spheroid model complexity on drug response" Journal of Biotechnology, 205:14-23 (2015).

Ma et al. "Towards personalized medicine with a three-dimensional micro-scale perfusion-based two-chamber tissue model system" Biomaterials, 33:4353-4361 (2012).

Tang et al. "Microfluidic device with integrated microfilter of conical-shaped holes for high efficiency and high purity capture of circulating tumor cells" Scientific Reports, 4(6052):1-7 (2014).

El-Sherbiny et al. "Hydrogel scaffolds for tissue engineering: Progress and challenges" Global Cardiology Science & Practice, 2013(3):317-342 (2013).

"Avorn, Jerry "Two Centuries of Assessing Drug Risks" The New England Journal of Medicine, 367(3):193-197 (2012)".

"Behrens, J. "Control of beta-catenin signaling in tumor development" Annals of the New York Academy of Sciences, 910:21-33; discussion pp. 33-25 (2000)".

"Foty, Ramsey "A Simple Hanging Drop Cell Culture Protocol for Generation of 3D Spheroids" Journal of Visualized Experiments 51:1-4 (2011)".

"Insphero AG "3D InSightTM Human Liver Microtissues" Brochure (2 pages) (2012)".

"Malkki, Hemi "Trial Watch: Glioblastoma vaccine therapy disappointment in Phase III trial" Nature Reviews Neurology, 12(4):190 (2016)".

"NDTV "3D Liver Cell Replicas to Fast-Track Personalised Medicine" www.ndtv.com/health (1 page) (Sep. 14, 2015)".

"phys.org "Replicating liver cells for fast drug testing" https://phys.org/news/2015-09-replicating-liver-cells-fast-drug.html (2 pages) (Sep. 10, 2015)".

"Prestwich, Glenn D. "Evaluating Drug Efficacy and Toxicology in Three Dimensions: Using Synthetic Extracellular Matrices in Drug Discovery" Accounts of Chemical Research, 41(1):139-148 (2008)".

"Prestwich, Glenn D. "Hyaluronic Acid-Based Clinical Biomaterials Derived for Cell and Molecule Delivery in Regenerative Medicine" Journal of Controlled Release, 155:193-199 (2011)".

"Prestwich, Glenn D. "Simplifying the extracellular matrix for 3-D cell culture and tissue engineering: A pragmatic approach" Journal of Cellular Biochemistry, 101(6):1370-1383 (2007)".

"Sigma-Aldrich "HyStem™—HP Cell Culture Scaffold Kit for 2.5 ml of hydrogel scaffold" Technical Bulletin (3 pages) (2014)".

"Vigneron, Nathalie "Human Tumor Antigens and Cancer Immunotherapy" BioMed Research International, 2015 (948501):1-17 (2015)".

"Wake Forest Institute for Regenerative Medicine "Researchers Develop First Ever Model for Patient-Specific Treatment of Appendix Cancer" Research News (4 pages) (Jan. 10, 2019)".

Aleman, et al., ""A multi-site metastasis-on-a-chip microphysiological system for assessing metastatic preference of cancer cells" Biotechnology and Bioengineering, 116(4):936-944 (2019)".

Allison, et al., ""Review. Hyaluronan: a powerful tissue engineering tool" Tissue Engineering, 12(8):2131-2140 (2006)".

(56) References Cited

OTHER PUBLICATIONS

Ambrosino, et al., ""Isolated Hepatocytes Versus Hepatocyte Spheroids: In Vitro Culture of Rat Hepatocytes" Cell Transplantation, 14:397-401 (2005)".
Asthana, et al., ""Microtissue size and hypoxia in HTS with 3D cultures" Drug Discovery Today, 17(15/16):810-817 (2012)".
Atala, et al., ""Tissue-engineered autologous bladders for patients needing cystoplasty" The Lancet, 367(9518):1241-1246 (2006)".
Bando, et al., ""Recent innovations in the USA National Cancer Institute-sponsored investigator initiated Phase I and II anticancer drug development" Japanese Journal of Clinical Oncology, 45(11):1001-1006 (2015)".
Baptista, Pedro, et al., "The use of whole organ decellularization for the generation of a vascularized liver organoid", Hepatology, 53(2), 2011, 604-617.
Batchelder, et al., ""Three Dimensional Culture of Human Renal Cell Carcinoma Organoids" PLoS One, 10(8): e0136758 (2015)".
Benam, et al., ""Engineered In Vitro Disease Models" Annual Review of Pathology: Mechanisms of Disease, 10:195-262 (2015)".
Bentrup, et al., ""Three-dimensional organotypic models of human colonic epithelium to study the early stages of enteric salmonellosis" Microbes and Infection, 8:1813-1825 (2006)".
Bersini, et al., ""A Microfluidic 3D In Vitro Model for Specificity of Breast Cancer Metastasis to Bone" Biomaterials, 35(8):2454-2461 (2014)".
Bersini, et al., ""In vitro models of the metastatic cascade: from local invasion to extravasation" Drug Discovery Today, 19(6):735-742 (2014)".
Bhattacharya, et al., ""Toxicity Testing in the 21st Century: Defining New Risk Assessment Approaches Based on Perturbation of Intracellular Toxicity Pathways" PloS One, 6(6):e20887 (2011)".
Bhise, Nupura S., et al., "A liver-on-a-chip platform with bioprinted hepatic spheroids", Biofabrication, 8(1), 2016, 014101.
Bhise, Nupura S., et al., "Organ-on-a-chip platforms for studying drug delivery systems", Journal of Controlled Release, 190, 2014, 82-93.
Bhushan, et al., ""Towards a three-dimensional microfluidic liver platform for predicting drug efficacy and toxicity in humans" Stem Cell Research & Therapy, 4(Suppl 1):S16 (pp. 1-6) (2013)".
Blackwood, et al., ""Disaccharide, Oligosaccharide and Polysaccharide Analysis" Carbohydrate Analysis (pp. 1-24) (2006)".
Brantjes, et al., ""TCF: Lady Justice Casting the Final Verdict on the Outcome of Wnt Signalling" Biological Chemistry, 383(2):255-261 (2002)".
Burdick, et al., ""Hyaluronic Acid Hydrogels for Biomedical Applications" Advanced Materials, 23(12):H41-H56 (2011)".
Cantrell, et al., ""Organoid modeling for cancer precision medicine" Genome Medicine, 7(32):1-3 (2015)".
Cirkel, et al., ""Tumor heterogeneity and personalized cancer medicine: are we being outnumbered?" Future Oncology, 10(3):417-428 (2014)".
Clevers, Hans, et al., "Q&A: Hans Clevers. Banking on organoids", Nature, 521(7551), 2015, S15.
Cosson, Steffen, et al., "Ultra-rapid prototyping of flexible, multi-layered microfluidic devices via razor writing", Lab on a Chip, 15(1), 2015, 72-76.
Dedhia, et al., ""Organoid Models of Human Gastrointestinal Development and Disease" Gastroenterology, 150:1098-1112 (2016)".
Deegan, et al., ""Stiffness of hyaluronic acid gels containing liver extracellular matrix supports human hepatocyte function and alters cell morphology" Journal of the Mechanical Behavior of Biomedical Materials, 55:87-103 (2015)".
Devarasetty, et al., ""Modeling the Colon-Tumor Microenvironment Using Multicellular Hydrogel Strata" Tissue Engineering: Part A, 20(Supplement 1):S-77 Poster Abstract P-241 (2 pages) (2014 TERMIS-AM Conference, Washington, DC, Dec. 13-16, 2014)".
Drewitz, et al., ""Towards automated production and drug sensitivity testing using scaffold-free spherical tumor microtissues" Biotechnology Journal, 6(12):1488-1496 (2011)".
Dwyer, et al., ""Thrombin based gelatin matrix and fibrin sealant mediated clot formation in the presence of clopidogrel" Thrombosis Journal, 12(10):1-13 (2014)".
Edmondson, Rasheena, et al., "Three-dimensional cell culture systems and their applications in drug discovery and cell-based biosensors", Assay and Drug Development Technologies, 12(4), 2014, 207-218.
Esch, et al., ""How Multi-Organ Microdevices Can Help Foster Drug Development" Advanced Drug Delivery Reviews, 69-70:158-169 (2014)".
Fidler, et al., ""The role of the organ microenvironment in the biology and therapy of cancer metastasis" Journal of Cellular Biochemistry, 101:927-936 (2007)".
Figallo, et al., ""Micro-bioreactor array for controlling cellular microenvironments" Lab on a Chip, 6:710-719 (2007)".
Forsythe, et al., ""Development of a Colorectal Cancer 3D Microtumor Construct Platform From Cell Lines and Patient Tumor Biospecimens for Standard-of-Care and Experimental Drug Screening" Annals of Biomedical Engineering (13 pages) (2019)".
Franci, et al., ""Biomarkers of Residual Disease, Disseminated Tumor Cells, and Metastases in the MMTV-PyMT Breast Cancer Model" PLoS One, 8:e58183 (2013)".
Francies, et al., ""What role could organoids play in the personalization of cancer treatment?" Pharmacogenomics, 16(14):1523-1526 (2015)".
Fu, et al., ""A microfluidic chip with a U-shaped microstructure array for multicellular spheroid formation, culturing and analysis" Biofabrication, 6:1-9 (2014)".
Gao, et al., ""Organoid Cultures Derived from Patients with Advanced Prostate Cancer" Cell, 159:176-187 (2014)".
Gavert, et al., ""Coordinating changes in cell adhesion and phenotype during EMT-like processes in cancer" F1000 Reports Biology, 2(86):1-4 (2010)".
Ghaemmaghami, et al., ""Biomimetic tissues on a chip for drug discovery" Drug Discovery Today, 17(3-4):173-181 (2012)".
Hall, et al., ""Characteristics of FDA drug recalls: A 30-month analysis" American Journal of Health-System Pharmacy, 73(4):235-240 (2016)".
Han, et al., ""Microfluidic Chips for Immunoassays" Annual Review of Analytical Chemistry, 6:119-141 (2013)".
Hasan, et al., ""Injectable Hydrogels for Cardiac Tissue Repair after Myocardial Infarction" Advanced Science 2(11):1500122 (2015)".
Hayes, et al., ""Personalized Medicine: Genomics Trials in Oncology" Transactions of the American Clinical and Climatological Association, 126:133-143 (2015)".
Hidalgo, et al., ""Patient Derived Xenograft Models: An Emerging Platform for Translational Cancer Research" Cancer Discovery, 4(9):998-1013 (2014)".
Ho, et al., ""Incorporation of multicellular spheroids into 3-D polymeric scaffolds provides an improved tumor model for screening anticancer drugs" Cancer Science, 101:2637-2643 (2010)".
Huang, et al., ""Ductal pancreatic cancer modeling and drug screening using human pluripotent stem cell- and patient-derived tumor organoids" Nature Medicine, 21:1364-1371 (2015)".
Huh, et al., ""From 3D cell culture to organs-on-chips" Trends in Cell Biology, 21(12):745-754 (2011)".
Huh, et al., ""Microfabrication of human organs-on-chips" Nature Protocols, 8(11):2135-2157 (2013)".
Ikpa, et al., ""Cystic fibrosis: toward personalized therapies" The International Journal of Biochemistry & Cell Biology, 52:192-200 (2014)".
Jain, et al., ""Primary Human Lung Alveolus-on-a-chip Model of Intravascular Thrombosis for Assessment of Therapeutics" Clinical Pharmacology & Therapeutics, 103(2):332-340 (2018)".
Jamieson, et al., ""Chemical analysis of multicellular tumour spheroids" The Analyst, 140:3910-3920 (2015)".
Johnson, et al., ""Rapid Microfluidic Mixing" Analytical Chemistry, 74(1):45-51 (2002)".
Jouin, et al., ""Cryopreserved human hepatocytes in suspension are a convenient high throughput tool for the prediction of metabolic clearance" European Journal of Pharmaceutics and Biopharmaceutics, 63(3):347-355 (2006)".

(56) References Cited

OTHER PUBLICATIONS

Kaneko, et al., ""An on-chip cardiomyocyte cell network assay for stable drug screening regarding community effect of cell network size" The Analyst, 132(9):892-898 (2007)".

Kang, Hyun-Wook, et al., "A 3D bioprinting system to produce human-scale tissue constructs with structural integrity", Nature Biotechnology, 34(3), 2016, 312-319.

Karakiulakis, et al., ""Increased type IV collagen-degrading activity in metastases originating from primary tumors of the human colon" Invasion & Metastasis, 17(3):158-168 (1997)".

Kelm, et al., ""Design of Artificial Myocardial Microtissues" Tissue Engineering, 10(1-2):201-214 (2004)".

Kim, et al., ""A cell-based biosensor for real-time detection of cardiotoxicity using lensfree imaging" Lab Chip, 11(10):1801-1807 (2011)".

Kim, et al., ""A mini-microscope for in situ monitoring of cells" Lab Chip, 12(20):3976-3982 (2012)".

Kim, et al., ""A Quantitative Microfluidic Angiogenesis Screen for Studying Anti-Angiogenic Therapeutic Assay" Lab on a Chip, 15(1):301-310 (2015)".

Klinghoffer, et al., ""A technology platform to assess multiple cancer agents simultaneously within a patient's tumor" Science Translational Medicine, 7(284):284ra58 (2015)".

Kunz-Schughart, et al., ""The Use of 3-D Cultures for High-Throughput Screening: The Multicellular Spheroid Model" Journal of Biomolecular Screening, 9(4):273-285 (2004)".

Lang, Ren, et al., "Three-dimensional culture of hepatocytes on porcine liver tissue-derived extracellular matrix", Biomaterials, 32(29) (Abstract Only), 2011, 7042-7052.

Langley, et al., ""Tumor Cell-Organ Microenvironment Interactions in the Pathogenesis of Cancer Metastasis" Endocrine Reviews, 28:297-321 (2007)".

Leventhal, et al., ""Matrix Crosslinking Forces Tumor Progression by Enhancing Integrin signaling" Cell, 139:891-906 (2009)".

Li, et al., ""Microfluidic 3D cell culture: potential application for tissue-based bioassays" Bioanalysis, 4(12):1509-1525 (2012)".

Li, et al., ""Zebrafish on a Chip: A Novel Platform for Real-Time Monitoring of Drug-Induced Developmental Toxicity" PLoS One, 9(4):e94792 (2014)".

Lin, et al., ""The application of engineered liver tissues for novel drug discovery" Expert Opinion on Drug Discovery, 10:519-540 (2015)".

Malda, et al., ""25th Anniversary Article: Engineering Hydrogels for Biofabrication" Advanced Materials 25:5011-5028 (2013)".

Maschmeyer, et al., ""A four-organ-chip for interconnected long-term co-culture of human intestine, liver, skin and kidney equivalents" Lap on a Chip, 15:2688-2699 (2015)".

McGrail, et al., ""SNAIL-induced epithelial-to-mesenchymal transition produces concerted biophysical changes from altered cytoskeletal gene expression" The FASEB Journal, 29:1280-1289 (2015)".

Messner, S., et al., "Multi-cell type human liver microtissues for hepatotoxicity testing", Archives of Toxicology, 87(1), 2013, 209-213.

Miles, et al., ""Genetic Testing and Tissue Banking for Personalized Oncology: Analytical and Institutional Factors" Seminars in Oncology, 42(5):713-723 (2015)".

Miranda, et al., ""Towards Multi-Organoid Systems for Drug Screening Applications" Bioengineering, 5(49):1-17 (2018)".

Mironov, et al., ""Bioprinting: A Beginning" Tissue Engineering 12(4):631-634 (2006)".

Mou, et al., ""Personalized Medicine for Cystic Fibrosis: Establishing Human Model Systems" Pediatric Pulmonology, 50:S14-S23 (2015)".

Muprhy, et al., ""3D bioprinting of tissues and organs" Nature Biotechnology, 32(8):773-785 (2014)".

Murphy, et al., ""Evaluation of hydrogels for bio-printing applications" Journal of Biomedical Materials Research A 101A(1):272-284 (2013)".

Murphy, et al., ""Evaluation of hydrogels for bio-printing applications" Journal of Biomedical Materials Research Part A, 101(1):272-284 (2013)".

Nantasanti, et al., ""Concise Review: Organoids are a Powerful Tool for the Study of Liver Disease and Personalized Treatment Design in Humans and Animals" Stem Cells Translational Medicine, 5:325-330 (2016)".

Navarrete, et al., ""Screening Adverse Drug-Induced Arrhythmia Events Using Human Induced Pluripotent Stem Cell-Derived Cardiomyocytes and Low-Impedance Microelectrode Arrays" Circulation 128(1101):1-23 (2013)".

Ng, et al., ""Components for integrated poly(dimethylsiloxane) microfluidic systems" Electrophoresis, 23:3461-3473 (2002)".

Nickerson, et al., ""Microgravity as a Novel Environmental Signal Affecting *Salmonella enterica* Serovar Typhimurium Virulence" Infection and Immunity, 68(6):3147-3152 (2000)".

Nickerson, et al., ""Studying Host-Pathogen Interactions in 3-D: Organotypic Models for Infectious Disease and Drug Development" Journal of Neuroimmune Pharmacology, 2(1):26-31 (2007)".

Nickerson, et al., ""Three-Dimensional Tissue Assemblies: Novel Models for the Study of Salmonella enterica Serovar Typhimurium Pathogenesis" Infection and Immunity, 69(11):7106-7120 (2001)".

Niu, et al., ""Validating anti-metastatic effects of natural products in an engineered microfluidic platform mimicking tumor microenvironment" Molecular Pharmaceutics, 11(7):2022-2029 (2014)".

Norotte, et al., ""Scaffold-Free Vascular Tissue Engineering Using Bioprinting" Biomaterials 30(30):5910-5917 (2009)".

O'Brien, et al., ""Three-Dimensional Printing of Nanomaterial Scaffolds for Complex Tissue Regeneration" Tissue Engineering: Part B 21(1):103-114 (2014)".

Oleaga, et al., ""Multi-Organ toxicity demonstration in a functional human in vitro system composed of four organs" Scientific Reports, 6(20030):1-17 (2016)".

Orsulic, et al., ""E-cadherin binding prevents b-catenin nuclear localization and beta-catenin/LEF-1-mediated transactivation" Journal of Cell Science, 112:1237-1245 (1999)".

Orsulic, et al., ""E-cadherin binding prevents beta-catenin nuclear localization and beta-catenin/LEF-1-mediated transactivation" Journal of Cell Science, 112:1237-1245 (1999)".

Papkovsky, et al., ""Biological detection by optical oxygen sensing" Chemical Society Reviews, 42(22):8700-8732 (2013)".

Pasirayi, et al., ""Low cost microfluidic cell culture array using normally closed valves for cytotoxicity assay" Talanta, 129:491-498 (2014)".

Peters, et al., ""Evaluation of cellular impedance measures of cardiomyocyte cultures for drug screening applications" Assay and Drug Development Technologies, 10:525-532 (2012)".

Polacheck, et al., ""Mechanotransduction of fluid stresses governs 3D cell migration" Proceedings of the National Academy of Sciences USA, 111(7):2447-2452 (2014)".

Polini, et al., ""Organs-on-a-chip: a new tool for drug discovery" Expert Opinion on Drug Discovery, 9(4):335-352 (2014)".

Prestwich, et al., ""Chemically-modified HA for therapy and regenerative medicine" Current Pharmaceutical Biotechnology, 9(4):242-245 (2008)".

Qin, et al., ""Soft lithography for micro- and nanoscale patterning" Nature Protocols, 5(3):491-502 (2010)".

Qu, et al., ""Proarrhythmia Risk Assessment in Human Induced Pluripotent Stem Cell-Derived Cardiomyocytes Using the Maestro MEA Platform" Toxicological Sciences 147(1):1-10 (2015)".

Raya-Rivera, et al., ""Tissue-engineered autologous urethras for patients who need reconstruction: an observational study" The Lancet, 377(9772):1175-1182 (2011)".

Raya-Rivera, et al., ""Tissue-engineered autologous vaginal organs in patients: a pilot cohort study" The Lancet, 384(9940):329-336 (2014)".

Reimers, et al., ""Biomarkers in precision therapy in colorectal cancer" Gastroenterology Report, 1(3):166-183 (2013)".

Ronaldson-Bouchard, et al., ""Organs-on-a-Chip: A Fast Track for Engineered Human Tissues in Drug Development" Cell Stem Cell, 22(3):310-324 (2018)".

(56) References Cited

OTHER PUBLICATIONS

Rosfjord, et al., ""Advances in patient-derived tumor xenografts: from target identification to predicting clinical response rates in oncology" Biochemical Pharmacology, 91:135-143 (2014)".
Sachs, et al., ""Organoid cultures for the analysis of cancer phenotypes" Current Opinion in Genetics & Development, 24:68-73 (2014)".
Schussler, et al., ""Collagen Scaffold Modified by Covalent Grafting of Adhesion Molecules, Associated Methods and Use Thereof for Cardiovascular and Thoracic Cell Therapy and Contractile Tissue Engineering" English Machine Translation of International Patent Application Pub".
Schwarz, et al., ""Value of Organoids from Comparative Epithelia Models" Yale Journal of Biology and Medicine, 88:367-374 (2015)".
Seruga, et al., ""Failures in Phase III: Causes and Consequences" Clinical Cancer Research, 21(20):4552-4560 (2015)".
Sharma, et al., ""The future of immune checkpoint therapy" Science, 348(6230):56-61 (2015)".
Shin, et al., ""Microfluidic assay for simultaneous culture of multiple cell types on surfaces or within hydrogels" Nature Protocols, 7(7):1247-1259 (2014)".
Shu, et al., ""In situ crosslinkable hyaluronan hydrogels for tissue engineering" Biomaterials, 25(7-8):1339-1348 (2004)".
Skardal, Aleksander, et al., "A hydrogel bioink toolkit for mimicking native tissue biochemical and mechanical properties in bioprinted tissue constructs", Acta Biomaterialia, 25, 2015, 24-34.
Skardal, Aleksander, et al., "A tunable hydrogel system for long-term release of cell-secreted cytokines and bioprinted in situ wound cell delivery", Journal of Biomedical Materials Research Part B: Applied Biomaterials, 105(7), 2017, 1986-2000.
Skardal, Aleksander, et al., "An In Vitro 3-D Liver-Tumor Hybrid Organoid System for Modeling Metastasis and Drug Resistance", Tissue Engineering: Part A, 20(Suppl 1). 2014 TERMIS-AM Conference, Washington, DC. Dec. 13-16, 2014, S-15.
Skardal, Aleksander, et al., "Biomaterials for Integration with 3-D Bioprinting", Annals of Biomedical Engineering, 43(3), 2015, 730-746.
Skardal, Aleksander, et al., "Bioprinting Cellularized Constructs Using a Tissue-specific Hydrogel Bioink", Journal of Visualized Experiments, 110(e53606), 2016, 1-8.
Skardal, Aleksander, et al., "Bioprinting vessel-like constructs using hyaluronan hydrogels crosslinked with tetrahedral polyethylene glycol tetracrylates", Biomaterials, 31(24), 2010, 6173-6181.
Skardal, Aleksander, et al., "Drug compound screening in single and integrated multi-organoid body-on-a-chip systems", Biofabrication, 12(025017), 2020, 1-18.
Skardal, Aleksander, et al., "Dynamically Crosslinked Gold Nanoparticle—Hyaluronan Hydrogels", Advanced Materials, 22(42), 2010, 4736-4740.
Skardal, Aleksander, et al., "In situ patterned micro 3D liver constructs for parallel toxicology testing in a fluidic device", Biofabrication, 7(3), 031001, 2015, (16 pages).
Skardal, Aleksander, et al., "Integration of 3-D Organoid Bioprinting and Microfluidic Device Technology for Functional Primary Cell-Based Liver-on-a-Chip Operation", Tissue Engineering: Part A, 20(Suppl 1). 2014 TERMIS-AM Conference, Washington, DC. Dec. 13-16, 2014, S43.
Skardal, Aleksander, et al., "Multi-tissue interactions in an integrated three-tissue organ-on-a-chip platform", Scientific Reports, 7(8837), 2017, 1-16.
Skardal, Aleksander, et al., "Organoid-on-a-chip and body-on-a-chip systems for drug screening and disease modeling", Drug Discovery Today, 21(9), 2016, 1399-1411.
Skardal, Aleksander, et al., "P-183: A Microfluidic Platform for Parallel Analysis of In Situ Patterned 3-D Liver Organoids", Tissue Engineering: Part A, 20(Suppl 1). 2014 TERMIS-AM Conference, Washington, DC. Dec. 13-16, 2014, S68-S69.
Skardal, Aleksander, et al., "Photocrosslinkable hyaluronan-gelatin hydrogels for two-step bioprinting", Tissue Engineering: Part A, 16(8), 2010, 2675-2685.
Skardal, Aleksander, et al., "The generation of 3-D tissue models based on hyaluronan hydrogel-coated microcarriers within a rotating wall vessel bioreactor", Biomaterials, 31(32), 2010, 8426-8435.
Skardal, Aleksander, et al., "Tissue specific synthetic ECM hydrogels for 3-D in vitro maintenance of hepatocyte function", Biomaterials, 33(18), 2012, 4565-4575.
Smith, et al., ""Microphysiological systems and low-cost microfluidic platform with analytics" Stem Cell Research & Therapy, 4(Suppl 1):S9 (pp. 1-5) (2013)".
Stock, et al., ""Targets for Anti-metastatic Drug Development" Current Pharmaceutical Design, 19:5127-5134 (2013)".
Straub, et al., ""In Vitro Cell Culture Infectivity Assay for Human Noroviruses" Emerging Infectious Diseases, 13(3):396-403 (2007)".
Sung, et al., ""A micro cell culture analog (µCCA) with 3-D hydrogel culture of multiple cell lines to assess metabolism-dependent cytotoxicity of anti-cancer drugs" Lab on a Chip, 9:1385-1394 (2009)".
Sung, et al., ""A microfluidic device for a pharmacokinetic-pharmacodynamics (PK-PD) model on a chip" Lab on a Chip, 10:446-455 (2010)".
Sung, et al., ""Using PBPK guided 'Body-on-a-Chip' Systems to Predict Mammalian Response to Drug and Chemical Exposure" Experimental Biology and Medicine, 239:1225-1239 (2014)".
Tania, et al., ""Epithelial to mesenchymal transition inducing transcription factors and metastatic cancer" Tumour biology: the Journal of the International Society for Oncodevelopmental Biology and Medicine, 35(8):7335-7342 (2014)".
Tehranirokh, et al., ""Microfluidic devices for cell cultivation and proliferation" Biomicrofluidics, 7:051502-1-051502-32 (2013)".
Temiz, Yuksel, et al., "Lab-on-a-chip devices: How to close and plug the lab?", Microelectronic Engineering, 132, 2015, 156-175.
Tostoes, et al., ""Human Liver Cell Spheroids in Extended Perfusion Bioreactor Culture for Repeated-Dose Drug Testing" Hepatology, 55:1227-1236 (2012)".
Tran, et al., ""Precision medicine in colorectal cancer: the molecular profile alters treatment strategies" Therapeutic Advances in Medical Oncology, 7(5):252-262 (2015)".
Unger, et al., ""Monolithic Microfabricated Valves and Pumps by Multilayer Soft Lithography" Science, 288:113-116 (2000)".
Van De Stolpe, et al., ""Workshop meeting report Organs-on-Chips: human disease models" Lab Chip, 13(18):3449-3470 (2013)".
Van Duinen, et al., ""Microfluidic 3D cell culture: from tools to tissue models" Current Opinion in Biotechnology, 35:118-126 (2015)".
Villenave, et al., ""Human Gut-On-A-Chip Supports Polarized Infection of Coxsackie B1 Virus In Vitro" PloS One, 12(2):e0169412 (2017)".
Votanopoulos, et al., ""Appendiceal Cancer Patient-Specific Tumor Organoid Model for Predicting Chemotherapy Efficacy Prior to Initiation of Treatment: A Feasibility Study" Annals of Surgical Oncology, 26:139-147 (2019)".
Weeber, et al., ""Preserved genetic diversity in organoids cultured from biopsies of human colorectal cancer metastases" Proceedings of the National Academy of Sciences USA, 112(43):13308-13311 (2015)".
Wikswo, et al., ""Engineering Challenges for Instrumenting and Controlling Integrated Organ-on-Chip Systems" IEEE Transactions on Biomedical Engineering, 60(3):682-690 (2013)".
Wu, et al., ""Enhanced Cytochrome P450 IA1 Activity of Self-Assembled Rat Hepatocyte Spheroids" Cell Transplantation, 8:233-246 (1999)".
Xia, et al., ""PI3K/Akt/mTOR signaling pathway in cancer stem cells: from basic research to clinical application" American Journal of Cancer Research, 5(5):1602-1609 (2015)".
Xia, et al., ""Soft Lithography" Annual Review of Materials Science, 28:153-184 (1998)".
Xu, et al., ""Hybrid printing of mechanically and biologically improved constructs for cartilage tissue engineering applications" Biofabrication, 5(015001):1-10 (2013)".
Ye, et al., ""Encapsulation of Cardiomyocytes in a Fibrin Hydrogel for Cardiac Tissue Engineering" Journal of Visualized Experiments, 55:e3251 (2011)".
Zaman, et al., ""Migration of tumor cells in 3D matrices is governed by matrix stiffness along with cell-matrix adhesion and

(56) References Cited

OTHER PUBLICATIONS proteolysis" Proceedings of the National Academy of Sciences USA, 103(29):10889-10894 (2006)".

Zhang, et al., ""A Cost-Effective Fluorescence Mini-Microscope with Adjustable Magnifications for Biomedical Applications" Lab Chip, 15(18):3661-3669 (2015)".

Zhang, et al., ""A Highly Efficient Bubble Trap for Continuous Removal of Gas Bubbles from Microfluidic Devices" Proceedings of microTAS (3 pages) (2014)".

Zhang, et al., ""Computational Systems Biology and Dose-Response Modeling in Relation to New Directions in Toxicity Testing" Journal of Toxicology and Environmental Health, Part B, 13:253-276 (2010)".

Zhang, et al., ""Engineered Extracellular Matrices with Cleavable Crosslinkers for Cell Expansion and Easy Cell Recovery" Biomaterials, 29(34):4521-4531 (2008)".

Zhang, et al., ""Personalizing pancreatic cancer organoids with hPSCs" Nature Medicine, 21:1249-1251 (2015)".

Zhang, et al., ""Towards a human-on-chip: Culturing multiple cell types on a chip with compartmentalized microenvironments" Lab on a Chip, 22:3185-3192 (2009)".

Zwi, et al., ""Cardiomyocyte Differentiation of Human Induced Pluripotent Stem Cells" Circulation, 120(15):1513-1523 (2009)".

Extended European Search Report corresponding to European Patent Application No. 19746913.3 (14 pages) (dated Apr. 1, 12, 2022).

Partial supplementary European search report corresponding to European Patent Application No. 19746913.3 (15 pages) (dated Oct. 18, 2021).

Dereli-Korkut et al. "Three dimensional microfluidic cell arrays for ex vivo drug screening with mimicked vascular flow" Analytical Chemistry, 86(6):2997-3004 (2014).

Roh-Johnson et al. "Macrophage contact induces RhoA GTPase signaling to trigger tumor cell intravasation" Oncogene, 33(33):4203-4212 (2014).

\* cited by examiner

Fig. 3A
Fig. 3B
Fig. 3C
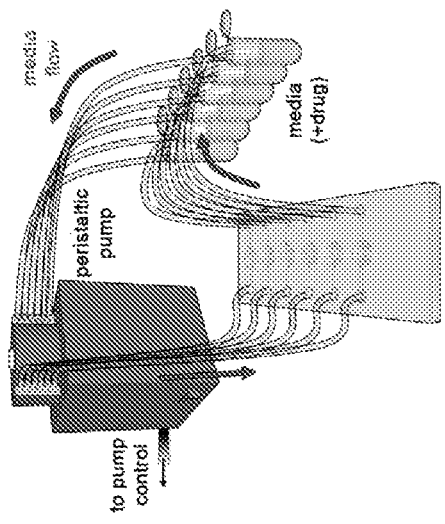
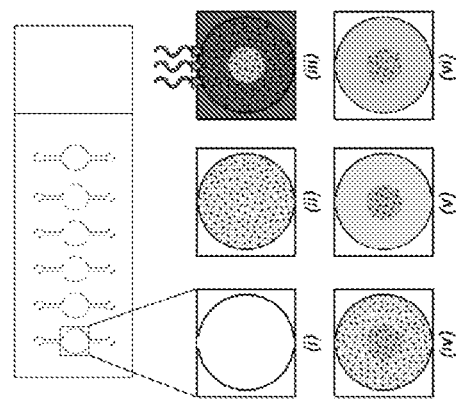
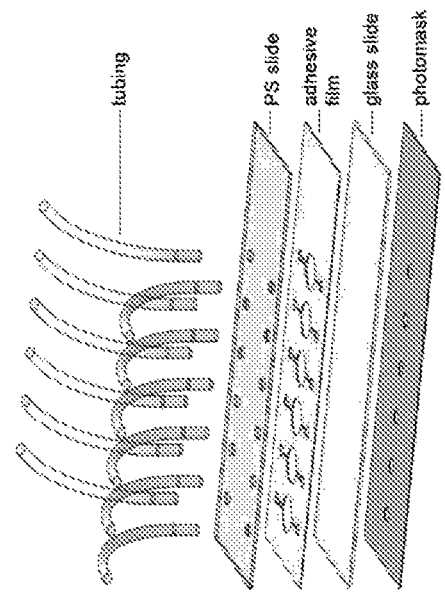

ORGANOIDS RELATED TO IMMUNOTHERAPY AND METHODS OF PREPARING AND USING THE SAME

STATEMENT OF PRIORITY

This application claims the benefit, under 35 U.S.C. § 119(e), of U.S. Provisional Application No. 62/625,628, filed on Feb. 2, 2018, the entire contents of which are incorporated by reference herein.

GOVERNMENT SUPPORT

This invention was made with government support under grant numbers 1U54TR001362-01, 5UL1TR001420-03, and 5P30CA012197-43 awarded by the National Institutes of Health. The government has certain rights in the invention.

FIELD

The present invention generally relates to organoids, including tumor organoids and organoids including immune cells, along with methods of preparing and using the same.

BACKGROUND

Immunotherapy has arisen as an attractive anti-cancer therapy due to its ability to target tumors efficiently. However, no in vitro models exist in which such therapies can be adequately tested generally or for specific patients.

Initially, animal models seemed attractive because they could provide complexity reminiscent of the in vivo tumor physiology. However, even beyond infrastructure requirements and ethical questions that accompany the use of animals, the power of these models to predict outcomes in humans is tenuous. Patient-derived tumor xenografts (PDX) technology has recently been introduced to predict how a patient's tumor will respond to drugs. Small fragments of a patient's tumor are implanted in immune-deficient mice. Once a tumor fragment has grown to adequate size, the tumor is removed, split into several pieces, and re-implanted into new mice. The main advantages of PDX technology are: 1) the patient's cancer cells are expanded in vivo recreating components of the tumor microenvironment that make significant contributions to the pathobiology of the cancer and 2) the ability to test a drug on the patient's growing tumor prior to clinical treatment of the patient. However, the PDX technology fails to grow tumors that are below a certain size, and the most successful PDXs come from very aggressive tumors, making this technology applicable to some, but not all, cancer patients. Furthermore, the tumor microenvironment (TME) for PDX is of murine origin and thus, lacking human-specific stromal elements.

Cancer research has been limited by the inability to accurately model tumor progression and signaling mechanisms in a controlled, in vitro environment. Beyond the problems with PDX models mentioned above, animal models allow only limited manipulation and study, and are not necessarily predictive of results in humans. Traditional in vitro 2D cultures fail to recapitulate the 3D in vivo microenvironment. Drug kinetics vary dramatically, doses effective in 2D are often ineffective in patients, and cell-cell/cell-matrix interactions are inaccurate. Tissue culture dishes differ from in vivo tumors with respect to topography, stiffness, and 2D versus 3D architecture. Furthermore, 2D culture can place selective pressure on cells that alters molecular and phenotypic properties.

SUMMARY

A first aspect of the present invention is directed to an in vitro cell construct (or "organoid") useful as an immune system model (e.g., useful for evaluating immunological activity and/or modulating the immune system and/or useful for screening one or more cancer therapies and/or immunotherapies), comprising a plurality of immune cells.

A further aspect of the present invention is directed to an in vitro cell construct (or "organoid") useful as a tumor model (e.g., useful for evaluating immunological activity and/or modulating the immune system and/or useful for screening one or more cancer therapies and/or immunotherapies), comprising live tumor cells and at least one type of immune cell.

Another aspect of the present invention is directed to a method of screening a compound of interest in vitro for immunological activity and/or modulating the immune system, comprising: providing at least one organoid comprising a plurality of cells (e.g., optionally wherein the at least one organoid is a liver organoid, heart organoid, tumor organoid, immune system organoid, etc.); contacting the compound of interest to the at least one organoid in vitro; and then responsive to contacting the compound of interest to the at least one organoid in vitro, determining an immunological response of the at least one organoid (e.g., as compared to the immunological response/activity of the organoid prior to and/or in the absence of contact with the compound of interest).

A further aspect of the present invention is directed to a method of screening a compound of interest in vitro for anti-tumor activity comprising: providing at least one construct comprising live tumor cells and at least one type of immune cell; contacting the compound of interest to the construct in vitro; and then responsive to contacting the compound of interest to the construct in vitro, determining the growth of the live tumor cells (e.g., as compared to tumor cells of at least one like construct not contacted with the compound of interest and/or as compared to live benign cells in the construct or at least one like construct), a decrease in growth of the live tumor cells (e.g., lack of proliferation of the tumor cells, death of the tumor cells, decrease in invasion of by the tumor cells, etc.), indicating anti-tumor activity of the compound of interest.

Another aspect of the present invention is directed to a method of screening a compound of interest in vitro for immunological activity, modulating the immune system, anti-metastatic activity, and/or anti-tumor activity, comprising: providing a device comprising an immune cell organoid and a live tumor cell organoid; contacting the immune cell organoid and the live tumor cell organoid with a growth medium; contacting a compound of interest to the immune cell organoid and/or the live tumor cell organoid (e.g., by adding the compound to the growth medium); and responsive to contacting the compound of interest to the immune cell organoid and/or the live tumor cell organoid, determining the growth of the live tumor cells (e.g., as compared to tumor cells of at least one like live tumor cell organoid not contacted with the compound of interest and/or as compared to live benign cells in the organoid or at least one like live tumor cell organoid), a decrease in growth of the live tumor cells (e.g., lack of proliferation of the tumor cells, death of the tumor cells, decrease in invasion of by the tumor cells, etc.) indicating anti-tumor activity of the compound of interest, and/or determining an immunological response of the immune cell organoid and/or the live tumor cell organoid (e.g., as compared to the immunological response/activity of the immune cell organoid and/or the live tumor cell organoid prior to and/or in the absence of contact with the compound of interest).

A further aspect of the present invention is directed to a method of activating an immune cell ex vivo, the method comprising: contacting an immune cell (e.g., a lymphocyte) to a live tumor cell organoid comprising a plurality of live tumor cells to provide an activated immune cell (e.g., through developing an adaptive immunity mechanism); isolating the activated immune cell from the live tumor cell organoid to provide an isolated activated immune cell; and propagating the isolated activated immune cell to provide a population of activated immune cells.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 1A shows colorectal tumor mitochondrial metabolism measured media alone (control), media plus pembrolizumab, and media plus nivolumab. Increased metabolism is observed only when immune cells are present with the appropriate drug (in this case nivolumab), suggesting T-cell activation. FIG. 1B shows LIVE/DEAD imaging of appendiceal tumor organoids with and without node cells. Insignificant differences were observed with no drug, but the PD-1 inhibitors nivolumab and pembrolizumab appear to be effective only when immune cell (lymph) population was incorporated. FIG. 1C shows LIVE/DEAD imaging of tumor organoids derived from a melanoma patient who was established not to respond to checkpoint inhibitor immunotherapy ("Non-Responder"). Patient tumor organoids show recapitulation of non-responder patient phenotype. Alternative treatment with dabrafenic/trametinib (right-most panel) showed response of increased DEAD staining.

FIGS. 3A-3C are schematic illustrations of a microfluidic device according to embodiments of the present invention. FIG. 3A shows schematic assembling of microfluidic device layers. FIG. 3B shows an in situ organoid patterning technique: a microfluidic chamber is filled with hydrogel mixture containing HA hydrogel, photoinitiator, and patient-derived tumor cells and then illuminated with UV light through a photomask. Exposed precursor is crosslinked into a hydrogel, detaining cells within the region, and non-crosslinked gel is flushed from the chamber with clean PBS from the chamber. Finally, PBS is replaced with DMEM for incubation. FIG. 3C shows a schematic of the total measurement set-up, featuring a low-volume, closed loop fluidic circuit for each organoid facilitated by a computer-controlled peristaltic pump.

FIG. 11A shows parallel channels of existing TOC systems are daisy chained together to increase patient tumor organoids (PTOs) number per circulator path. FIG. 11B is a schematic illustrating that many PTOs may be patterned in a single chamber of a device, which may dramatically increase PTO numbers. FIG. 11C shows an example schematic illustrating that following T cell infusion and/or recirculation such as, e.g., to induce priming/activation in response to tumor antigen recognition, circulating T cells can be removed and transferred to unexposed matched PTO TOCs such as, e.g., to test activation levels and/or tumor killing. Non-limiting exemplars of device channel architectures include, but are not limited to, daisy-chain, e.g., single larger chamber. These primed and/or activated T cells may be administered to a patient. FIG. 11D shows another example schematic illustrating that following T cell infusion and/or recirculation such as, e.g., to induce priming/activation in response to tumor antigen recognition, circulating T cells can be removed and transferred to unexposed matched PTO TOCs such as, e.g., to test activation levels and/or tumor killing. These primed and/or activated T cells may be administered to a patient.

DETAILED DESCRIPTION OF EXAMPLE EMBODIMENTS

Figure 1A:
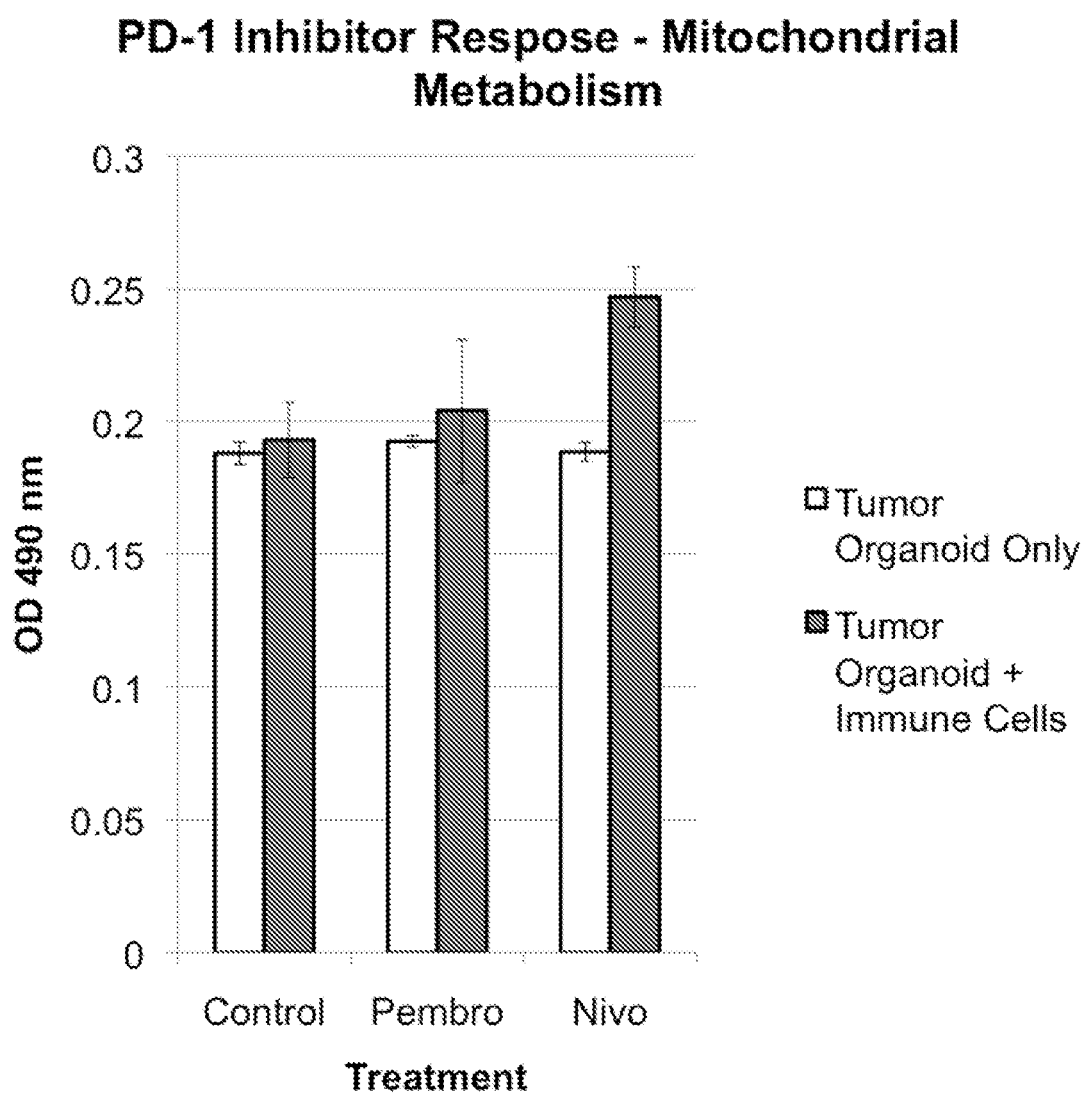
FIGS. 1A-1C show immunotherapy effects on patient tumor organoids with or without immune cells derived from matched lymph nodes obtained from the same patient.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific teal's) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of ±10%, ±5%, ±1%, ±0.5%, or even±0.1% of the specified value as well as the specified value. For example, "about X" where X is the measurable value, is meant to include X as well as variations of ±10%, ±5%, ±1%, ±0.5%, or even±0.1% of X. A range provided herein for a measureable value may include any other range and/or individual value therein.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

As used herein, the terms "increase," "increases," "increased," "increasing," and similar terms indicate an elevation in the specified parameter of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction," "inhibit," and similar terms refer to a decrease in the specified parameter of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

"Cells" and "cell" as used in the present invention are, in general, animal cells, particularly mammalian and primate cells, examples of which include but are not limited to human, dog, cat, rabbit, monkey, chimpanzee, cow, pig, goat. The cells may be differentiated at least in part to a particular cell or tissue type, such as liver, intestine, pancreas, lymph node, smooth muscle, skeletal muscle, central nerve, peripheral nerve, skin, immune system, etc. Some cells may be cancer cells, as discussed further below, in which case they optionally may express (naturally, or by recombinant techniques) a detectable compound, as also discussed further below.

"Three dimensional tissue construct" and "organoid" are used interchangeably herein and, as used herein, refer to a composition of live cells, typically in a carrier media, arranged in a three-dimensional or multi-layered configuration (as opposed to a monolayer). An organoid is an artificial, three-dimensional construct created in vitro to mimic or resemble the functionality and/or histological structure of an organ, tissue, or a portion thereof. Suitable carrier media include hydrogels, such as cross-linked hydrogels as described below. Additional example hydrogels include, but are not limited to, those described in PCT/US2015/055699, PCT/US2017/058531, and U.S. application Ser. No. 16/156, 535 filed Oct. 10, 2018, the contents of each of which are incorporated herein by reference in their entirety. An organoid may comprise one or more (e.g., 1, 2, 3, 4, or more) differentiated cell type(s) depending upon the particular tissue and/or organ being modeled or emulated. Some organoids may comprise cancer cells, as discussed further below. When the organoid comprises cancer cells, they may include tissue cells and/or may include a tissue mimic without cells, such as an extracellular matrix (or proteins and/or polymers derived therefrom), hyaluronic acid, gelatin, collagen, alginate, etc., including combinations thereof. Thus, in some embodiments, cells are mixed together with an extracellular matrix, or cross-linked matrix, to form the organoid, while in other embodiments cell aggregates such as, e.g., spheroids and/or organoids may be pre-formed and then combined with the extracellular matrix and/or a composition of the present invention.

In some embodiments, an organoid may be present in and/or formed in a hydrogel comprising thiolated hyaluronic acid (also referred to interchangeably herein as thiol-modified hyaluronic acid), methacrylated collagen (also referred to interchangeably herein as methacrylate-modified collagen), and water. One or more (e.g., 1, 2, 3, 4, 5, 6, 7, or more) additional components may be present in the hydrogel. For example, in some embodiments, an organoid may be present in a hydrogel comprising methacrylated gelatin (GelMa), heparin sulfate, chondroitin sulfate, alginate sodium salt, unmodified gelatin, elastin, non-thiolated hyaluronic acid, non-methacrylated collagen (e.g., Type I, II, III, and/or IV collagen), one or more components for modifying elastic modulus of the composition, one or more components for cell adhesion profile modification, one or more components for tissue-specific biochemical modification, and/or one or more small molecules (e.g., a small molecule that can has additional cross-linking capability and/or can provide hydrogen bonding and/or non-covalent complexing). In some embodiments, an organoid of the present invention may be present in and/or formed in a hydrogel comprising a photoinitiator, about 1% w/v thiolated hyaluronic acid, and about 4 mg/mL methacrylated collagen, optionally wherein the thiolated hyaluronic acid and methacrylated collagen are mixed in a 1:3 ratio by volume (thiolated hyaluronic acid: methacrylated collagen), and crosslinked via photopolymerization (e.g., with UV light). In some embodiments, thiolated hyaluronic acid and methacrylated collagen are mixed in a ratio by volume of about 3:1, 2:1, 1:1, 1:2, 1:3, 1:4, or 1:5 (thiolated hyaluronic acid: methacrylated collagen). The volume of the hydrogel in which an organoid is present and/or deposited may be in a range of about 1, 5, 10, 15, or 20 µL to about 25, 30, 35, 40, 45, 50, 55, or 60 µL. In some embodiments, the volume of the hydrogel in which an organoid is present and/or deposited may be about 1, 5, 10, 15, 20, 25, 30, 35, 40, 45, 50, 55, or 60 µL.

In some embodiments, an organoid and/or hydrogel of the present invention may be present in reservoir and/or a plurality of reservoirs (e.g., wells of a well plate). The reservoir(s) may be any suitable reservoir or container that holds the organoid and/or hydrogel. In some embodiments, the reservoir is a well of a well plate such as, but not limited to, a well in a 6-well plate, a 12-well plate, a 24-well plate, a 48 well plate, a 96-well plate, or 384-well plate.

In some embodiments, an organoid may be present in a hydrogel comprising a protein (e.g., an adhesion protein) and/or proteoglycan, optionally a modified protein and/or modified proteoglycan. In some embodiments, the protein and/or proteoglycan may be modified with one or more functional group(s), such as, e.g., modified with a maleimide, that can bind and/or crosslink to thiolated hyaluronic acid, non-thiolated hyaluronic acid, methacrylated collagen, and/or non-methacrylated collagen. In some embodiments, an organoid may be present in a hydrogel comprising fibronectin, heparin, and/or laminin, optionally a modified fibronectin, heparin, and/or laminin (e.g., modified with a maleimide), or other cell adhesion protein(s) and/or or cell adhesion protein peptide derivative(s).

One or more growth factor(s) may be present in a hydrogel. In some embodiments, the hydrogel comprises one or more growth factor(s) that are linked and/or bound by a heparin pendant chain. The one or more growth factor(s) may be appropriate for the particular cells that may be present in and/or added to the hydrogel and/or for the particular tissue substitute and/or organoid being produced. In some embodiments, growth factors and/or other growth promoting proteins may be provided in a decellularized extracellular matrix composition (ECM) from a tissue corresponding to the tissue cells (e.g., decellularized extracellular liver matrix when the live animal cells are liver cells; decellularized extracellular cardiac muscle matrix when the live animal cells are cardiac muscle cells; decellularized skeletal muscle matrix when the live animal cells are skeletal muscle cells; etc.). Additional collagens, glycosaminoglycans, and/or elastin (e.g., which may be added to supplement the extracellular matrix composition), etc., may also be included.

In some embodiments, an organoid may be present in a hydrogel that may be customized to match the biochemical profile of one or more (e.g., 1, 2, 3, 4, 5, or more) tissue(s) (e.g., a tissue found in a mammalian body). In some embodiments, an adhesion protein such as, e.g., one found in a particular tissue, may be synthetically modified to allow for direct coupling to a component in the composition (e.g., the thiolated hyaluronic acid and/or methacrylated collagen). Growth factors may be linked through heparin pendant chains. Fibronectin, laminin, and/or other adhesion proteins may be synthetically modified to have one or more chemical group(s) that crosslink directly into a component in the composition (e.g., the thiolated hyaluronic acid and/or methacrylated collagen), which may allow for tissue-specific customization. In some embodiments, inclusion of covalently linked fibronectin in the composition may have a significant influence in maintaining function of an organoid formed and/or provided in the composition (e.g., a liver organoid).

The cells may be incorporated into a composition and/or hydrogel in any suitable form, including as unencapsulated cells, or as cells previously encapsulated in spheroids, or pre-formed organoids (as noted above). Animal tissue cells encapsulated or contained in polymer spheroids can be produced in accordance with known techniques, or in some cases are commercially available (see, e.g., Insphero A G, 3D *Hepg2 Liver Microtissue Spheroids* (2012); Inspherio AG, 3D *InSight™ Human Liver Microtissues*, (2012)).

In some embodiments, an organoid of the present invention comprises cells that are human-derived cells, and, in some embodiments, the organoid comprises cells that consist of human-derived cells. An organoid of the present invention may express and/or produce one or more biomarkers (e.g., 1, 2, 3, 4, or more) that are the same as a biomarker produced by the cells in vivo. For example, liver cells in vivo produce albumin and an organoid of the present invention comprising liver cells may express albumin. In some embodiments, an organoid may express a biomarker in the same amount or in an amount that is ±20%, ±10%, or ±5% of the average amount produced and/or expressed by corresponding cells in vivo. Example biomarkers include, but are not limited to, albumin, urea, glutathione S-transferase (GST) (e.g., α-GST), chemokines (e.g., IL-8, IL-1β, etc.), prostacyclin, SB100B, neuron-specific enolase (NSE), myelin basic protein (MBP), hormones (e.g., testosterone, estradiol, progesterone, etc.), inhibin A/B, lactate dehydrogenase (LDH), and/or tumor necrosis factor (TNF). The cells may be differentiated or undifferentiated cells, but are in some embodiments tissue cells (e.g., liver cells such as hepatocytes, pancreatic cells, cardiac muscle cells, skeletal muscle cells, etc.).

Choice of cells will depend upon the particular organoid being created, and the cells may be labeled with a detectable compound, such as, but not limited to, with a fluorescent compound (e.g., dye, protein, etc.). For example, for a liver organoid, liver hepatocyte cells may be used. For a peripheral or central nerve organoid, peripheral nerve cells, central nerve cells, glia cells, or combinations thereof may be used. For a bone organoid, bone osteoblast cells, bone osteoclast cells, or combinations thereof may be used. For a lung organoid, lung airway epithelial cells may be used. For a lymph node organoid, follicular dendritic lymph cells, fibroblastic reticular lymph cells, leukocytes, B cells, T cells, any myeloid cell (e.g., any myeloid in origin (inclusive of dendritic cells and phagocytes)), any lymphoid in origin cell, or combinations thereof may be used. For a smooth and/or skeletal muscle organoid, smooth muscle cells, skeletal muscle cells, or combinations thereof may be used. For a skin organoid, skin keratinocytes, skin melanocytes, or combinations thereof may be used. The cells may be differentiated upon initial incorporation into the composition, or undifferentiated cells that are subsequently differentiated may be used. Additional cells may be added to any of the compositions and/or hydrogels. In some embodiments, tumor cells and/or immune cells are added to an organoid (e.g., a liver organoid), or an organoid can be primarily comprised of tumor cells, with or without immune cells. In some embodiments, an organoid of the present invention comprises, consists essentially of, or consists of one or more types of immune cell(s), which may be selected from white blood cells, peripheral blood mononuclear cells, follicular dendritic lymph cells, fibroblastic reticular lymph cells, leukocytes, B cells, T cells, any myeloid cell (e.g., any myeloid in origin (inclusive of dendritic cells and phagocytes)), and/or any lymphoid in origin cell. In some embodiments, the one or more types of immune cell(s) may be collected and/or derived from a lymph node (e.g., a lymph node biospecimen), from bone marrow, and/or from the peripheral blood of a subject or a fraction thereof (e.g., a white blood cell fraction, e.g., a peripheral blood mononuclear cell (PBMC) fraction).

In some embodiments, an organoid of the present invention may be a mixed organoid e.g. in that tumor cells and immune cells are present in the same organoid (also referred to herein as a mixed tumor/immune organoid). In some embodiments, an organoid of the present invention may be a symbiotic organoid. A "symbiotic organoid" as used herein refers to at least one organoid in which tumor cells and immune cells are in contact. In some embodiments, a symbiotic organoid consists of one organoid comprising tumor cells and immune cells (e.g., a mixed organoid). In some embodiments, a symbiotic organoid comprises at least two organoids with a first organoid of the at least two organoids comprising tumor cells and a second of the at least two organoids comprising immune cells, wherein at least a portion of the first organoid and at least a portion of the second organoid are in contact with one another. "In contact" as used herein in reference to a symbiotic organoid refers to at least a portion of the tumor cells and at least a portion of the immune cells being sufficiently close to be in physical contact, have cell to cell communication, and/or be present in and/or on the same organoid. In some embodiments, two or more separate organoids may grow together to form a symbiotic organoid. In some embodiments, cell movement may be required (e.g., via circulation) to provide and/or enable communication between an immune organoid and separate tumor organoid.

A patient-derived tumor organoid (PTO) of the present invention may recapitulate the tumor microenvironment of the patient such as, e.g., by incorporating tumor cells along with associated stroma and/or tumor-infiltrating leukocytes (TILs), each obtained from a patient's own tumor. Lymph nodes incorporate 80% of the immune system representation of every individual patient, and have a central role in development of adaptive immunity though their abundance of antigen presenting cells (APCs). In some embodiments, an immune tumor organoid of the present invention may comprise peripheral blood mononuclear cells, optionally when lymph node tissue is not available for a patient.

Cancer cells optionally used in the present invention may be any type of cancer cell, including but not limited to melanoma, carcinoma, sarcoma (including, but not limited to, angiosarcoma, myxofibrosarcoma, leiomyosarcoma, dermatofibrosarcoma protuberans), blastoma, glioma, appendiceal, myeloma (e.g., multiple myeloma), head and neck, breast, lung, and astrocytoma cells, etc. In some embodiments, the cancer cells used in the present invention express N-cadherin, and/or show epithelial to mesenchymal transition. Cancer cells may be cancer cells from any tissue of origin, including but not limited to intestinal (small intestine, large intestine, colon, vermiform appendix), lung, breast, prostate, skin, bone, brain, liver, pancreatic, uterine, cervical, testicular, and ovarian cancer cells, etc.

In some embodiments, cells may be obtained from a subject, such as, for example, a subject or patient undergoing treatment for cancer and/or that has cancer and/or a subject that has a compromised immune system. In some embodiments, cells are tumor cells, such as, e.g., patient biopsy-derived tumor cells, and organoids prepared from such cells may be used to screen potentially effective drugs and/or treatments. Any type of tumor cell may be used in an organoid, device, and/or method of the present invention including, but not limited to, intestinal (small intestine, large intestine, colon, vermiform appendix), lung, breast, prostate, skin, bone, brain, liver, pancreatic, uterine, cervical, testicular, and ovarian tumor cells, etc. Example biopsy-derived tumor organoids include, but are not limited to, mesothelioma, colorectal, appendiceal, lung, melanoma, and sarcoma organoids. In some embodiments, the cells include benign cells (also referred to as non-cancerous cells) obtained from a tissue biopsy. The cells may be differentiated at least in part to a particular cell or tissue type, such as brain, liver, intestine, pancreas, lymph node, smooth muscle, skeletal muscle, central nerve, peripheral nerve, skin, immune system, etc. Biopsy-derived cells (e.g., tumor and/or benign) may be used to form and/or prepare an organoid of the present invention, and the resulting organoid may be prepared and/or used in a method and/or device of the present invention within about 1, 2, 3, 4, 5, 6, 7, or 8 days after the biopsy. In some embodiments, the cells may be labeled with a detectable compound, such as, but not limited to, with a fluorescent compound (e.g., dye, protein, etc.). In some embodiments, an organoid comprising tumor cells, device comprising the same, and/or method of use thereof may be as described in International Application No. PCT/US2017/045277, the content of which is incorporated herein by reference in its entirety.

In some embodiments, an organoid of the present invention is not prepared from and/or does not comprise cells from an immortalized cell line. Organoids of the present invention may comprise and/or be prepared using high functioning cells, such as, but not limited to, primary cells and/or stem cells, e.g., induced pluripotent stems and/or differentiated iPS-derived cells.

In some embodiments, an organoid of the present invention comprises a core comprised of live tumor cells; and a shell surrounding (e.g., encapsulating) the core, the shell comprised of live immune cells and/or live benign cells (e.g., tissue cells, non-cancerous cells, etc.). The benign cells may be obtained and/or derived from a subject, such as, e.g., a tissue in the subject, and optionally from the same subject as the tumor cells and/or immune cells. In some embodiments, the live benign cells may be obtained and/or derived from a tissue biopsy and/or may be tissue specific. An organoid comprising live benign cells may be separate (e.g., separately formed and/or present in a different chamber of a device) from an organoid comprising live tumor cells and/or immune cells.

When cells (e.g., immune cells, tumor cells, and/or benign cells) are obtained from a subject such as, e.g., from a tissue sample and/or tumor biopsy from a subject, different cell populations may be separated to provide one or more separate populations of cells, and one or more of the separate populations of cells may be labeled and/or used to prepare an organoid as described herein. Methods of separating different populations of cells are known to those of skill in the art and any suitable method may be used, such as, but not limited to, fluorescence activated cell sorting (FACS). When two or more populations of cells are labeled, the two or more populations of cells may have a different detectable signal. In some embodiments, the tissue sample and/or tumor biopsy may be genetically sequenced in part or in full in order to identify mutations, and any mutations identified may indicate and/or suggest one or more compound(s) of interest for therapeutic purposes for the subject (e.g., immune system modulating activity and/or anti-tumor activity). A method of the present invention may comprise screening the one or more compound(s) of interest that were identified in the genetic sequencing and contacting each of the one or more compound(s) of interest and/or a combination thereof to the organoid prepared using the cells from the tissue sample. An organoid of the present invention may have the same or substantially the same heterogeneity as a tissue and/or tumor found in vivo in a subject.

The one or more populations of cells (each of which may optionally be labeled) may be combined in any suitable manner. In some embodiments, the one or more populations of cells may be added to the same common media and/or hydrogel. In some embodiments, the one or more populations of cells may be used to form an organoid as described herein that is encapsulated by a hydrogel of the present invention. One or more different populations of cells in an organoid of the present invention may be present in substantially the same (e.g., within about ±20%) amount as the amount of cells in that population in a tissue and/or tumor in vivo. In some embodiments, when cells have been obtained from a tissue sample from a subject, sorted and/or labeled, the different populations of cells are combined in substantially the amount as the amount present in the tissue sample. In some embodiments, cells (e.g., tumor cells) used to for an organoid of the present invention may not be sorted, which may aid in providing an organoid having the native heterogeneity. For example, in some embodiments, tumor cells are not sorted prior to forming a tumor organoid and/or mixed organoid of the present invention, which may allow the tumor organoid to mimic the native tumor heterogeneity by including, for example, any stromal cells, endothelial cells, immune cells, etc. present in the original biospecimen and/or sample. Similarly, in some embodiments, immune cells are not sorted prior to forming an immune organoid and/or mixed organoid of the present invention, which may allow for the organoid to maintain other cells such as, e.g., B cells, dendritic cells, macrophages, etc., in the organoid that may be important to T cell education and/or activation needed to kill tumor cells. Thus, an organoid of the present invention can include non-tumor and/or non-T cell support cells, which may help maintain the tumor or immune (e.g., lymph node) microenvironment and/or aid in maintaining viability through a variety of signaling mechanisms and some natural remodeling of the ECM. In some embodiments, a tumor organoid of the present invention recapitulates the tumor microenvironment by incorporating tumor cells along with associated stroma and/or tumor infiltrating leucocytes (TILs). In some embodiments, when immune cells are obtained from the blood, a red blood cell lysis is performed to get rid of red blood cells.

In some embodiments, at least two (e.g., 2, 3, 4, 5, 6, 7, 8, or more) different organoids are formed with cells obtained and/or derived from a single subject (e.g., using one or more biopsies from the subject), with at least one organoid comprising live tumor cells from a tumor biopsy from the subject and at least one separate organoid comprising live immune cells and/or live benign (e.g. liver) cells from the subject. In some embodiments, at least two (e.g., 2, 3, 4, 5, 6, 7, 8, or more) organoids are formed with cells obtained and/or derived from a single subject (e.g., using one or more biopsies from the subject), with at least one organoid comprising live tumor cells from a tumor biopsy from the subject and optionally comprising immune cells from the subject, and at least one separate organoid comprising live benign cells from the subject that are the same tissue type as the live tumor cells and optionally comprising immune cells from the subject. In some embodiments, an organoid of the present invention may be created by combining cells obtained and/or derived from a single subject using one or more biopsies from the subject (e.g., a mixed tumor/lymph node symbiotic organoid created by combining cells obtained and/or derived from a tumor biopsy from a subject and cells obtained and/or derived from a separate lymph node biopsy from the same subject). In some embodiments, a tissue biopsied from a subject may be used to prepare one or more organoids of the present invention, optionally with cells obtained from a 2 mm×2 mm minced tissue. In some embodiments, an organoid of the present invention may be useful as a tumor model and/or as an immune system model. For example, the organoid may useful for evaluating immunological activity and/or modulating the immune system and/or useful for screening one or more cancer therapies and/or immunotherapies. For example, tumor organoids of the present invention, e.g., mixed tumor/immune organoids (e.g., mixed tumor/lymph node symbiotic organoids) may allow for screening of the creation of adaptive immunity through training of a patient's peripheral blood T cells to recognize tumor antigens that are exhibited on the surface of antigen presenting cells (APCs) incorporated in the patient's own lymph node/tumor symbiotic organoids.

In some embodiments, an organoid has a diameter and/or smallest dimension of about 50 µm, 100 µm, or 200 µm to about 350 or 500 µm, such as, for example, about 50, 75, 100, 150, 200, 250, 300, 350, 400, 450, or 500 µm. In some embodiments, an organoid has a diameter and/or smallest dimension of less than about 100, 90, 80, 70, 60, or 50 µm. In some embodiments, an organoid is about 1 µL to about 20 µL in volume such as, for example, about 1, 2, 3, 4, 5, 6, 7, 8, 9, 10, 11, 12, 13, 14, 15, 16, 17, 18, 19, or 20 µL in volume. The organoid may comprise about 1,500, 2,000, or 5,000 to about 10,000, 25,000, or 50,000 cells in total or about 1,000, 5,000, 10,000, or 50,000 to about 75,000, 100,000, 150,000, 250,000, 500,000, 750,000, 1,000,000, 50,000,000, or 100,000,000 cells in total. In some embodiments, an organoid of the present invention may comprise about 1, 2, or 5 million to about 10, 25, 50, or 100 million cells per mL. In some embodiments, an organoid of the present invention may comprise about 10 million cells per mL or 20 million cells per mL. In some embodiments, an organoid of the present invention may comprise about 5 or 10 million cells per mL to about 15 or 20 million cells per mL. An organoid of the present invention may be in any suitable shape, such as, e.g., any three-dimensional shape or multi-layered shape. In some embodiments, an organoid of the present invention is in the form of a spheroid. In some embodiments, an organoid of the present invention may be self-organized in a suspension or medium (e.g., a cross-linked hydrogel).

"Subjects" as used herein are, in general, human subjects, although aspects of the invention may be implemented with other animal subjects, particularly mammalian subjects (e.g., dogs, cats, horses, goats, sheep) for veterinary and/or research purposes. Subjects may be male or female and of any age, including infant, juvenile, adolescent, adult, and geriatric.

"Growth media" and "culture media" are used interchangeably herein and may be any natural or artificial growth media (typically an aqueous liquid) that sustains the cells used in carrying out the present invention. Examples include, but are not limited to, an essential media or minimal essential media (MEM), or variations thereof such as Eagle's minimal essential medium (EMEM) and Dulbecco's modified Eagle medium (DMEM), as well as blood, blood serum, blood plasma, lymph fluid, etc., including synthetic mimics thereof. In some embodiments, the growth media includes a pH color indicator (e.g., phenol red).

"Test compound", "candidate compound" and "compound of interest" are used interchangeably herein and may be any compound or agent for which a pharmacological or physiological activity is to be determined such as, e.g., for which a pharmacological or physiological activity on a cell or tissue (e.g., a cardiac tissue) and/or an interaction between two test compounds/agents is to be determined. For demonstrative purposes, isoproterenol, quinidine, propranolol, and epinephrine are example test compounds. However, any compound/agent may be used including organic compounds such as, but not limited to, proteins, peptides, nucleic acids, and/or small organic compounds (aliphatic, aromatic, and mixed aliphatic/aromatic compounds). Candidate compounds may be generated by any suitable techniques, including randomly generated by combinatorial techniques, and/or rationally designed based on particular targets. Where a drug interaction is to be studied, two (or more) test compounds may be administered concurrently, and one (or both) may be known compounds, for which the possible combined effect is to be determined. In some embodiments, two or more test compounds may be administered in a manner similar to in vivo administration for a subject (e.g., similar to staged infusion of two or more test compounds), which may be concurrent administration or sequential administration. In some embodiments, the test compound is a metal, such as, but not limited to, aluminum, lead, etc. In some embodiments, the test compound is a heavy metal, such as, but not limited to, arsenic, cadmium, chromium, lead, and/or mercury. In some embodiments, the test compound is a pesticide. In some embodiments, the test compound is a chemotherapy agent and/or an immunotherapy agent such as, e.g., an immune checkpoint inhibitor (ICI). In some embodiments, an immunotherapy agent modulates and/or affects one or more activities and/or components of a subject's immune system. In some embodiments, the immunotherapy agent may be vemurafenib, ipilimumab, nivolumab, and/or pembrolizumab. In some embodiments, the test compound is a check point inhibitor (e.g., PD-1 inhibitor, CTLA-4 inhibitor, etc.). In some embodiments, the test compound comprises engineered immune cells such as, e.g., CAR T cells. In some embodiments, the test compound is immunogenic attenuated immunoactivating virus. In some embodiments, drug screening may be performed and/or carried out in a high-throughput method. For example, the test compound may be present in a reservoir and/or a plurality of reservoirs (e.g., wells of a well plate). In some embodiments, the reservoir is a well of a well plate such as, but not limited to, a well in a 6-well plate, a 12-well plate, a 24-well plate, a 48 well plate, a 96-well plate, or 384-well plate.

"Detectable compound" as used herein may be a fluorescent compound (e.g., a fluorescent protein (e.g., red fluorescent protein, green fluorescent protein, etc.)), an antigenic protein or peptide to which an antibody coupled to an enzyme, fluorescent, or radioactive group, or other label, will specifically bind, or any other suitable detectable compound. The detectable compound may be one naturally occurring in a cell (e.g., a cancer cell, such as, e.g., a cell marker protein that is expressed at higher levels in cancer cells than non-cancer cells), or one inserted into a cell by genetic engineering/recombinant DNA techniques (i.e., heterologous). In some embodiments, the detectable compound is a quantum dot (QD), a fluorescent organic dye, and/or a fluorescent protein. In some embodiments, a cell may express (naturally, or by recombinant techniques) a detectable compound.

A detectable compound may be any suitable compound that provides and/or generates a detectable signal that allows for differentiation and/or identification of a cell and/or cell population. A detectable signal may be provided and/or generated by one or more detectable compounds associated with a cell. In some embodiments, the detectable signal is a signal (e.g., an optical and/or electrical signal) that is generated by one or more detectable compounds (e.g., chemicals, proteins, etc.) associated with (e.g., applied to, attached to, bound to, compounded with, etc.) a cell. A detectable signal may be optically and/or electronically detectable, which may be perceived visually with the human eye and/or electronically read, detected, and/or obtained using methods known to those of skill in the art. In some embodiments, a detectable signal for a cell and/or cell population may be the absence of a signal (i.e., no detectable signal such as, e.g., no detectable fluorescence from the cell). In some embodiments, a detectable signal for a cell and/or cell population is a fluorescence signal.

A device and/or system of the present invention may comprise a detector (e.g., a camera) and/or an excitation source (e.g., an excitation light source). The detector may detect and/or image the detectable signal from a cell and/or cell population. The excitation source may be used to and/or may generate the detectable signal, such as, e.g., may be used to provide and/or generate light which may cause a detectable compound to fluoresce and thereby provide and/or generate the detectable signal.

In some embodiments, at least a portion of a device (e.g., a microfluidic device) of the present invention is transparent. For example, in some embodiments, the top and/or bottom substrate of the device may be transparent and/or the hydrogel present in the device may be transparent. The device may comprise a detector (e.g., a camera) operatively associated with the device. The detector may be operatively associated with one or more of the chambers of the device. In some embodiments, the detector is provided above and/or below the device and an excitation source may be provided above and/or below the device. In some embodiments, the detector comprises the excitation source (e.g., the light such as the flash and/or LED of a camera). The detector may be configured for detecting (e.g., imaging) cells in one or more chambers of the device. In some embodiments, the device may include a detector (e.g., a LED/CCD detector) positioned to allow images of labeled cells in contact with one or more chambers of the device to be imaged and/or quantified in real time. In some embodiments, the detector may capture images (e.g., fluorescent images) at predetermined intervals and/or may capture images and/or incidences of colonization, migration, and/or growth of labeled cells in and/or from an organoid present in the one or more chambers, which may enable real-time observation and/or quantitation of cells in the organoid and/or their growth, metastasis, migration, and/or the like.

Provided according to embodiments of the present invention are organoids comprising at least one type of immune cell (also referred to herein as an immunology organoid). The at least one type of immune cell may be collected and/or derived from a lymph node, bone marrow, and/or peripheral blood (e.g., a lymph node biospecimen, bone marrow biopsy, and/or peripheral blood draw) in a subject. In some embodiments, the at least one type of immune cell is selected from follicular dendritic lymph cells, fibroblastic reticular lymph cells, leukocytes, peripheral blood mononuclear cells, B cells, T cells, any myeloid cell (e.g., any myeloid in origin (inclusive of dendritic cells and phagocytes)), and/or any lymphoid in origin cell. In some embodiments, the organoid comprising at least one type of immune cell comprises white blood cells. In some embodiments, the at least one type of immune cell comprises a detectable compound (e.g., a fluorescent compound).

In some embodiments, the organoid comprising at least one type of immune cell serves as an in vitro model immune system, optionally for a particular subject/patient. This may allow for screening of drugs that can influence and/or modulate the immune system, such as immunotherapy drugs (e.g., PD-1 and CTLA-4 inhibitors, IL-2, interferon), which may enable immune cells to attack tumor cells. In some embodiments, an immunology organoid of the present invention may be used to track neutrophil populations optionally in the context of homing to tissue inflammation, to validate genetic analysis, and/or to select and/or optimize therapy for a subject/patient.

Figure 12:
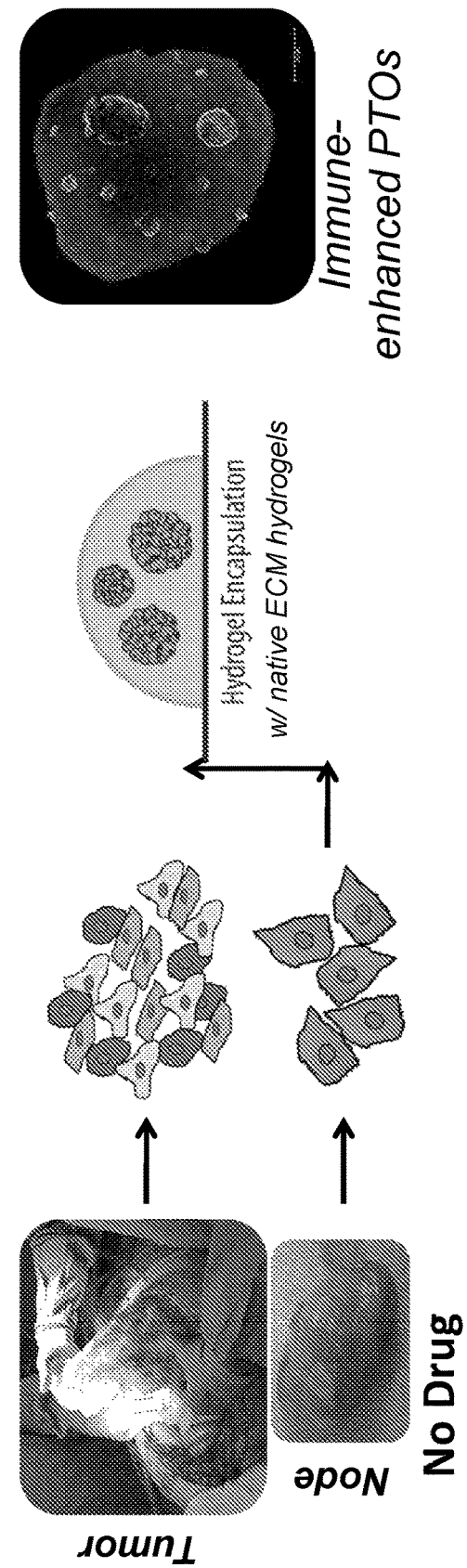
FIG. 12 is a schematic illustrating the incorporation of immune components into patient tumor organoids according to some embodiments of the present invention.
Figure 13:
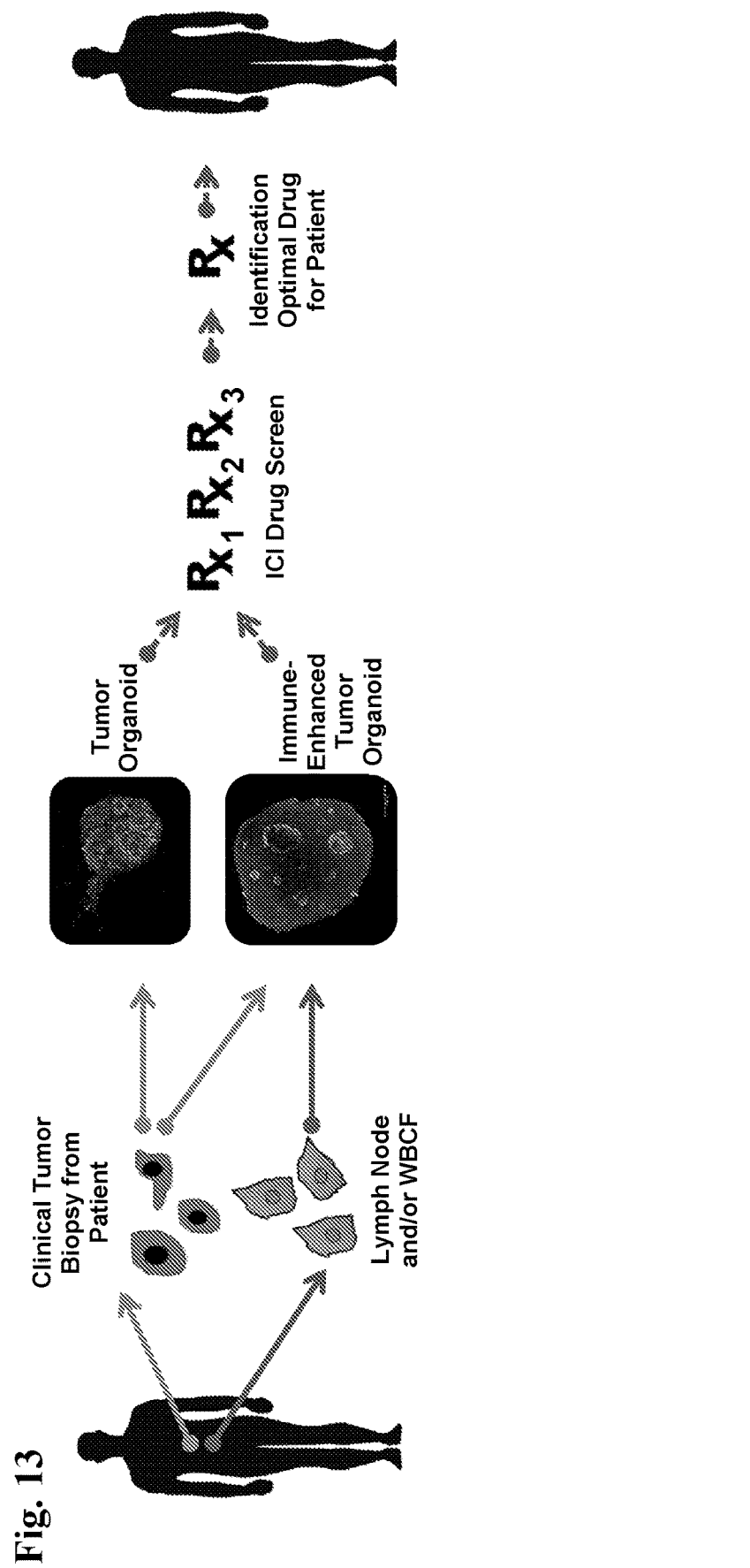
FIG. 13 is a schematic illustrating the incorporation of immune components into patient tumor organoids and methods of use for personalized medicine according to some embodiments of the present invention.

An organoid of the present invention may comprise cells from a lymph node (e.g., cells from a subject's lymph node), bone marrow, and/or white blood cells and/or components thereof (e.g., from a subject, optionally the same subject as the lymph node cells). In some embodiments, an organoid of the present invention comprises cells from pieces of resected lymph nodes, optionally removed at the time of tumor resection, white blood cells (e.g., obtained from peripheral blood), and/or cells obtained from a bone marrow biopsy with all of the cells obtained and/or derived from the same subject. The subject may have a tumor and/or cancer and/or immunotherapy may be a treatment option for the subject. For example, as illustrated in FIG. 12, tumor cells may be obtained from a subject's tumor and/or immune cells may be obtained from a lymph node from the subject, and the tumor cells and immune cells may be combined and/or encapsulated in a hydrogel (e.g., a native ECM hydrogel including gelatin, collagen, hyaluronic acid, adhesion proteins (e.g., fibronectin, laminin, etc.) and/or growth factors) to form an immune enhanced patient tumor organoid. Another example of the present invention is illustrated in FIG. 13, which shows that tumor cells can be obtained from a clinical tumor biopsy from a patient and immune cells can be obtained from a lymph node and/or white blood cell fraction (WBCF) from the patient. As shown in FIG. 13, a portion of these tumor cells from the patient can be used to form a tumor organoid devoid of immune cells from the lymph node or WBCF sample and another portion of the tumor cells from the patient can be combined with the immune cells from the lymph node or WBCF sample to form an immune enhanced tumor organoid. According, to some embodiments, a method of the present invention comprises exposing and/or contacting such organoids separately to one or more test compounds (e.g., a chemotherapy agent and/or an immunotherapy agent) and determining and/or identifying suitable test compounds (e.g., drugs such as, e.g., an immune checkpoint inhibitor (ICI)) that may be used to treat the patient from which the cells for the organoids were obtained (FIG. 13).

In some embodiments, an organoid of the present invention may comprise one or more types of live immune cells that are each present in the organoid in an amount that is about the same as the amount present in a lymph node, bone marrow, and/or blood of a subject for that type. For example, T cells may be present in an organoid of the present invention in an amount that is about the same as the amount of T cells present in vivo in a lymph node of a subject. In some embodiments, two or more different types of live immune cells are present in an organoid of the present invention in a ratio or amount similar to the ratio or amount of each of the immune cells in vivo such as, e.g., in a lymph node, bone marrow, and/or blood of a subject. In some embodiments, one or more types of live immune cells may be present in an organoid of the present invention in an amount of about 1,500, 2,000, or 5,000 to about 10,000, 25,000, or 50,000 cells or about 1,000, 5,000, 10,000, or 50,000 to about 75,000, 100,000, 150,000, 250,000, 500,000, 750,000, 1,000,000, 50,000,000, or 100,000,000 cells. In some embodiments, an organoid of the present invention may comprise one or more types of live immune cells in an amount of about 1, 2, or 5 million to about 10, 50, or 100 million cells per mL.

An organoid of the present invention (e.g., an immunology organoid) may be used in a device (e.g., a microfluidic device) with a tumor organoid (e.g., an organoid with tumor cells that are optionally from the same subject as the lymph node and/or white blood cells). The device may be used to screen the effectiveness of one or more immunotherapy agent(s) (e.g., PD-1 and/or CTLA-4 inhibitors) to target tumors in a subject and/or to allow immune cells in the device (e.g., in the immunology organoid) to attack the tumor cells. The immune cells and/or tumor cells may be fluorescently labeled to track and/or colocalize immune cells with T-cell activation markers and/or cell death indicators of tumor cells. In some embodiments, tumor cell viability versus cell death may be assessed with a device of the present invention. In some embodiments, where a patient (e.g., the subject from whom one or more of the cells were obtained) receives a treatment (e.g., an immunotherapy drug), the in vitro responses with a device and/or organoid of the present invention may be compared to or predictive of real life patient outcomes. In some embodiments, a method of the present invention may comprise correlating and/or predicting in vitro outcomes with in vivo outcomes.

In some embodiments, an organoid of the present invention comprises at least one type of immune cell as described herein and live tumor cells. The live tumor cells may be collected and/or derived from a tumor in a subject. In some embodiments, the at least one type of immune cell and the live tumor cells may be collected and/or derived from the same subject. The live tumor cells and the at least one type of immune cell may be present in an organoid in any suitable ratio. In some embodiments, the live tumor cells and the at least one type of immune cell may be present in the organoid in a ratio of about 1:1 or 5:1 to about 10:1, 20:1, 30:1, 40:1, 50:1, 60:1, 70:1, 80:1, 90:1, or 100:1 (tumor cells:immune cells). In some embodiments, the ratio may be about 10:1 to about 100:1 when only white blood cells and/or tumor-infiltrating lymphocytes (TILs) are present as the immune cell. In some embodiments, the ratio of tumor cells to immune cells may be about 1:1, 2:1, 3:1, 4:1, 5:1, 6:1, 7:1, 8:1, 9:1, or 10:1. In some embodiments, the live tumor cells and the at least one type of immune cell are present in the organoid in a ratio of about 5:1, 10:1, 50:1, or 100:1. In some embodiments, by providing an organoid and/or device comprising a tumor cells and/or immune cells from the same subject, the organoid and/or device may be used to assess whether standard chemotherapy agents and/or immunotherapy agents may be more effective for the subject. Providing an organoid and/or device comprising both immune cells and tumor cells from the same subject can provide a genetically matched immune system with an in vitro tumor model (e.g., the tumor organoid), which may be used to test and/or screen in vitro one or more immunotherapy and/or chemotherapy agents.

In some embodiments, an organoid of the present invention comprises benign cells. For example, an organoid of the present invention may comprise at least one type of immune cell as described herein and/or live tumor cells as described herein and may further comprise benign cells (e.g., blood vessel endothelial cells, stromal cells, etc.). In some embodiments, an organoid of the present invention comprises at least one type of immune cell as described herein and benign cells (e.g., blood vessel endothelial cells, stromal cells, etc.). The benign cells may be collected and/or derived from the same subject as the subject from which the at least one type of immune cell and/or live tumor cells are obtained and/or derived. The cells (e.g., tumor cells, immune system cells, and/or benign cells) in an organoid can be arranged in the organoid in any suitable manner. In some embodiments, the cells (e.g., tumor cells, immune system cells, and/or benign cells) are combined and/or mixed together and may be randomly distributed in the organoid. In some embodiments, an organoid of the present invention comprises a core of live tumor cells and/or live immune system cells, and a shell comprising at least one type of immune system cell and/or live benign cells. In some embodiments, benign cells (e.g., endothelial cells and/or stromal cells) may be at least partially around an organoid of the present invention, the organoid optionally including tumor and/or immune cells. In some embodiments, an endothelial layer and/or barrier may be at least partially or fully around an organoid of the present invention. Cells that may be present on and/or around an organoid of the present invention (e.g., a tumor organoid or mixed organoid) include, but are not limited to, cells that may be present around a tumor in vivo. Example cells that may be present on and/or around an organoid of the present invention (e.g., a tumor organoid or mixed organoid) include, but are not limited to, epithelial cells, stroma cells, fibroblasts, stellate cells, astrocytes, glial cells, etc. In some embodiments, an organoid of the present invention comprises immune system cells in an amount of about 1%, 5%, 10%, 25%, 50% to about 55%, 60%, 75%, 80%, 90%, 95%, or 100% of the total number of cells present in the organoid. In some embodiments, an organoid of the present invention comprises immune system cells in an amount of about 1%, 5%, 10%, 15%, 20%, 25%, 30%, 35%, 40%, 45%, 50%, 55%, 60%, 65%, 70%, 75%, 80%, 85%, 90%, 95%, 97%, 98%, 99%, or 100% of the total number of cells present in the organoid. When an organoid of the present invention comprises immune system cells in an amount less than 100% of the total number of cells present in the organoid, then tumor cells and/or benign cells in any suitable amount may make up the remaining number/percentage of cells.

An organoid of the present invention may provide a patient-specific in vitro model system, which may be used to determine a treatment for the patient, optionally before initiation of therapy and/or treatment. In some embodiments, a compound of interest may be screened for immunological activity, modulation of the immune system, and/or anti-tumor activity, optionally in addition to an additional screening method, such as, but not limited to, genetic biomarker assessment and/or genetic profiling. In some embodiments, an organoid, device, and/or method of the present invention may allow and/or provide for cellular biomarker recognition, biomarker expression quantification, and/or real time testing of immunotherapy and/or chemotherapy drug efficacy including, for example testing the efficacy of an immunogenic virus that may be used for therapeutic purposes in a patient.

An organoid of the present invention may identify and/or be used to aid in identifying a tumor mutation and/or correlate the mutation with available drugs for a subject. In some embodiments, a method of the present invention identifies a therapy by an outcome achieved with an organoid of the present invention.

In some embodiments, devices and/or methods of the present invention may integrate patient-derived tumor organoids with components from the immune system (e.g., cells derived from lymph node biospecimens of the patient from which the tumor cells were obtained). These organoids, devices, and/or methods may be used in precision medicine-driven drug studies (e.g., used to identify of actionable mutations and/or genetic profiles and subsequent therapy customization) that assess drug efficacy of immunotherapy agents in vitro for individual patients. In some embodiments, tumor organoids and/or mixed tumor/immune organoids (e.g., mixed tumor/lymph node symbiotic organoids) may be prepared directly from fresh tumors, and these tumor organoids may replicate the tumor microenvironment and may allow for cellular biomarker recognition, biomarker expression quantification, and/or real time testing of immunotherapy and/or chemotherapy drug efficacy. An organoid of the present invention may be provided and/or contained in a microfluidic device, which may provide and/or enable parallel screening of multiple drugs and/or provide in fluid communication multiple tissues and/or tumors. In some embodiments, an organoid and/or device of the present invention may supplement genetic screens and/or be used to predict the extent of malignancy and/or optimal therapy for an individual patient, optionaly prior to administration to the patient. Drug screens can be performed with a variety of test compounds at various concentrations, and results may be obtained in less than about a week (e.g., less than a week from obtaining the cells from the patient that are used in preparing an organoid used in the drug screen). In contrast, typical genetic sequencing services do not result in actionable data sets for 3-4 weeks on average.

A device of the present invention may comprise an immunology organoid (e.g., an organoid comprising at least one type of immune cell) and a separate tumor organoid. In some embodiments, a device of the present invention comprises an organoid comprising both tumor cells and at least one type of immune cell. The organoid comprising tumor cells in a device of the present invention may comprise tumor cells from the same subject as the immune cells and may optionally include other cell populations such as, but not limited to, blood vessel endothelial cells and/or stromal cells. Including cell populations other than the organoid comprising tumor cells may aid in preserving the tumor heterogeneity and/or clonality, which may more realistically recapitulate a tumor.

In some embodiments, an immunology organoid may be upstream from, or otherwise in fluid communication with, a separate tumor organoid and may be used to assess T-cell homing to tumor cells through fluid (e.g., microfluidic) circulation. In vivo tumor-infiltrated lymphocytes (TILs) can exist that can initiate a response under immunotherapy, but these are not active in all tumors. As such, often the primary immune response under immunotherapy comes from the lymph node via the circulation. In some embodiments, a device of the present invention may be used to assess the capabilities of immune cells to home to a tumor organoid in the device from an upstream immunology organoid and/or to assess T-cell activation and/or tumor killing. In some embodiments, white blood cells may be infused into the device, optionally when nodal tissue and/or the number of lymph node cells is insufficient.

By providing a device that pairs patient-specific biopsy-derived tumor organoids with immune cells (e.g., lymph node cells) and/or organoids comprising such cells from the same patient, e.g., a genetically matched human immune system can be provided into tumor organoids. This device may be used to screen immunotherapy agents and may be performed on a patient-by-patient basis. In some embodiments, a device and/or method of the present invention may reduce the likelihood of error and/or false positives and/or negatives since, for example, multiple samples can be tested.

In some embodiments, a method of the present invention may comprise activating an immune cell ex vivo, the method comprising: contacting an immune cell (e.g., a lymphocyte) to a live tumor cell organoid comprising a plurality of live tumor cells to provide an activated immune cell; isolating the activated immune cell from the live tumor cell organoid to provide an isolated activated immune cell; and propagating the isolated activated immune cell to provide a population of activated immune cells. Any type of immune cell such as, e.g., those described herein, may be contacted to the live tumor cell organoid. In some embodiments, the immune cell(s) may be unpassaged cells (e.g., unpassaged cells obtained from a patient) and/or the tumor cell(s) used to form the live tumor cell organoid may be unpassaged cells (e.g., unpassaged cells obtained from a patient). In some embodiments, immune cells and/or tumor cells may be passaged 0, 1, 2, 3, or 4 times or more. In some embodiments, the immune cells comprise peripheral blood mononuclear cells. Thus, in some embodiments, a tumor organoid as described herein and a patient's own lymphocytes may be used to treat cancer. For example, for a patient with melanoma, the method may comprise contacting the patient's lymphocytes with tumor organoids produced and/or formed with his own melanoma cells or their products, activate the patient's lymphocytes ex vivo with or without drugs, then collect the activated lymphocytes, expand their population, and administer them to the patient. One or more steps of the method to activate an immune cell ex vivo can be repeated one or more times (e.g., as many times or as long as the cells in the organoids remain alive). In some embodiments, the method may be performed for the patient with cells from a new tumor recurrence.

In some embodiments, an activated immune cell may be an immune cell with adaptive immunity (e.g., a T cell with adaptive immunity) and/or an immune cell with immunologic memory (e.g., a T cell with immunologic memory) obtained from ex vivo exposure to a patient's own tumor antigens. In some embodiments, a primed and/or activated immune cell may be primed and/or activated responsive to exposure to a drug. In some embodiments, a method of activating an immune cell ex vivo may comprise using the white blood cell fraction from a blood draw of patient containing the patient's lymphocytes (T cells), then contacting the patient's lymphocytes with his or her own tumor cell organoids or their secreted products, which would activate the lymphocytes ex vivo with or without drugs, and then collect the activated lymphocytes (e.g., T cells). In some embodiments, contacting the patient's lymphocytes with his or her own tumor cell organoids or their secreted products may be in the presence of one or more drug(s), which may increase activation potential of the lymphocytes. The activated lymphocytes may be infused back to the patient and optionally expanded in vitro prior to infusion. The method of activating an immune cell ex vivo may provide for activation of T cells outside the patient and/or may spare a patient from unnecessary drug toxicity. In some embodiments, the method of activating an immune cell ex vivo may activate more cells than just those localized near the tumor cells and/or tumor organoid.

Referring to FIG. 11, a device of the present invention may comprise one or more chambers that may be connected by one or more parallel channels that may be daisy chained together with each of the one or more chambers comprising an organoid (e.g., a tumor organoid) (FIG. 11A), which may increase the number of organoids (e.g., the patient tumor organoids (PTOs) number) per circulator path. In some embodiments, two or more organoids may be present and/or patterned in the same chamber (FIG. 11B). In some embodiments, one or more T cells may be infused and/or circulated in a device and/or method of the present invention such as shown, e.g., in FIG. 11C, which may induce priming and/or activation of the T cells in response to tumor antigen recognition. The circulating T cells may be removed and/or transferred from the device after a period of time. In some embodiments, the removed circulating T cells may be contacted to unexposed matched patient tumor organoids (e.g., non-immune enhanced tumor organoids) such as, e.g., to test activation levels and/or tumor killing. In some embodiments, the primed and/or activated T cells may be administered to a subject/patient.

In some embodiments, a method and/or device of the present invention may provide and/or allow for parallel screening of two of more (e.g., 2, 3, 4, 5, 6, 7 or more) compounds of interest. In some embodiments, at least one of the two or more compounds of interest is an immunotherapy drug.

In some embodiments, a method and/or device of the present may provide and/or allow for results (e.g., drug screening results and/or therapeutic analysis) within about 1 or 2 weeks (e.g., within about 2, 3, 4, 5, 6, 7, 8, 9, or 10 days) after a biopsy (e.g., a lymph node and/or tumor biopsy) from a subject is obtained, the cells of which were used to prepare an organoid of the present invention that was used in the method and/or device. In some embodiments, a method of the present invention comprises treating a subject, optionally with a compound of interest, within about 1, 2, or 3 weeks (e.g., within about 2, 3, 4, 5, 6, 7, 8, 9, 10, 11, 12, 13, or 14 days) after the biopsy (e.g., a lymph node and/or tumor biopsy) from the subject is obtained, optionally responsive to obtaining the results (e.g., drug screening results and/or therapeutic analysis) obtained with cells from the biopsy.

Also described herein is a device useful for evaluating immune cells and/or tumor cells in vitro, including: (a) a microfluidic device having a chamber, and a channel in fluid communication with the chamber; (b) at least one organoid (e.g., an organoid comprising immune cells and/or tumor cells) in the chamber; (c) a growth media in the chamber and the channel; (d) a pump operatively associated with the chamber and channel and configured for circulating the media from the chamber through the channel and back to the chamber; and (e) a microporous membrane (e.g., a TRANSWELL® microporous membrane) in the channel and positioned so that the media flows therethrough. A device of the present invention may be kept under circulating flow and/or intermittent flow, optionally at a flow rate of about 1, 2, or 5 µL/min to about 7, 10, 15, 20, 25, 50, 100, 150, 200, 250, 300, 350, 400, 450, or 500 µL/min. In some embodiments, intermittent flow may be used to decrease interstitial flow inside an organoid, optionally when migration is being examined and/or determined for cells to and/or from the organoid. In some embodiments, intermittent flow may be utilized to stimulate drug administration (e.g., infusion) in vivo. In some embodiments, the device is configured and/or amenable to analytical investigation such as, but not limited to, biochemical assays and direct imaging on a chip. According to some embodiments, cells (e.g., immune cells) may be infused into a device of the present invention optionally at a flow rate of about 1, 2, or 5 µL/min to about 7, 10, 15, 20, 25, 50, 100, 150, 200, 250, 300, 350, 400, 450, or 500 µL/min. In some embodiments, the flow rate of a device of the present invention and/or rate of infusion of cells may be about 1, 2, 3, 4, 5, 6, 7, 8, 9, 10, 11, 12, 13, 14, 15, 16, 17, 18, 19 or 20 µL/min.

In some embodiments, the device is useful for screening a compound of interest in vitro for immunological activity and/or for activity in modulating the immune system and/or activity thereof. In some embodiments, the device is useful for evaluating metastasis of tumor cells in vitro, for evaluating tumor cell migration and/or invasion in vitro, for evaluating growth of a construct comprising tumor cells in vitro, and/or for evaluating response to a compound of interest. In some embodiments, the device may be useful for evaluating construct size in vitro, the number of tumor cells in vitro and/or tumor cell death in vitro.

In some embodiments, a method of the present invention may determine at least one tumor organoid response (e.g., tumor cell viability, cell number, volume, apoptosis, etc.), at least one immune cell activity, the activation or depletion of at least one marker (which may be assessed by immunofluorescent biomarkers) and/or the presence of at least one T cell activation marker and/or T cell dysfunction marker. In some embodiments, a method of the present invention may comprise determining nodal cell migration, optionally via live cell tracking. Efficacy of a test compound may be determined by: viability of cells (LIVE/DEAD), number of viable cells, number of viable cells versus dead cells, mitochondrial metabolism (MTS), LDH quantification (positive in tumor cells), and/or IHC (e.g., Annexin V vs. KI67-apoptotic vs. proliferative markers).

In some embodiments, a method of the present invention may be used to monitor in vitro the efficacy and/or tumor death rate inflicted by engineered immune cells such as, e.g., CAR T cells, and/or may be used to calculate the appropriate dose and/or infusion rate of the engineered immune cells (e.g., CAR T cells), optionally to prevent complications for a patient based on efficacy and volume of disease.

Provided according to some embodiments of the present invention is a method of screening a compound of interest in vitro for immunological activity and/or modulating the immune system, the method comprising: providing at least one organoid comprising a plurality of cells (e.g., optionally wherein the at least one organoid is a liver organoid, heart organoid, tumor organoid, immunology organoid, mixed organoid, etc.); contacting the compound of interest to the at least one organoid in vitro; and, responsive to contacting the compound of interest to the at least one organoid in vitro, determining an immunological response of the at least one organoid (e.g., as compared to the immunological response/activity of the organoid prior to and/or in the absence of contact with the compound of interest). In some embodiments, the at least one organoid is a tumor organoid and a separate organoid comprising immune cells. In some embodiments, the at least one organoid is an organoid comprising tumor cells and immune cells. In some embodiments, the at least one organoid is a mixed organoid (e.g., a mixed symbiotic organoid).

In some embodiments, a method of the present invention comprises contacting the at least one organoid with a culture medium. In some embodiments, the culture medium comprises at least one type of immune cell, optionally white blood cells, and the at least one type of immune cell may be from the same source as the cells in the at least one organoid. In some embodiments, the culture medium comprises a compound of interest.

A method of the present invention may comprise determining cell migration (e.g., determining migration of at least one type of immune cell), optionally using live cell tracking. In some embodiments, a method of the present invention comprises determining the presence of activation and/or depletion markers on cells (e.g., migrating cells and/or cells present in the organoid), optionally using immunofluorescence. In some embodiments, a method of the present invention comprises, responsive to contacting the compound of interest to the at least one organoid in vitro, the compound of interest activates and/or increases the immunological activity of the least one type of cell (e.g., an immune cell). In some embodiments, a method of the present invention comprises, responsive to contacting the compound of interest to the at least one organoid in vitro, there is a decrease in growth of cells (e.g., tumor cells) present in at least one organoid (e.g., lack of proliferation of cells, death of the cells, decrease in invasion of cells, etc.). When the at least one organoid comprises tumor cells, a method of the present invention may comprise, responsive to contacting the compound of interest to the at least one organoid in vitro, determining a decrease in growth of tumor cells present in at least one organoid (e.g., lack of proliferation of cells, death of the cells, decrease in invasion of cells, etc.). In some embodiments, determining a decrease in growth of live tumor cells comprises determining the number of viable tumor cells in the at least one organoid, determining the number of live tumor cells present in the at least one organoid, determining the volume of the at least one organoid, and/or determining the number of dead tumor cells present in the at least one organoid.

In some embodiments, a method of the present invention comprises calculating a dosage and/or infusion rate of the compound of interest to administer a subject. In some embodiments, a method of the present invention comprises, responsive to contacting the compound of interest to the at least one organoid in vitro, administering the compound of interest to a subject in a treatment-effective amount, optionally when the compound of interest is determined to decrease the metastasis of the tumor cells in vitro, decrease organoid size in vitro, decrease the number of tumor cells in vitro, induce tumor cell death in vitro, increase activity of an immune cell in vitro, and/or activate an immune cell in vitro.

In some embodiments, a device useful for evaluating tumor cells and/or immune cells in vitro comprises one or more (e.g., 1, 2, 3, 4, 5, 6, 7, 8, 9, 10, or more) chambers with at least one organoid in each chamber and being in fluid communication with one another. The device may be useful for evaluating immunological activity, modulating the immune system and/or an activity thereof, metastasis of tumor cells in vitro, for evaluating tumor cell migration and/or invasion in vitro, for evaluating growth of a construct comprising tumor cells in vitro, and/or for evaluating response to a compound of interest. In some embodiments, the device may be useful for evaluating construct size in vitro, the number of tumor cells in vitro and/or tumor cell death in vitro. The one or more organoids present in the device may be prepared from cells obtained from a single subject. In some embodiments, the device comprises a live tumor cell organoid in a first chamber and an organoid comprising immune cells in a second chamber. In some embodiments, the device comprises a live tumor cell organoid and an organoid comprising immune cells in the same chamber, optionally separated from each other such as, e.g., shown in FIG. 2. In some embodiments, when two or more organoids are provided in the same chamber, the cells of the organoids and/or the organoids may be present in one or more (e.g., 2, 3, 4, 5 or more) zones and/or areas of the chamber. For example, in some embodiments, a chamber comprises two or more zones and/or areas and cells of one organoid (e.g., an immune cell organoid) may be present in a first zone and/or area and cells of a second organoid (e.g., a tumor cell organoid) may be present in a second zone and/or area, such as, e.g., shown in FIGS. 4A-4C. Having different cells and/or organoids in the same chamber, but in different zones and/or areas that are optionally adjacent to one another may provide and/or force migration of cells through an organoid, but may not provide and/or force migration of cells through circulation. The live tumor cell organoid and liver organoid may be formed from cells obtained from the same subject, which may provide a personalized analysis.

In some embodiments, the device may comprise: a primary chamber comprising a live tumor cell organoid; at least one secondary chamber comprising a different organoid; at least one primary conduit connecting the primary and secondary chambers and providing fluid communication (e.g., such as the flow of a growth media) therebetween; and optionally a growth media in the primary chamber, each secondary chamber, and the primary conduit. In some embodiments, two or more (e.g., 2, 3, 4, 5, 6, 7, 8 or more) secondary chambers are provided with each secondary chamber comprising an organoid comprising different cells than another. In some embodiments, the at least one secondary chamber comprises a liver organoid, optionally wherein the live tumor cell organoid and liver organoid are prepared from cells obtained from the same subject. Additional example devices include, but are not limited to, those described in PCT/US2016/054611 and PCT/US2017/045277, the contents of each of which are incorporated herein by reference in their entirety.

In some embodiments, at least a portion of the device (e.g., microfluidic device) is transparent, and the device may comprise a detector (e.g., a camera) operatively associated with a microporous membrane and configured for detecting (e.g., imaging) cells (e.g., tumor and/or immune cells) on the microporous membrane.

The device body may itself be formed of any suitable material or combination of materials. Examples include, but are not limited to, polydimethylsiloxane (PDMS), polystyrene, polymethyl methacrylate (PMMA), polyacrylamide, polyethylene glycol (PEG) including functionalized PEG (e.g. PEG diacrylate, PEG diacrylamide, PEG dimethacrylate, etc., or any of the foregoing PEGs in in multi-arm forms, etc.), natural polymers or proteins that can be cross-linked or cured (e.g., hyaluronic acid, gelatin, chondroitin sulfate, alginate, etc., including derivatives thereof that are functionalized with chemical groups to support cross linking, and including any of the "cross-linkable prepolymers" described above in cross-linked form, and combinations thereof. The device body may be formed by any suitable process, including molding, casting, additive manufacturing (3d printing), lithography, etc., including combinations thereof.

Where a structural support is included in the device, that structural support, like the hydrogel, may be patterned (e.g., a regular or irregular pattern, such as a regular or irregular lattice, grid, spiral, etc.).

In some embodiments, a device of the present invention, which may be used in a method of the present invention, may be configured to provide a physiological or hyperphysiological fluid to tissue volume ratio. For example, one or more chambers in the device may have an average volume in a range of about 2 μL to about 10 μL. In some embodiments, one or more chambers in the device may have an average volume of about 2, 3, 4, 5, 6, 7, 8, 9, or 10 μL. In some embodiments, a device of the present invention (e.g., a device comprising at least 2 or 6 chambers) may use liquid in the amount of and/or have a volume of less than about 100 μL, such as, e.g., about 95, 90, 85, 80, 75, 70, 65, 60, 55, 50, 45, 40 μL or less. The volume of the device, as used herein, refers to the volume to fill the chamber(s) and channel(s) of the device. In some embodiments, a device of the present invention (e.g., a device comprising at least 2 or 6 chambers) may use liquid in the amount of and/or have a volume of less than about 50 μL. In some embodiments, the volume of the device may be increased by integration and/or use with an external fluid reservoir. The external fluid reservoir may increase the overall system volume and/or aid in controlling the volume of the device.

A system, device, and/or method of the present invention may comprise and/or provide one or more (e.g., 1, 2, 3, 4, 5, 6, 7, 8, or more) different tissues and/or organoids that each are viable for at least 1, 2, 3, 4, 5, or more weeks. In some embodiments, a system, device, and/or method of the present invention comprises and/or provides one or more (e.g., 1, 2, 3, 4, 5, 6, 7, 8, or more) different organoids that are in fluid communication with each other and a common aqueous growth media, and that are each viable for at least 1, 2, 3, 4, 5, or more weeks. Thus, in some embodiments, two, three, four, five, six, or more different organoids are in fluid communication with each other and a common aqueous growth media, and each is viable for at least 1, 2, 3, 4, 5, or more weeks. In some embodiments, one or more of the organoids may be viable and may comprise at least about 75% or more (e.g., about 80%, 85%, 90%, 95% or more) living cells based on the average number of cells present in the construct at 1, 2, 3, 4, 5, or more weeks. The tissues and/or organoids may be generated by differentiation from a common cell sample (e.g., a sample such as a skin sample collected from a subject). One or more of the organoids may comprise cells in proportions similar to the proportions of cells present in the corresponding native (e.g., human) tissue. In some embodiments, at least one of the organoids comprises metastatic and/or malignant cells. In some embodiments, a function and/or property of the tissue and/or organoid may be determined and/or measured and compared to the function and/or property of a corresponding native tissue (e.g., a property of a brain organoid may be measured and compared to the same property of a brain tissue in a subject). In some embodiments, a function and/or property of the tissue and/or organoid may be similar to the function and/or property of a corresponding native tissue.

As described herein, cells and/or a cell sample may be used in a method of the present invention to form an organoid of the present invention. Methods of the present invention can provide a viable organoid. In some embodiments, a method of the present invention can achieve a take rate of at least 50% or more such as, e.g., about 50%, 55%, 60%, 65%, 70%, 75%, 80%, 85%, 90%, 95%, 98%, or more. For example, a 90% take rate means that 90% of the time a viable organoid or plurality of organoids (e.g., an organoid set) is achieved and/or provided by a method of the present invention. That is, for a 90% take rate, 9 out of 10 cell samples (e.g., tumor cell samples) yield a viable organoid or plurality of organoids when prepared according to a method of the present invention. The organoid or plurality of organoids may be used in another method of the present invention and/or diagnostics. In some embodiments, the cells and/or cell sample may be from a tumor, such as, e.g., a mesothelioma biospecimen and/or a GI tumor biospecimen and/or from a lymph node biopsy.

A method of screening a compound of interest in vitro for anti-metastatic activity and/or anti-tumor activity may be carried out by: providing a device comprising at least one organoid comprising tumor cells as described herein; circulating media in the device; administering a compound of interest to the tumor cells (e.g., by adding the compound to the media); and quantitatively or qualitatively detecting tumor cells captured on a microporous membrane, where a lesser number of tumor cells captured (e.g., as compared to other tumor cells under like conditions, and/or non-metastatic cells under like conditions) indicates greater anti-metastatic activity and/or anti-tumor activity of the compound of interest. In some embodiments, at least one type of immune cell may be present in the device (e.g., in the media, in the at least one organoid comprising tumor cells and/or in an organoid in a chamber of the device).

A method of screening a compound of interest in vitro for anti-metastatic activity and/or anti-tumor activity may be carried out by: providing a device as described herein (e.g., a device comprising a primary chamber comprising a live tumor cell organoid and at least one secondary chamber); circulating media in the device; administering a compound of interest to the tumor cells (e.g., by adding the compound to the media); and quantitatively or qualitatively detecting tumor cells present in one or more of the secondary chamber(s) (e.g., optionally on and/or in an organoid present in a secondary chamber), where a lesser number of tumor cells present in one or more of the secondary chamber(s) (e.g., as compared to other tumor cells under like conditions, and/or non-metastatic cells under like conditions) indicates greater anti-metastatic activity and/or anti-tumor activity of the compound of interest. In some embodiments, at least one type of immune cell may be present in the device (e.g., in the media, in the at least one organoid comprising tumor cells and/or in an organoid in a chamber of the device).

A method of the present invention may comprise labeling cells (e.g., tumor cells and/or immune cells) with a detectable compound, such as, but not limited to, a fluorescent compound (e.g., dye, protein, etc.).

The foregoing and other aspects of the invention are explained further in the following examples.

EXAMPLES

Example 1—Integration of Lymph Node and White Blood Cell Components within Fresh Patient-Derived Lung TOC Models to Test Immunotherapy (IT) Drug Efficacy In Vitro Integrated tumor and lymph node organoid biofabrication: Node cells and white blood cells will be labeled through membrane-incorporating dyes (PKH26-red or PKH67-green) and integrated with tumor biospecimen cells. Following biofabrication, presence of immune cells will be confirmed by staining for immune cell surface markers and verifying co-localization with the membrane dyes described above. Controls will consist of tumor organoids only.

PD-L1 and CTLA-4 assessment: Following tissue collection, immunohistochemistry (IHC) will be performed on a portion of each tumor biopsy using PD-L1 antibodies or on node biopsies using CTLA-4 antibodies. Each will be classified as high- or low-expressing, using an established 5% threshold value to define high-PD-L1 or CTLA-4 expression, allowing hypotheses to be generated for each biospecimen regarding IT susceptibility.

Immunotherapy drug panel compilation: Organoids can be made arbitrarily small in volume, thereby creating nearly any number of organoids for drug screens (and permutations) and biomarker identification. Pembrolizumab (pembro) targets the PD-1 receptor. Nivolumab (nivo) targets the PD-1 receptor, generally used if a cancer does not have BRAF mutations. Ipilimumab (ipi) activates the immune system by targeting CTLA-4.

Figure 1B:
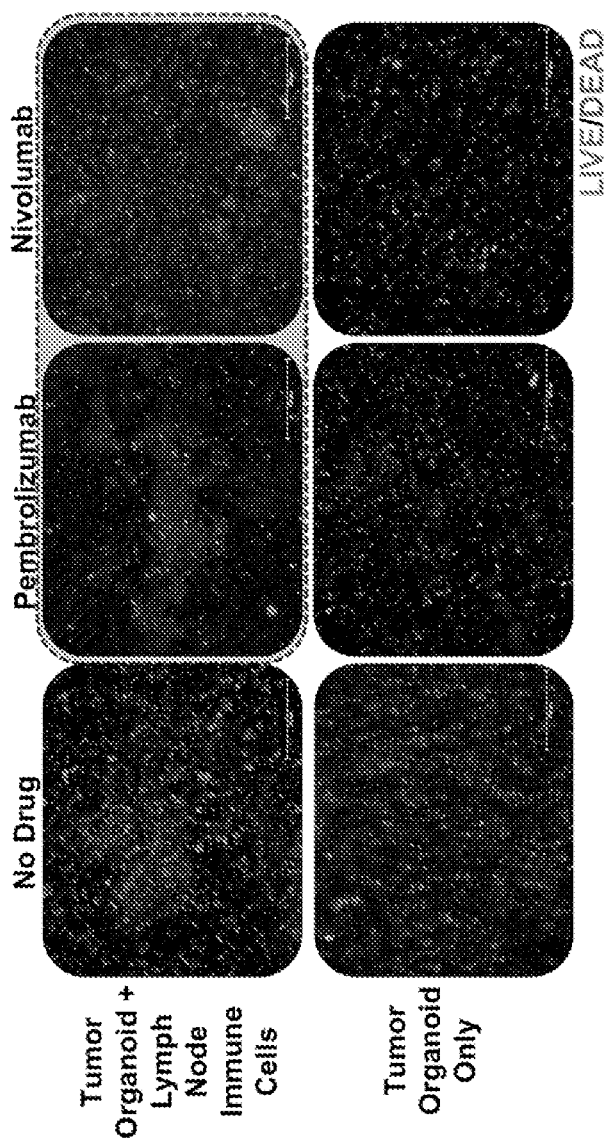
Figure 1C:
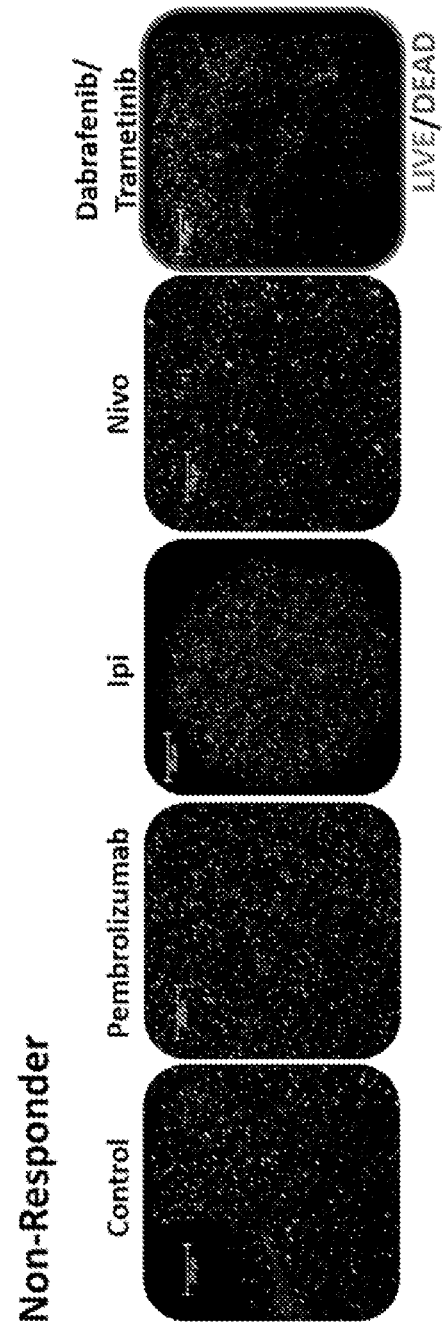

Drug screen output metrics: Drugs will be administered for 48 hours, after which efficacy will be determined as follows; specifically, viability of cells will be assessed by (LIVE/DEAD), number of viable cells alone, number of viable cells versus dead cells, mitochondrial metabolism (MTS), LDH quantification (positive in tumor cells), and IHC (colocalization of fluorescently labeled immune cells with apoptotic, proliferative, and tumor cell markers). FIG. 1A shows data of integrated colorectal tumor-node organoids in which upon incubation with nivolumab, an increase in mitochondrial metabolism was observed, likely through T-cell activation, and LIVE/DEAD staining in similar low-grade appendiceal tumor-node organoids (FIG. 1B), in which increases in cell death under pembro and nivo treatments were observed. These results will be corroborated using biomarker analysis. In addition, FIG. 1C shows data from PTOs derived from a melanoma patient previously treated without response with pembrolizumab and ipilumimab ("Non-Responder"). LIVE/DEAD staining shows recapitulation of non-responsive phenotype, where organoids from these tumors also did not respond to these immune checkpoint inhibitors, but did respond to dabrafenib and trametinib (right-most panel). This was not expected given the BRAF wild status of the patient. Retrospectively, the patient was found to have a downstream MEK mutation that was bypassing his BRAF status. The alternative therapy was identified by PTO screen more than 4 weeks prior to genomic sequencing that verified a MEK mutation, thus qualifying the patient for trametinib. The patient began treatment with trametinib, a MEK inhibitor, and began responding successfully almost immediately.

Figure 2:
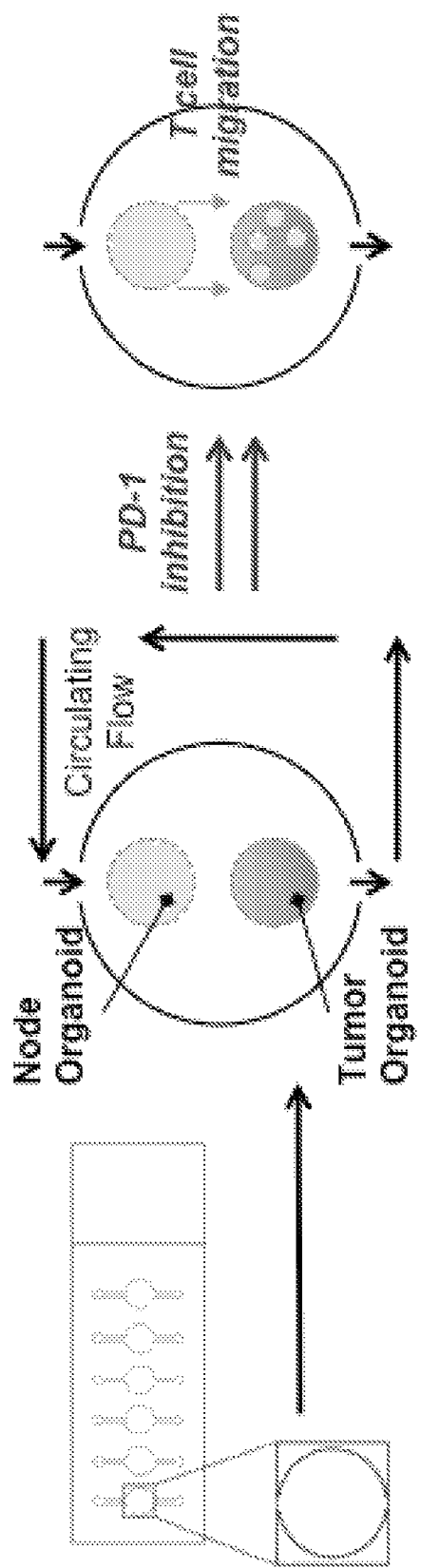
FIG. 2 shows an example 2-organoid system according to embodiments of the present invention.

Example 2—Implementation of a Lymph Node Organoid Upstream from the Tumor-On-a-Chip (TOC) to Assess T-Cell Homing to Tumor Cells Through Microfluidic Circulation 2-organoid biofabrication: A tumor organoid will be generated and a separate node organoid will be generated (in manner similar to Example 1, but without integration with the tumor cells) and placed in each chamber of a microfluidic device (FIG. 2). Alternatively, if no node organoid is included, then white blood cells will be infused through circulation. Controls will consist of tumor only.

Drug screen output metrics: Drug conditions and output will be similar as described in Example 1. In addition, verification of locations of immune cell numbers will be performed. The fluorescent tags will allow tracking and confirmation if immune cells can migrate to the downstream tumor in the presence of treatments and being exposed to tumor-associated antigens (FIG. 2). While not wishing to be bound to any particular theory, it is believed that conditions, such as PD-1 inhibition, may allow for immune cells such as T cells to now recognize the tumor cells, migrate to the tumor, and induce tumor cell death.

The microfluidic device architectures with PTOs biofabricated within each individual organoid channel/chamber will be employed as in FIG. 2. Additionally, PTO channels previously in parallel will be daisy-chained together so that all PTOs populate a single path through which T cells will be perfused (FIG. 11A), thus maximizing exposure to tumor antigens by T cells in circulation. PTO number per TOC can be significantly increased by photopatterning larger numbers of PTOs in a single larger chamber (FIG. 11B) or in multiple parallel channels to reduce system fluid volume.

Example 3—Introduction of Lymph Node Immune System Components to Test Immunotherapy Drug Efficacy as an in Fresh Patient-Derived Tumor-On-a-Chip Models Cells from pieces of resected lymph nodes, removed during time of tumor resection, will be incorporated into the patient-specific tumor-on-a-chip organoids, thereby facilitating screening of the effectiveness of immunotherapy agents to target the tumors. This approach reproduces native heterogeneity without the need to characterize particular cell populations. By using the total mixture of cells form a tissue sample (e.g., tumor cells, stromal cells, endothelial cells, etc.), the system is intrinsically representative of in vivo tumor heterogeneity. Responses will be compared to patient outcomes.

Biospecimen acquisition and processing: Patients will be predominantly consented and enrolled through the surgical practice for major abdominal visceral cancer resection or patients undergoing palliative procedures for resecting metastatic lesions and lymph nodes for local control purposes of resistant residual disease to ongoing immunotherapy. Not all patients will be required to have both components (tumor and lymph node) sampled. Sampling will be part of the clinically indicated procedure only. In other words, if the indicated surgery does not provide with access to both components (tumor and lymph node) then sampling will be performed only from accessible and present in the operating field structures. Fresh tumor biopsies will be minced, washed, digested, and filtered to yield cell suspensions. All specimens will be coded to prevent access to patient identity. Genetic profile data will be provided anonymously with the samples.

Microfluidic device fabrication: Conventional use of lithographically-defined polydimethylsiloxane elastomer for prototyping microfluidic devices can take days due to reliance on expensive transparency masks, photolithography for device definition, serial casting, and precise layer alignment. This presents a challenge to scale up and clinical translation. However, this approach is necessary only for extraordinary resolution (~1 μm). Our 3D systems will be fabricated using simple thin, patterned adhesive films that can be self-aligned and layered through folding to form microfluidic structures (FIG. 3A). Definition of chambers and channels is achieved through the use of a computer-controlled laser cutter. Using this platform, we have produced a number of complex devices, including valves, mixers, and other functional microfluidic systems.

Organoid-device integration: To address the challenges of integrating 3D organoids within a microfluidic system, we have developed a methodology for in situ biofabrication that utilizes a hyaluronic acid (HA) and gelatin-based hydrogel, HyStem, that has been employed extensively in tissue engineering, and in a variety of biofabrication techniques. In the general approach to fabricating tissue constructs, HA and gelatin/collagen components are mixed with tissue organoids, as well as a crosslinker and photoinitiator to support thiol-acrylate/methacrylate photopolymerization. Each cell suspension is added to the gel precursor at a density such that the ratios of organoid volumes in the final integrated construct match the volume ratios of organs in the human body (e.g., the mass of liver organoids is five times that of heart organoids.) Each cell-laden substrate is introduced to the microfluidic chambers sequentially and patterning is accomplished using a positive-tone photomask to define shape and location of constructs (FIG. 3B). The cross-linked hydrogel is adherent to the top and bottom surfaces of the chamber, allowing it to be retained under fluid flow conditions powered by a microperistaltic pump, which supports multiple circuits in parallel (FIG. 3C). This patterning can be performed in an arbitrary number of independent microfluidic chambers. The resulting 3D constructs can subsequently be kept under circulating flow with long-term viability, and the total system is amenable to analytical investigation, including both biochemical assays and direct imaging on-chip. This patterning can be performed in an arbitrary number of independent microfluidic chambers. The resulting 3D constructs can subsequently be kept under circulating flow with long-term viability, and the total system is amenable to analytical investigation, including both biochemical assays and direct imaging on chip. Additional patterning (e.g., with additional cell or organoid types) can also be used to produce multi-component structures, enabling significant system complexity. Notably, the hydrogel itself also supports incorporation of solubilized extracellular matrix, supplying additional biomolecular factors specific to each tissue organoid. ECM profiles differ between tissue types, inclusion of ECM components improves cell viability and function, and ECM components are easily linked into the hydrogel via covalent bonds or heparin-binding. Because the presence of specific matrix proteins (e.g., laminin, collagen I, collagen IV) and cytokines can effect tumor growth and migration and thus drug effectiveness, reproduction of these profiles in TOC devices ensures accurate recapitulation of the in vivo system. Overall, this fabrication approach is rapid, inexpensive, and modular, with straightforward potential to be mass-produced for a large number of parallel experiments.

Analytical Plan:

Sample Size and Power: The primary endpoint is the feasibility of the development of tumor organoids and tumor/lymph node organoids. This study will enroll 20 patients, with feasibility defined as the success rate of the organoid development. This rate will be expressed as the rate of (successful organoid development/20). This rate will be reported, along with the corresponding 95% confidence interval. With the planned sample size of 20, the width of the 95% confidence interval would be approximately +/−22.2% if the observed success rate was 50%.

Analysis of Primary Outcome: The primary outcome will be the rate of organoid development; this rate will represent the success of the organoid development.

Analysis of Secondary Outcome: The secondary outcome is the correlation of organoid chemosensitivity with individual response to chemotherapy (categorized into one of 3 groups: stable disease, partial response or no response). Given the small sample sizes in these 3 groups, a Kruskal-Wallis Test will be used to assess differences in the chemosensitivity observed in the 3 response groups.

Tumor-lymph node organoid biofabrication: The biofabrication methods described above will be utilized to create tumor-on-a-chip models specific to the patients from where the tissue was resected. In addition to the tumor biopsy-derived cells, cells isolated from the patients' lymph nodes will be combined with the tumor biospecimen-derived cells in the hydrogel organoid biofabrication process. Lymph node cells will be fluorescently labeled through membrane-incorporating dyes (PKH26-red or PKH67-green) and implemented in the following methods. To ensure immune cell proximity to tumor cells, we expect to combine the tumor cells and lymph node cells together in a 5:1 ratio by cell number, but this ratio may be adjusted. Following organoid biofabrication, presence of immune cells will be confirmed by staining for immune cell surface markers and verifying co-localization with the membrane dyes described above.

Immunotherapy drug panel compilation: Organoids can be made arbitrarily small in volume, thereby creating nearly any number of organoids for drug screens and biomarker identification. Interferons aid in helping existing immune cells fight cancer. Interleukin-2 aids in increasing the number of immune cells primed to fight cancer. Pembrolizumab targets the PD-1 receptor. Nivolumab also targets the PD-1 receptor, but is generally used if a cancer does not have BRAF mutations. Ipilimumab activates the immune system by targeting CTLA-4. Nivolumab/Ipilimumab, combination therapy. Vemurafenib/Cobimetinib targeting of tumors with BRAF mutations.

Drug screen output metrics: Efficacy of drug treatments will be determined as follows; Specifically, viability of cells will be assessed by (LIVE/DEAD), number of viable cells alone, number of viable cells versus dead cells, mitochondrial metabolism (MTS), LDH quantification (positive in tumor cells), and IHC (apoptotic vs. proliferative markers). In addition, verification of changes in immune cells numbers and state will be performed. Also, co-localization of labeled immune cells with tumor cells will be evaluated by imaging.

Drug efficacy correlation to patient response: Following drug screens and determination of which drugs are most effective for a given biospecimen organoid set, these data will be correlated to that of the patient, as described above using only de-identified data.

Statistical Analysis: Experiments will be performed in quadruplicate or greater; data will be presented as mean±standard error of the mean. Students t-tests will be employed for 2-group comparisons with $\alpha=0.05$. One-way ANOVA will be employed for multiple comparisons with confidence limits of 95% considered significant.

Example 4—Introduction of Patient-Matched Lymph Node Cell Populations into Patient Tumor Biospecimen Ex Vivo Tumor-On-a-Chip Organoids Biospecimen acquisition and processing: Patients will be predominantly consented and enrolled through our CRS/

HIPEC surgical practice for major abdominal visceral cancer resection or extremity tumor resections as well as stage IV melanoma patients undergoing palliative procedures for resecting metastatic lesions and lymph nodes for local control purposes of resistant residual disease to ongoing immunotherapy. Sampling will only be part of the clinically indicated procedure. In other words, if the surgery does not provide with access to both components (tumor and lymph node) then the patient will not be consented for these studies. Tissue and data from the Advanced Tumor/Tissue Bank Project (BG04-104), the IPHC Research Database (BG01-372), and precision medicine reports (genetic mutation analysis), when available, will also be used in this research. In general, aligning with our preliminary data, we expect to obtain colorectal, appendiceal, peritoneal mesothelioma, and melanoma tissue. All specimens are de-identified. Fresh biopsies will be minced, washed, digested, and filtered to yield cell suspensions. A portion of the nodal cells will be fluorescently labeled (QTracker probes) for tracking. Our goal is to create sets of organoids from 12 distinct specimens.

Microfluidic device fabrication: 3D systems will be fabricated using simple thin, patterned adhesive films that can be self-aligned and layered through folding to form microfluidic structures (FIG. 3A). Definition of features is achieved by a computer-controlled laser cutter.

Figure 4A:
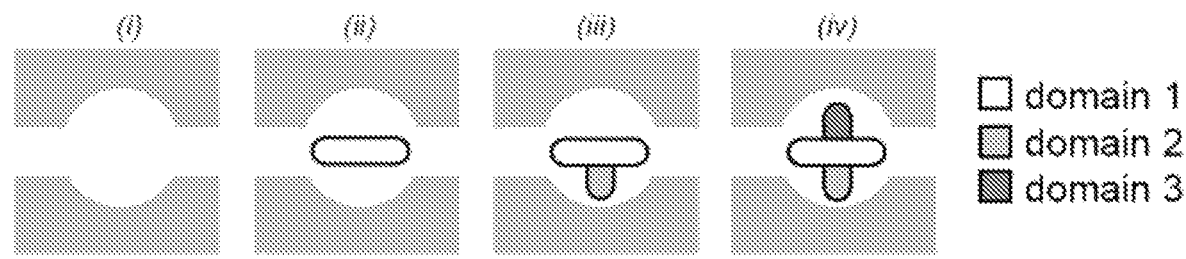
FIGS. 4A-4C are schematic illustrations of chambers including tumor cells and immune cells that are provided in separate, but adjacent zones, which may force cells to migrate towards one another for interaction according to embodiments of the present invention.
Figure 4B:
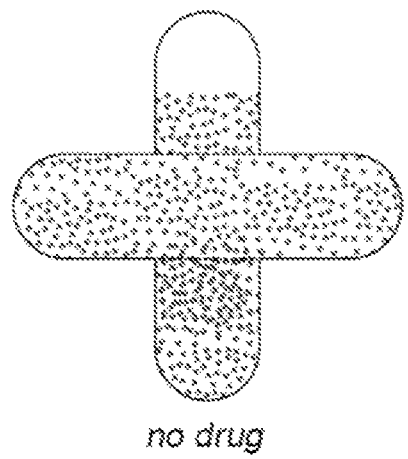
Figure 4C:
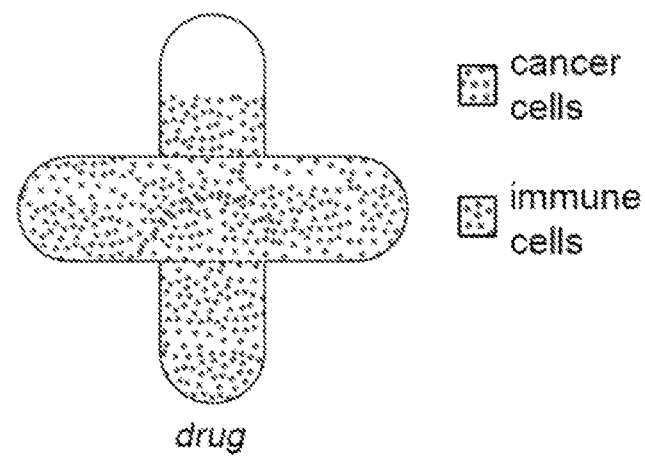

Organoid-device integration: HA and gelatin/collagen components are mixed with cells, as well as a crosslinker and photoinitiator for photopolymerization in situ. Cells are added to the gel precursor preferably at a density of 20 million cells/mL or higher, after which the cell-gel mixture introduced to the microfluidic chambers sequentially and patterning is accomplished using a positive-tone photomask to define shape and location of constructs (FIG. 3B). For the proposed studies, each device will contain series of 2 chamber circuits in which one chamber will be formed a tumor organoid and in the other will be formed a lymph node organoid. Alternatively, both organoids can exist separately, but in the same chamber (FIG. 2). In another form factor, tumor cells and immune cells can be photopatterned into the device as adjacent regions, in which for the immune cells to successfully target the tumor cells, they are forced to recognize tumor cell antigens, activate, and migrate to the tumor region. (FIGS. 4A-4C). The resulting 3D constructs are typically maintained under circulating flow at 10 µL/min with long-term viability.

Organoid characterization and baseline cell migration studies: Following platform initiation, TOC devices will be operated under flow for 1, 7, and 14 days. At these time points, organoids will be fixed for IHC analysis. Tumor organoids will be subjected to panels of markers dependent on tumor type (we have characterized organoids from each of the types described in the preliminary data). Node organoids (and potential lymphatic cells that may have migrated to the tumor organoids will be assessed using antibodies for CD8, CD4, CD45, CD25, FOXP3, 1-selectin, CD44, CTLA4, PD1 to identify lymphocytes/leukocytes, TRegs, effector type, differentiation, and negative feedback. While FACS could be used, IHC allows for spatiotemporal information within the 3D organoids. Data will be assessed initially in organoid tissue sections for initial screens, but at later points in 3D by whole mount macro-confocal microscopy (Leica LCS TSI). Cell migration will be assessed in a more nuanced fashion, using live fluorescence and tracking migration of labeled node cells.

Assessment of Patient-Specific Tumor Organoid Response to Immunotherapy Agents with and without Nodal Cell Populations.

Drug panel compilation: Drug screens will be performed and drug concentrations will be based on clinical plasma levels. In parallel to tumor+node TOCs, tumor-only TOCs will be run as controls. The drugs screened may be as follows:
i) Pembrolizumab, targets the PD-1 receptor.
ii) Nivolumab, targets the PD-1 receptor, but is generally used if a cancer does not have BRAF mutations.
iii) Ipilimumab (Ipi), activates the immune system by targeting CTLA-4.
iv) Nivolumab/Ipilimumab, combination therapy.
v) Vemurafenib/Cobimetinib, targeting of tumors with BRAF mutations.
vi) Imatinib, an antibody for tumors with activating mutations of C-KIT, a stem cell marker.
vii) Interferons and Interleukin-2, aiding in immune activation Lymphatic node cell activation and tracking: Activation of immune cell populations will be assessed using subsets of the IHC framework described above. Tracking of migrating fluorescent cells will be performed as described above. Quantitative changes in the kinetics of migration will be determined between the experiments for each set of patient TOCs.

Drug screen output metrics: Drug efficacy will be determined by: viability of cells (LIVE/DEAD), number of viable cells alone, number of viable cells versus dead cells, mitochondrial metabolism (MTS), LDH quantification (positive in tumor cells), and IHC (Annexin V vs. KI67-apoptotic vs. proliferative markers).

Figure 5:
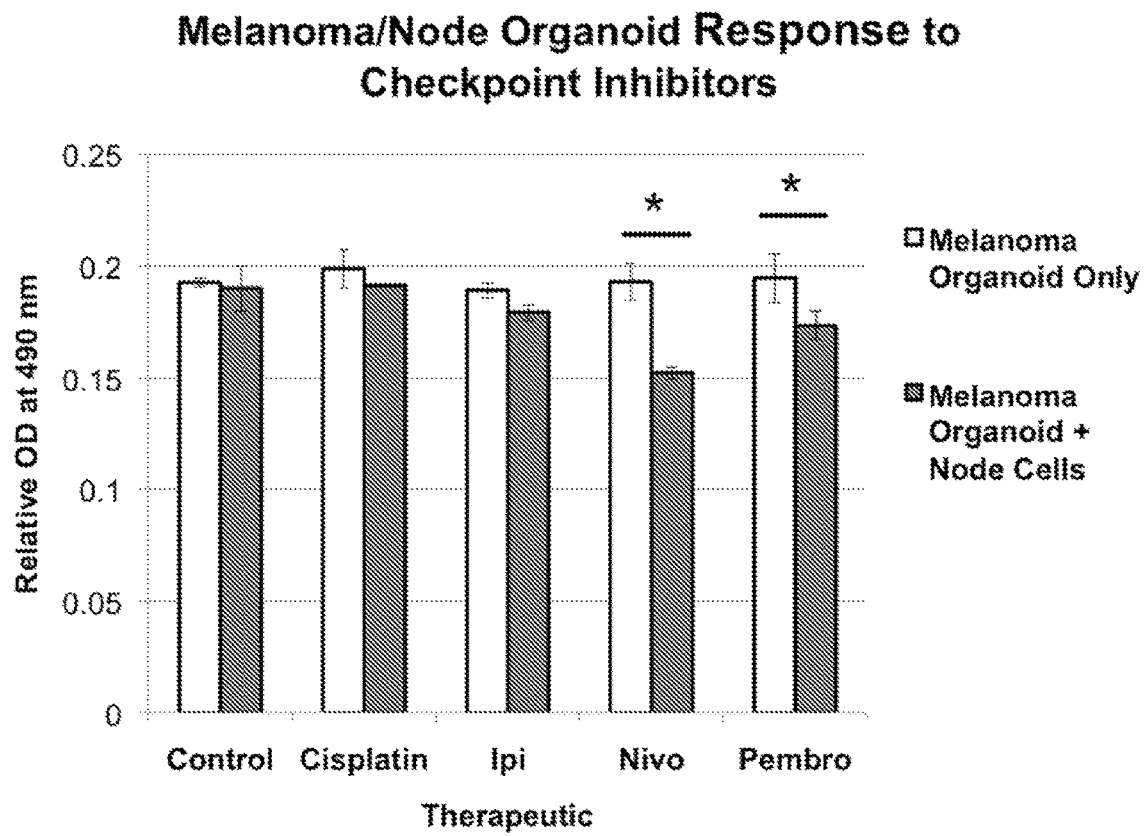
FIG. 5 is a graph showing the response of melanoma organoids and melanoma and lymph node organoids to various check point inhibitors.
Figure 6:
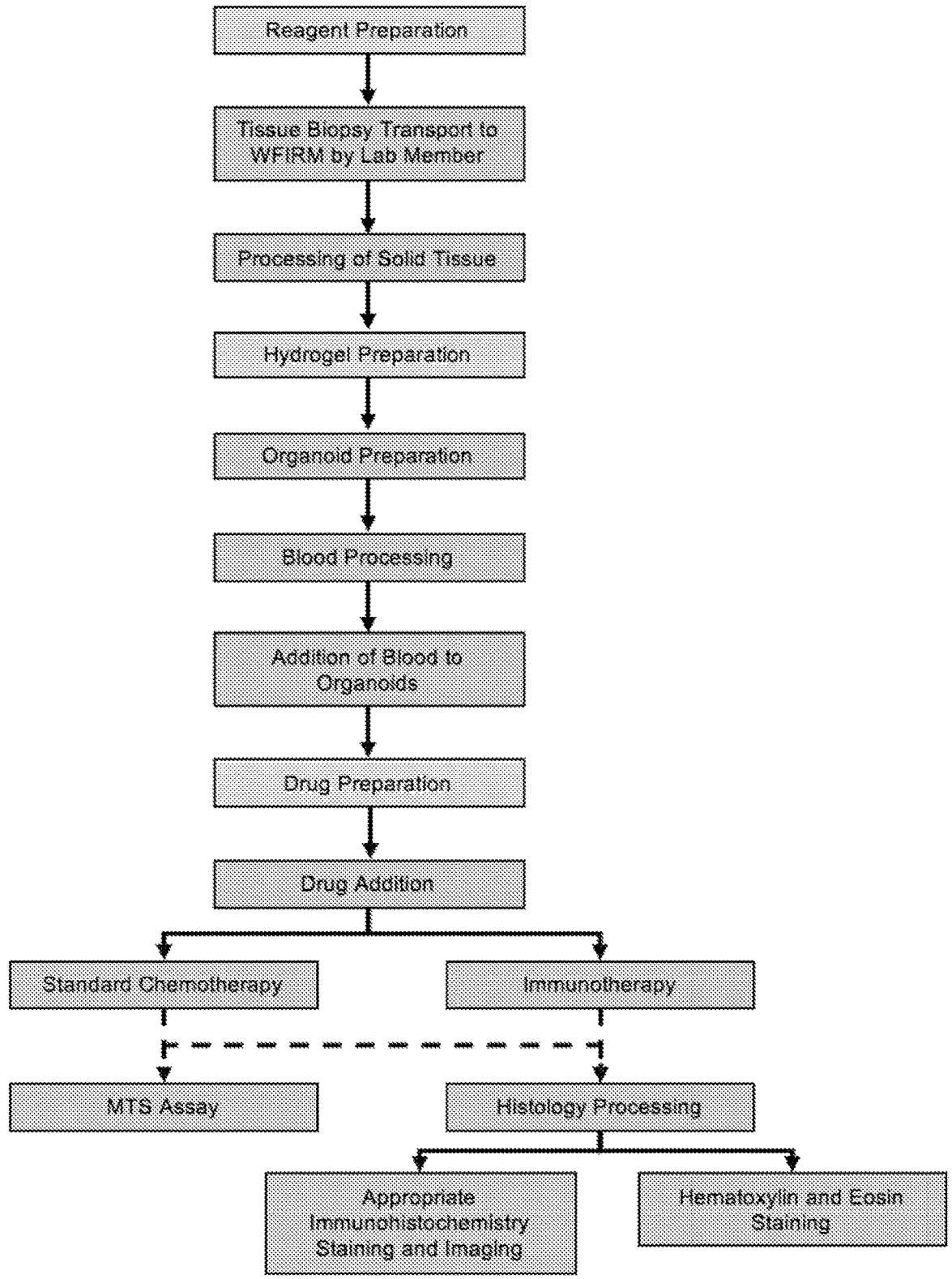
FIG. 6 shows an exemplary process diagram according to embodiments of the present invention.
Figure 7:
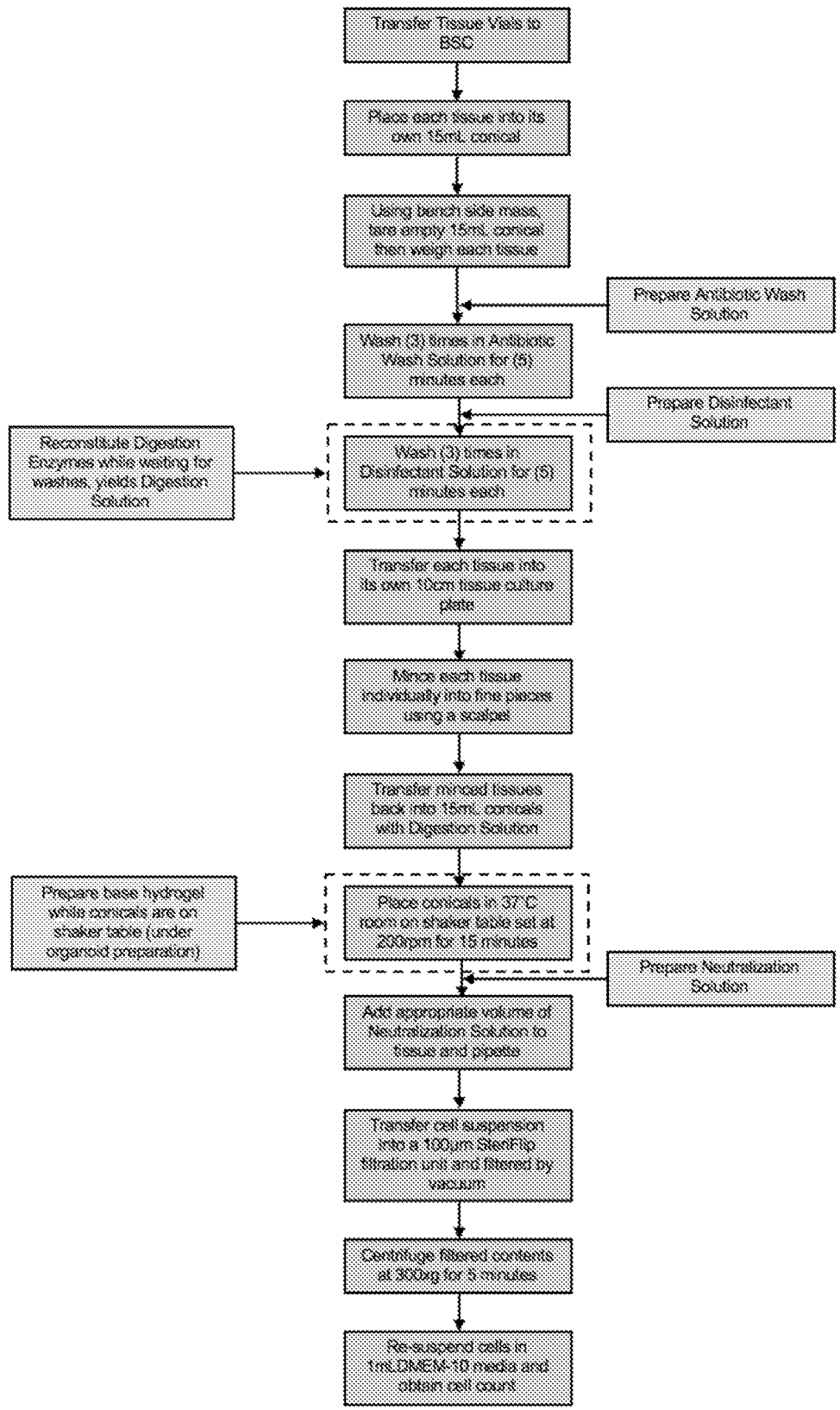
FIG. 7 shows an exemplary process for isolating cells from a solid tissue according to embodiments of the present invention.
Figure 8:
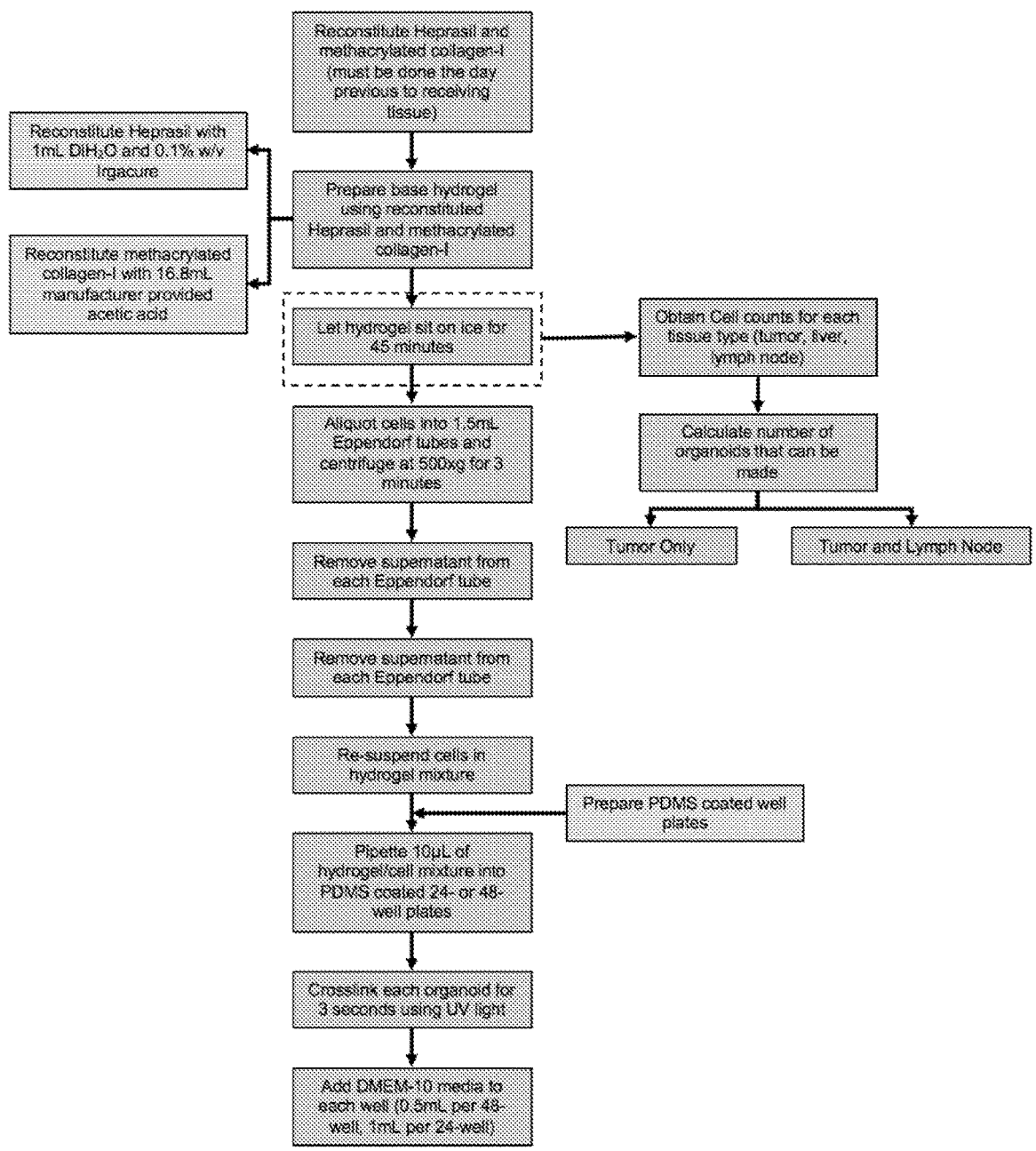
FIG. 8 shows an exemplary process for preparing organoids according to embodiments of the present invention.
Figure 9:
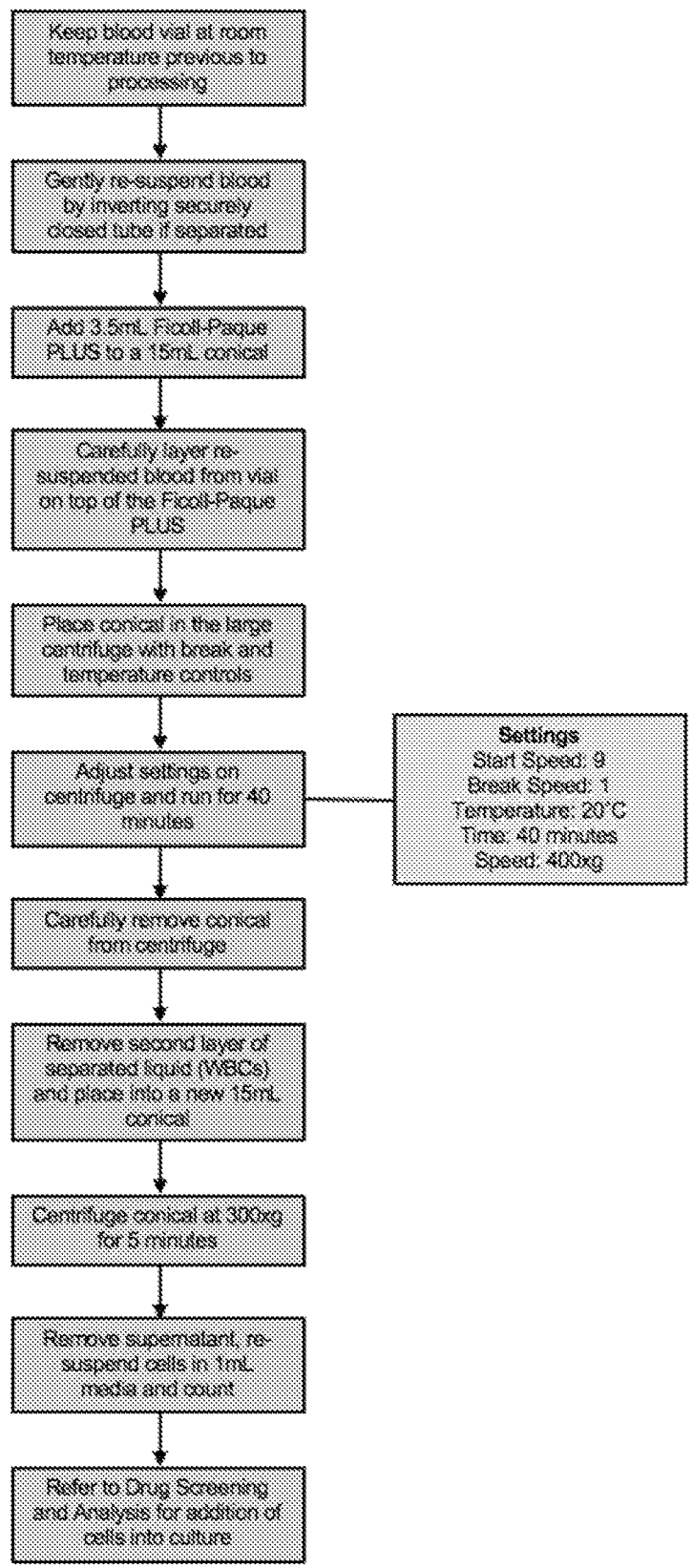
FIG. 9 shows an exemplary process for preparing white blood cells for addition to culture medium according to embodiments of the present invention.
Figure 10:
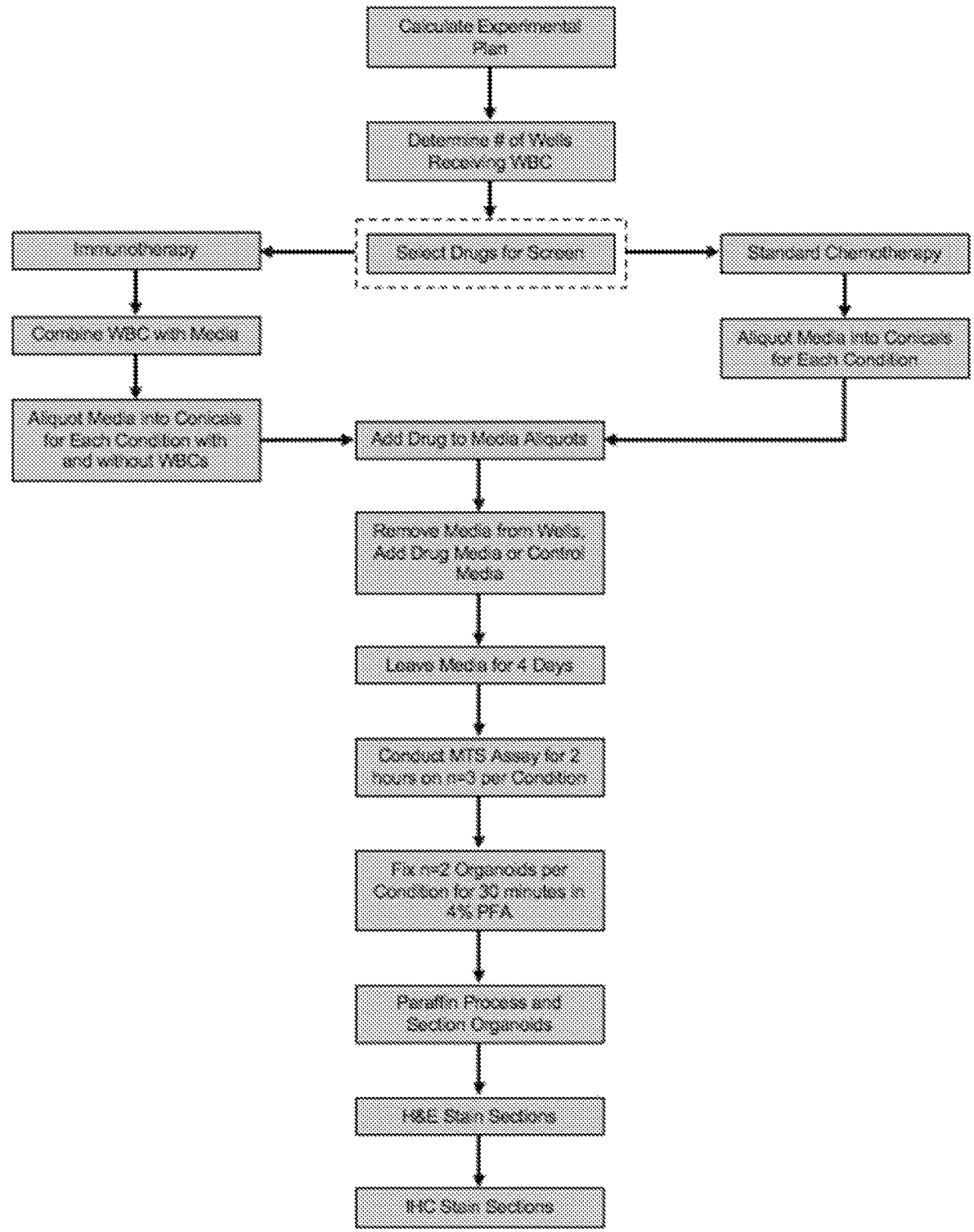
FIG. 10 shows an exemplary process for drug screening and analysis according to embodiments of the present invention.

FIG. 5 shows cell viability data for drugs screen with a melanoma tumor organoid and with a melanoma tumor organoid including lymph node cells. For the drug screens with the check point inhibitor nivolumab (nivo) or pembrolizumab (pembro), a significant decrease in organoid viability, measured by overall metabolic activity, was observed only when the organoid included both tumor cells and cells from the lymph node.

Example 5—Generation of Tumor and Related Tissue Organoids for Drug Screening and Disease Progression Analyses Biofabricated organoids made from patient tumors and related tissue will act as in vitro mimics of the in vivo microenvironment and immune system. Such mimics can be used for drug screens involving standard chemotherapies as well as immunotherapies by integrating the immune system and appropriate cells into the culture. Disease progression can additionally be studied using the constructs giving greater insight into patient specific tumor behavior for improved treatment.

The processes used in carrying out the methods of this example are illustrated in FIGS. 4-10. All operations involving an open container must be performed in a Bio-Safety Cabinet (BSC). Items being passed into BSC must first be cleaned with 70% EtOH via light spraying. Any excessive EtOH in BSC should be wiped up before carrying out procedures.

Cell culture vessels must be wiped with 70% EtOH prior to being placed in incubator or on the microscope. Excess EtOH should be wiped off before being placed into the incubator. Conical tubes contained cells will also be wiped or sprayed with 70% EtOH prior to being placed in the centrifuge.

Reagent Preparation

DMEM-10: Combine appropriate volume of fetal bovine serum (FBS) to Dulbecco's Modified Eagle's Medium (DMEM) to yield a 10% solution. Additionally, add the appropriate volume of penicillin/streptomycin and L-glutamine to yield 1% of each in solution. Sterile filter the combined medium through an appropriately sized media filter (500 mL, 1000 mL).

Digestion Solution: Add calculated volumes of reconstituted collagenase HA and BP Protease to low glucose DMEM (VitaCyte). Digestion solution must be used within 2 hours of reconstitution of enzymes.

Digestion Media Volume:

$$XX \text{ mg} \times \frac{20 \text{ mL digestion media}}{200 \text{ mg of tissue}}$$

Additions to Media:
- 6.6 μl/mL Collagenase HA×Volume of media to be prepared=Volume of Collagenase HA
  - Collagenase HA should be in a sterile vial, reconstituted in 20 mL of cold diH$_2$O and can be stored for 1 year
- 6.4 μL/mL BP Protease×Volume of media to be prepared=Volume BP Protease
  - BP Protease should be in a sterile vial, reconstituted in 2 mL of cold diH$_2$O and can be stored for 2 years DPBS Wash Solution: Add an appropriate volume of 10 mg/mL Gentamicin to DPBS in an appropriately labeled, sterile container to achieve a final concentration of 5 μg/mL Gentamicin. Swirl the solution to ensure adequate mixing. DPBS Wash Solution may be used up to 17 days after preparation.

Antibiotic Wash Solution: Add appropriate volumes of Amikacin (20 mg/mL final concentration), Amphotericin B (1 μg/mL final concentration), Gentamicin (5 μg/mL final concentration), and Vancomycin (5 mg/mL final concentration) to DPBS in an appropriately labeled, sterile container. Swirl solution to ensure mixing. Antibiotic Wash Solution is to be used the same day as prepared.

Digestion Neutralization Solution: Combine high glucose DMEM and with Fetal Bovine Serum (FBS) to have a final concentration of 10% FBS. Sterile filter and label appropriately. Swirl the solution to ensure mixing.

Digestion Neutralization volume: The volume of digestion neutralization media to be used should be equal in volume to the volume of digestion solution used to digest the tissue biospecimen.

Heprasil: Create a stock solution of UV photoinitiator by combining DiH$_2$O with 0.1% w/v Irgacure. Cover conical with tinfoil and place on shaker plate at 200 rpm in the 37° C. room for 30 minutes. Remove foil cap cover from Heprasil vial and add 1 mL of stock UV photoinitiator. Cover the vial and place in 37° C. incubator for 45 minutes.

Methacrylated Collagen-I: Remove foil cap cover from Methacrylated Collagen-I bottle. Add 16.8 mL of manufacturer provided Acetic Acid into the bottle to yield a 6 mg/mL concentration. Store bottle in 4° C. refrigerator and removed the appropriate volumes for each experiment.

Tool and Supply Preparation

PDMS Coated Plates: Using weight, combine Elastomer Curing Agent with Elastomer Base in a ratio of 1:10. Mix well with stirrer for 3-5 minutes. Use stirrer to drizzle a thin layer of PDMS into each well of 48- or 24-well plates. Gently rock plates to completely cover bottom of each well. Place plates into vacuum for 20 minutes. Remove from vacuum and place into 80° C. for a minimum of 2 hours. Once cured, previous to use with cultures, place plates under UV light in BSC for a minimum of 20 minutes.

Tweezers: Sterilize tweezers for use with tissue in a conical with 70% EtOH for a minimum of 30 minutes or autoclave.

1.5 mL Eppendorf Tubes: Place tubes in autoclave safe bags and seal, place autoclave tape on bag. Have autoclaved and use exclusively for tissue processing.

Cell Processing

Cell Isolation: Biopsied tissue is transferred into the BSC and washed three (3) times in prepared Antibiotic Wash Solution for 5 minutes each followed by three (3) washes of 5 minutes each in prepared Disinfectant Solution. While the tissue is being washed, digestion enzymes for tissue digestion solution are reconstituted. After washing, the tissue is transferred into an appropriately sized tissue culture dish and minced into fine pieces using scalpels. Once minced, the tissue is transferred into prepared Digestion Solution and placed in the warm room on the shaker table set at 200 rpm for 15 minutes. After digestion, an appropriate volume of Neutralization Solution is added to digested tissue and pipetted gently to mix. For the lymph node, use 100 μm centrifuge inserts and manually separate cells. The cell suspension is transferred into a 100 μm SteriFlip filtration unit and filtered by vacuum. The flow through is centrifuged at 300×g for 5 minutes. Supernatant is removed from the conical and cells are re-suspended in 1 mL of DMEM-10 and counted.

Preparation of Organoids: Heprasil is reconstituted and kept in the 37° C. incubator until combined with collagen. Methacrylated collagen-I is placed into a conical and neutralized using manufacturer's Neutralizing Solution at 85 μL per 1 mL methacrylated collagen-I while kept on ice. Heprasil is combined with methacrylated collagen at a ratio of 1:3 to produce the necessary volume as calculated for the number of organoids needed. Mixture is combined avoiding the introduction of bubbles and left on ice for 45 minutes. During the 45 minute wait, cells of each tissue type are counted (tumor, lymph node, liver) and aliquots are made in 1.5 mL Eppendorf tubes based on calculation. Tumor only, tumor and lymph node, and liver alone organoids should be made. Tumor and liver alone organoids should contain 10 million cells per mL with each organoid being 10 μL. Tumor with lymph node cells should contain 10 million cells per mL of tumor cells and 5 million cells per mL of lymph node cells. Eppendorf tubes with aliquots should be centrifuged at 500×g for 3 minutes. Supernatant should be removed from tubes and the appropriate volume of Heprasil/Methacrylated Collagen-I should be added to each. Re-suspend cells and then pipette them into each of the PDMS coated wells of the well plate. Crosslink each of the organoids using the UV light for 3 seconds each. Add DMEM-10 media as either 0.5 mL to each 48-well or 1 mL to each 24-well and incubate.

Preparation of White Blood Cells for Addition: Vial of blood should remain at room temperature until it is able to be processed. Previous to preparation, gently invert the vial to mix the blood so it is no longer separated if it has done so. Using a 15 mL conical, add 3.5 mL of Ficoll-Paque PLUS and then carefully layer the blood on top of the Ficoll layer, avoid mixing of the blood with the Ficoll. Place 15 mL conical into the large centrifuge that allows for setting personalization. Settings should be as follows: Start Speed—9, Break Speed—1, Temperature—20° C., Time—40 minutes, Speed—400×g. When centrifugation is complete, remove conical avoiding mixing or rocking of the separated layers. Using a pipette, remove the complete second layer of the separations and place into a new 15 mL conical. Add 3 mL of DMEM-10 to the conical and centrifuge for 5 minutes at 400×g. Remove supernatant and re-suspend cells with 1 mL of DMEM-10, count cells. Calculate how many wells can receive 25,000 cells per well.

Drug Screening and Analysis

Experimental Plan & Determining Wells with White Blood Cells (WBC): Determine how many organoids were made with tumor and lymph node cells and tumor alone cells. For each of these organoid types, divide by 5 to determine how many drug conditions can be carried out.

Immunotherapy Drug Selection: If lymph node or WBCs are present in culture, immunotherapies should be administered to n=5 wells per condition. Dose and time dependence should be considered with dose dependence taking priority. If prior treatment of immunotherapy has been administered, use that drug treatment as well as at least one other immunotherapy. Administer to with and without lymph node and with and without WBC. Use n=3 wells for MTS assay and n=2 wells for histology. If not studying time dependence, administer with no media changes for 4 days.

Standard Chemotherapy Drug Selection: On tumor only organoids, select standard chemotherapy treatments based on cancer origin and previous patient treatments. Dose and time dependence should be considered with dose dependence taking priority. If prior treatment of chemotherapy has been administered, use that drug treatment as well as at least one other chemotherapy. Use n=3 wells for MTS assay and n=2 wells for histology. If not studying time dependence, administer with no media changes for 4 days.

MTS Assay: Follow MTS assay instructions for preparing solution as given by the manufacturer, use high glucose DMEM without FBS for dilution. Remove media from each well and replace with 200 µL MTS assay diluted solution, do this to 3 empty, cell free wells to act as controls as well. Place plates back in incubator for 2 hours. Remove 100 µL of solution from each well and place into individual wells of a clear 96 well flat bottom plate. Use the plate reader to read absorbance of the wells at 490 nm.

Paraffin Processing and Sectioning: Organoids should be paraffin processed and sectioned in 5 µm thick layers with 4 sections per slide.

H&E and IHC Section Staining: H&E should be carried out on one slide of each condition to ensure cellularity of the organoids. IHC should additionally be carried out if cellularity is apparent. Selection of IHC should be determined based on cancer cell type and if lymph node or blood was also used in culture.

Example 6—Use of PTOs for Immune Cell Activation and Tumor Cell Killing Analyses Tumor biospecimen processing. Melanoma biospecimens will be obtained under IRB protocols of which both investigators on this project are members, and under which the data described in this proposal was generated. Each fresh biospecimen will be isolated in the clinic/operating room, placed in RPMI media in a sterile conical, and immediately transferred to the lab for processing. Biospecimens will be minced, washed, and incubated with collagenase/hyaluronidase to digest the major structural elements of the ECM. Portions will be preserved for histology. Organoids will be formed in a hydrogel including hyaluronic acid, gelatin, and a PEG crosslinker.

TOC PTO array design. Initially, the same microfluidic device architectures with PTOs biofabricated within each individual organoid channel/chamber as shown in FIG. 3 will be employed. PTO channels will be daisy-chained together so that all PTOs populate a single path through which T cells will be perfused (FIG. 11A), thus maximizing exposure to tumor antigens by T cells in circulation. However, should little activation or cell killing be observed, we will significantly increase PTO number per TOC by photopatterning larger numbers of PTOs in a single larger chamber (FIG. 11B) or in multiple parallel channels to reduce system fluid volume.

Post culture histological analysis. On day 7, each construct will be LIVE/DEAD stained and examined with confocal microscopy and unbiased segmentation to determine total cell viability. Directly following this, samples will be photobleached to remove LIVE/DEAD fluorescence and then sequentially labeled and imaged with a series of fluorescent antibodies (PNL2, HMB45, melan-A, CD4+, CD8+, PDL1, PD1, CD80/CD86, CTLA-4) to determine independently the location of melanoma cells and immune cell subtypes. To limit the number of sequential labeling/imaging cycles, we will group several spectrally-separated tags and perform multispectral imaging.

Immune cell perfusion/activation. We will test unsorted immune cells from lymph node biospecimens, which would save time and cost over FACS sorting for T lymphocytes. Moreover, this preserves the heterogeneity of the node-derived cells, of which several populations play roles. The first several biospecimen sets will be employed to determine how many PTOs are necessary to induce T cell activation, what length of time immune cells must be circulated in these TOCs to achieve sufficient activation, and whether immune checkpoint inhibitors are required. These factors will be determined utilizing the following methods and metrics for T cell state: As an assessment of T-cell function onboard TOCs, IFN-γ production in vitro will be determined in response to anti-CD3 plus anti-CD28 antibody (BD) and to commercially available (Proimmune Inc) peptide pools corresponding to melanoma antigens, gp100, MART-1, and tyrosinase. Conditions will be maintained for 96 hours. IFN-γ production will be assessed by ELISA (R&D Systems). T-cell proliferation will be measured by CFSE flow assay, measuring cytokines IFN-γ, IL-2 and TNFα. A suspension of organoid cells, harvested from the TOCs by non-enzymatic ECM dissolution or alternatively collagenase/hyaluronidase, will be analyzed by flow cytometry. Cells will be gated on CD3+, CD8+, and CD4+ to determine surface marker expression of CTLA-4, TIM-3, LAG3, PD-1, and CD160 which are associated with the T-cell "exhausted-like" phenotype. In another set of experiments organoids will be fixed and stained with anti-PDL-1 along with fluorescent staining of CD3+, CD4+, and CD8+ T cells to assess localization and interaction of T cells in relation to tumor cells, as described above. Sections will be assessed using multi spectra imaging with quantitative pathology with inForm analysis software.

Potential immune checkpoint inhibitor treatment. If necessary, we will expose TOCs to intermittent flow of 1 of 4 conditions: clean media, media with a clinically-relevant concentration of pembrolizumab, nivolumab, or ipililumab. Concentrations of these two widely-used PD-1 inhibitors and one widely-used CTLA-4 inhibitor will be derived from clinical treatment guidelines and scaled to the volume of the PTO. Currently ~100 nM concentrations have been employed, which appears to have no negative effect on the PTOs, unless they activate immune cells, causing user-intentional tumor cell death.

We will establish PTOs inside a microfluidic device. In construct formation, our goal will be to use unpassaged patient cells to avoid genetic alteration from in vivo tumor conditions. However, while not wishing to be bound to any particular theory, this may inherently limit the number of cells available for incorporation. While the majority of samples we have processed in preliminary studies have provided more than enough cells for the proposed PTOs, it is possible we may still find achieving the target cell density of 20 million cells/mL to be challenging for some biopsies. If so, we will first reduce overall dimensions of the microfluidic chambers to minimize the volume of cell-containing precursor that must first be introduced and explore approaches to reduce the cell culture construct dimensions further, while increasing overall PTO surface area. Specifically, we can use a combination of precise photomasks (chrome on quartz) and thinner glass slides to reduce optical effects that limit resolution. In these ways, we anticipate achieving sub-100 μm constructs. We can also expand to low passage numbers, thereby increasing cell availability while hoping to minimize genetic drift.

Demonstration of utility of educated and activated T cells to be employed as a cell therapy against PTOs. Node-derived cells will be transferred from "activation" microfluidic devices to TOC devices not employed in activation experiments to test adaptive immunity and cell killing via cell therapy. It is contemplated that PTOs previously not exposed to immune cell perfusion can be successfully treated using immune cell populations activated by perfusion through matched PTO TOC arrays.

Figure 11A:
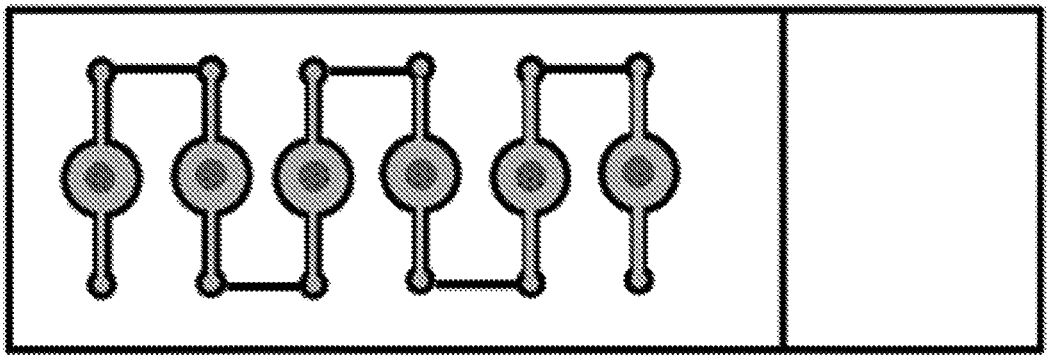
FIGS. 11A-11D are schematic illustrations of a tumor-on-a-chip (TOC) device that may be used for infusion of T cells and priming of their activated state according to embodiments of the present invention.
Figure 11B:
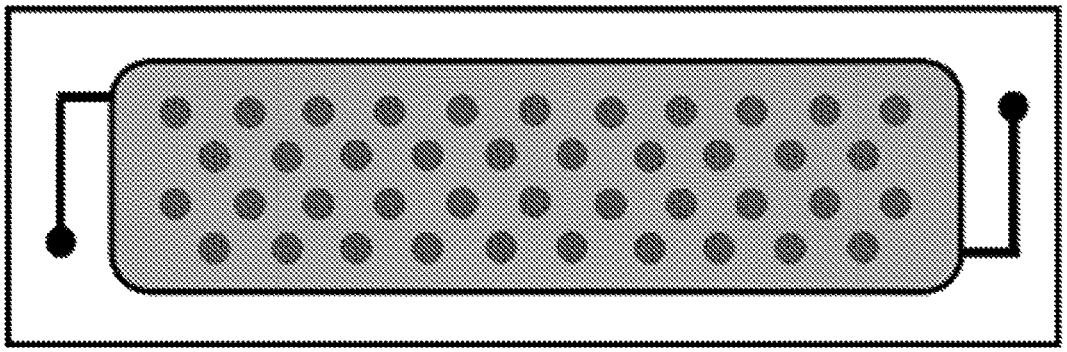
Figure 11C:
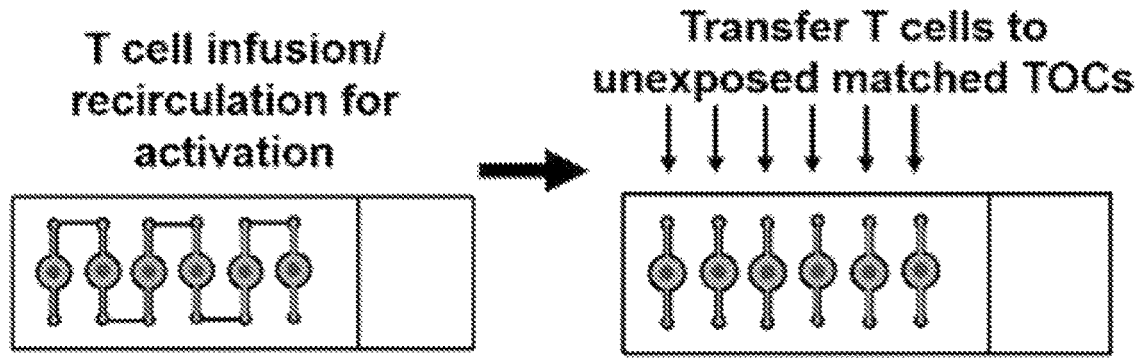

Immune cell transfer. When T cell activation is verified, the immune cell suspension being circulated for priming will be pumped into a clean fluid reservoir and transferred to fresh PTO TOCs from the same patient biospecimen that had been under maintenance with no drugs or immune cell exposure (FIG. 11C). These immune cell populations will be infused through the TOCs at 10 μL/min to allow for engraftment upon recognition of PTOs.

Homing assessment. Prior to infusion into TOCs, immune cell populations will be fluorescently labeled using membrane dyes (DiI/DiO, ThermoFisher). Daily fluorescent imaging will track motility and relative locations of the DiI/DiO-tagged cells in relation to PTOs, as well as engraftment and invasion into PTOs. We have previously demonstrated the efficacy of such tracking methods in the context of organoids in our metastasis-on-a-chip platform, which utilized a similar method to quantify metastasis of metastatic colorectal cancer cell lines through a microfluidic platform from gut to downstream liver organoids.

Assessment of therapeutic efficacy. Tumor cell killing and nearest neighbor quantification will be performed. Constant or intermittent flow will be used to support each organoid for 3, 7, or 10 days, and aliquots of media will be collected daily for ELISA analysis of perforin and granzyme B, secreted markers indicating T cell activation, as well as IL-2, a T-cell growth and differentiation factor, and ATP activity. On days 3, 7, and 10, constructs will be LIVE/DEAD stained and examined with confocal microscopy and image segmentation to determine total cell viability. Directly following this, samples will be photobleached to remove LIVE/DEAD fluorescence and then sequentially labeled and imaged with fluorescent antibodies using multispectral imaging to determine relative locations of melanoma cells and distinct immune cell subtypes. We can explore further use of checkpoint inhibitors to further prime the PTOs for cell therapy, which prelim data shows is feasible.

We will compare the efficacy of immune checkpoint inhibitors between low- and high-PD-L1 and CD80/86 expressing cohorts of PTOs. Literature values for high PD-L1 and CD80/86 expression in melanoma vary, but typically suggest prevalence around from 30—60%, depending on melanoma subtype. Experiments will be performed in triplicate or greater; data will be presented as mean±standard error of the mean. Students t-tests will be employed for 2-group comparisons with $\alpha=0.05$. One-way ANOVA will be employed for multiple comparisons with confidence limits of 95% considered significant.

Example 7—Engineering a Combined Lymph Node/Tumor Organoid from the Same Patient for Personalized Immunotherapy Screening A combined lymph node/melanoma organoid was prepared with cells from the same patient to thereby create a mixed tumor/node organoid, and experiments were performed to evaluate if the patient tumor, stroma and immune system remain viable for personalized immunotherapy screening. The mixed organoid allowed for individual patient tumor and stroma and immune system to remain viable for personalized immunotherapy screening and allowed for the creation of adaptive immunity through training of the patient's peripheral blood T cells to recognize tumor antigens that are exhibited on the surface of the APCs incorporated in the patient's own lymph node/tumor symbiotic organoids.

Methods: Surgically obtained matched melanoma and lymph node biospecimens from the same patient were transferred to the laboratory, washed with saline, antibiotic, and red blood cell lysis buffer. Biospecimens were dissociated, and incorporated into an ECM-based hydrogel system and biofabricated into 3D patient-specific mixed melanoma/node organoids. Cells were not sorted for tumor, as to preserve tumor heterogeneity, including stroma and immune cell components. Organoid sets were screened in parallel with nivolumab, pembrolizumab, ipilimumab, and dafrafenib/trametinib for 72 hours. Quantification of live/dead staining and metabolism assays, recorded relative drug efficacy in killing melanoma cells for a particular patient. Light microscopy, IHC and next generation sequencing (NGS) were used to compare tumor melanoma cells with organoid melanoma cells.

Results: Biospecimens from 5 stage III and IV melanoma patients were applied for mixed organoid development. Successful establishment rate (i.e., take rate) of viable organoid sets was 80% (4/5). Average time from organoid development to initiation of immunotherapy testing was 7 days. Organoid response to immunotherapy was similar to patient clinical response in ¾ patients. The fourth patient's organoids exhibited a 50% melanoma killing by nivolumab while the patient clinically progressed on the drug. Response to trametinib for a BRAF wild patient with melanoma harboring a MEK pathway was suggested by organoid testing prior to NGS and verified by clinical response upon treatment.

Conclusion: Development of 3D mixed immune-enhanced tumor/node organoids is a feasible platform, allowing individual patient immune system and tumor cells to remain viable for studying of personalized immunotherapy response and creation of adaptive immunity.

Figure 14A:
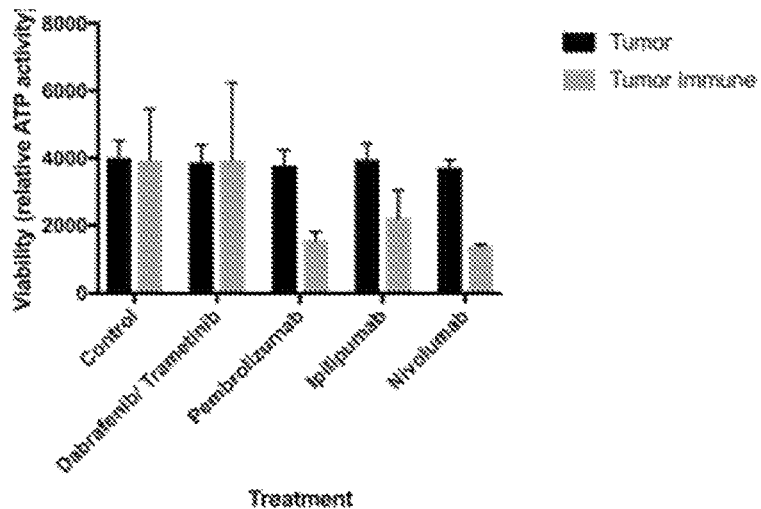
FIGS. 14A-14C are graphs showing the viability of tumor organoids (i.e., including tumor cells only) and tumor/immune organoids (i.e., including tumor cells and lymph node cells). Each of the sets of organoids were prepared with cells obtained from one melanoma patient with FIGS. 14A, 14B, and 14C showing the individualized results for each of three different melanoma patients. The results show that the tumor immune organoids, which were immune enhanced using lymph node cells, were capable of showing tumor cell killing under immune checkpoint inhibitor treatment, whereas the tumor organoids without immune enhancement do not respond.
Figure 14B:
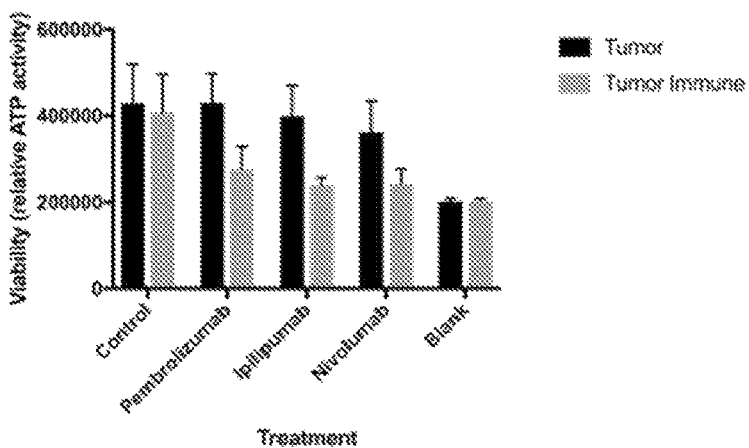
Figure 14C:
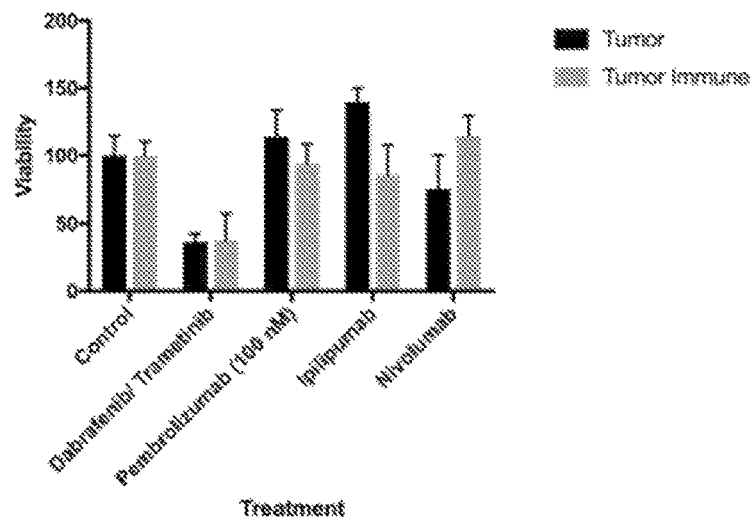
Figure 15B:
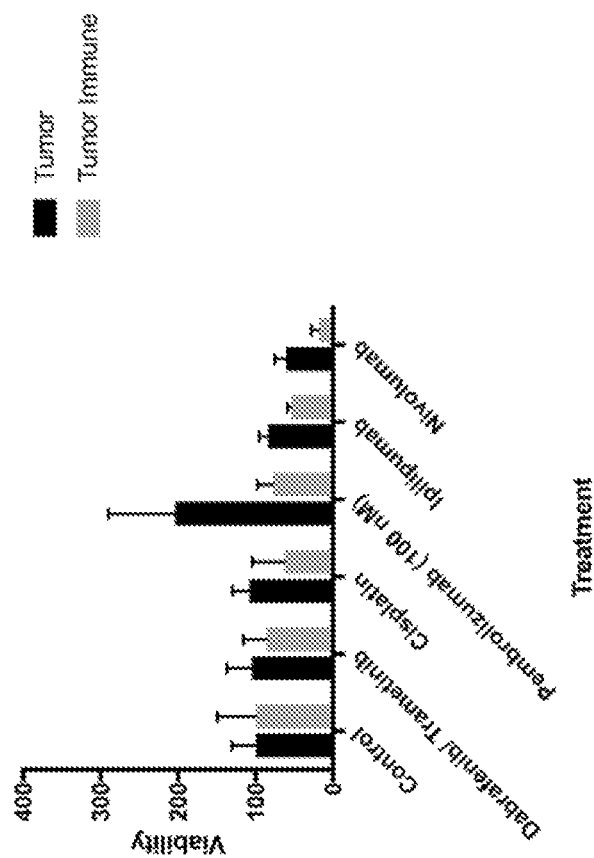
FIGS. 15A and 15B are graphs showing the viability of tumor organoids (i.e., including tumor cells only) and tumor/immune organoids (i.e., including tumor cells and immune cells from a white blood cell fraction of a patient blood draw). Each of the sets of organoids were prepared with cells obtained from one melanoma patient with FIGS. 15A and 15B showing the individualized results for each of two different melanoma patients. The results show that the tumor immune organoids, which were immune enhanced using cells from the white blood cell fraction of a blood draw, were capable of showing a tumor cell killing under immune checkpoint inhibitor treatment, whereas the tumor organoids without immune enhancement do not respond.
Figure 15A:
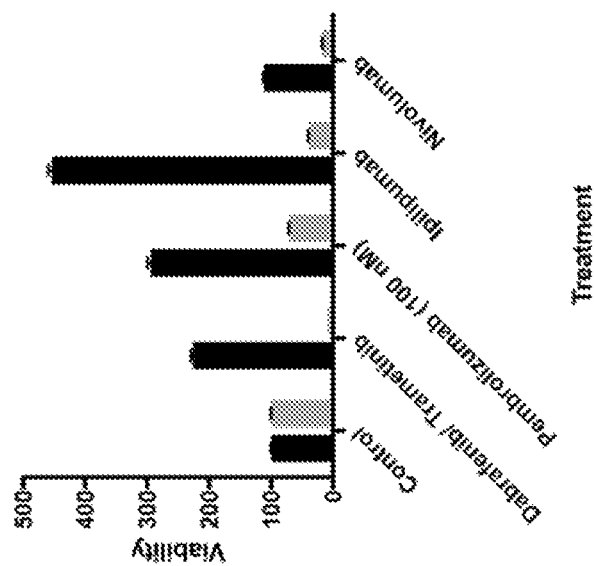

Melanoma patient tumor organoids immune enhanced with lymph node cells were prepared and subsequently tested with test compounds such as immune checkpoint inhibitors. Organoids without immune enhancement (tumor only organoids) did not respond, whereas tumor immune organoids did respond (FIGS. 14A-14C). In addition, melanoma patient tumor organoids immune enhanced with immune cells from the white blood cell fraction of a blood draw for a respective patient were prepared and subsequently tested with test compounds such as immune checkpoint inhibitors. Organoids without immune enhancement (tumor only organoids) did not respond, whereas tumor immune organoids did respond (FIGS. 15A-15B). Organoids were prepared as described in the Examples above, using hydrogels including thiolated HA, thiolated gelatin, and PEGDA crosslinker or thiolated HA and methacrylated collagen.

Example 8

Figure 16A:
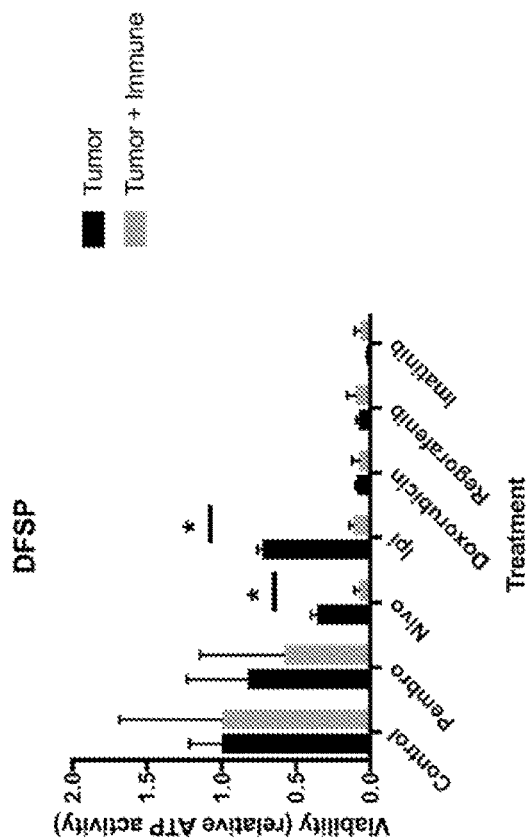
FIGS. 16A and 16B are graphs showing the viability of tumor organoids (i.e., including tumor cells only) and tumor/immune organoids (i.e., including tumor cells and immune cells from a white blood cell fraction of a patient blood draw). The organoids of FIG. 16A were prepared with cells obtained from one angiosarcoma patient. The organoids of FIG. 16B were prepared with cells obtains from one DFSP patient. The results show that the tumor immune organoids, which were immune enhanced using cells from the white blood cell fraction of a blood draw, were capable of showing a tumor cell killing under immune checkpoint inhibitor treatment, whereas the tumor organoids without immune enhancement do not respond.
Figure 16B:
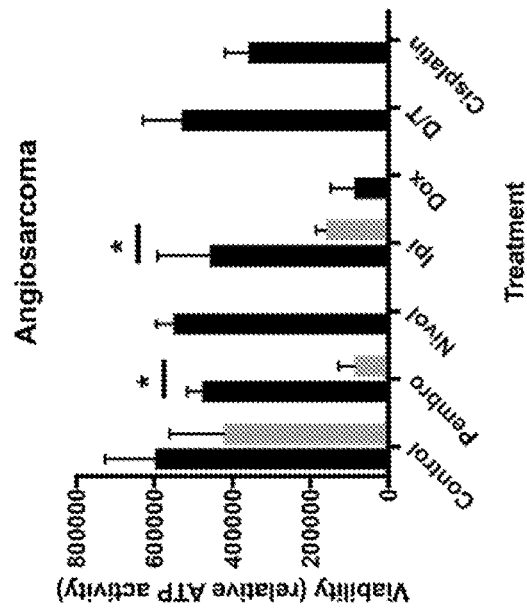

Sarcoma patient tumor organoids immune enhanced with immune cells from the white blood cell fraction of a blood draw for a respective patient were prepared from an angiosarcoma patient (FIG. 16A) and a dermatofibrosarcoma protuberans (DFSP) patient (FIG. 16B), and subsequently tested with test compounds such as immune checkpoint inhibitors. Organoids without immune enhancement (tumor only organoids) did not respond, whereas tumor immune organoids did respond. Organoids were prepared as described in the Examples above, using hydrogels including thiolated HA, thiolated gelatin, and PEGDA crosslinker or thiolated HA and methacrylated collagen.

Example 9

Figure 11D:
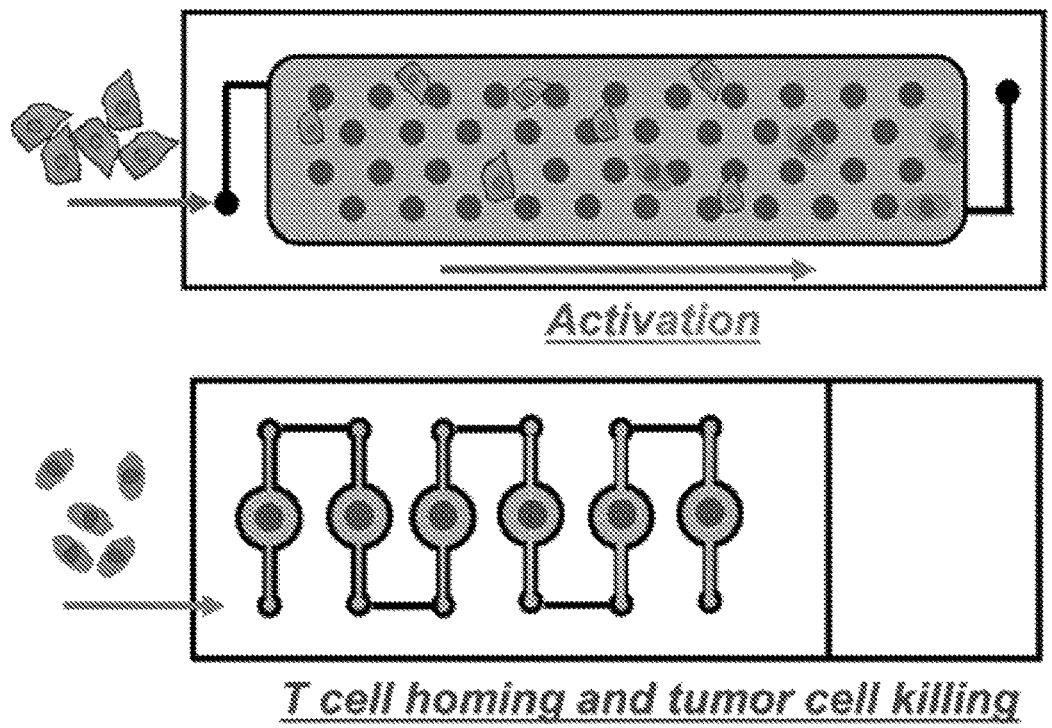
Figure 11E:
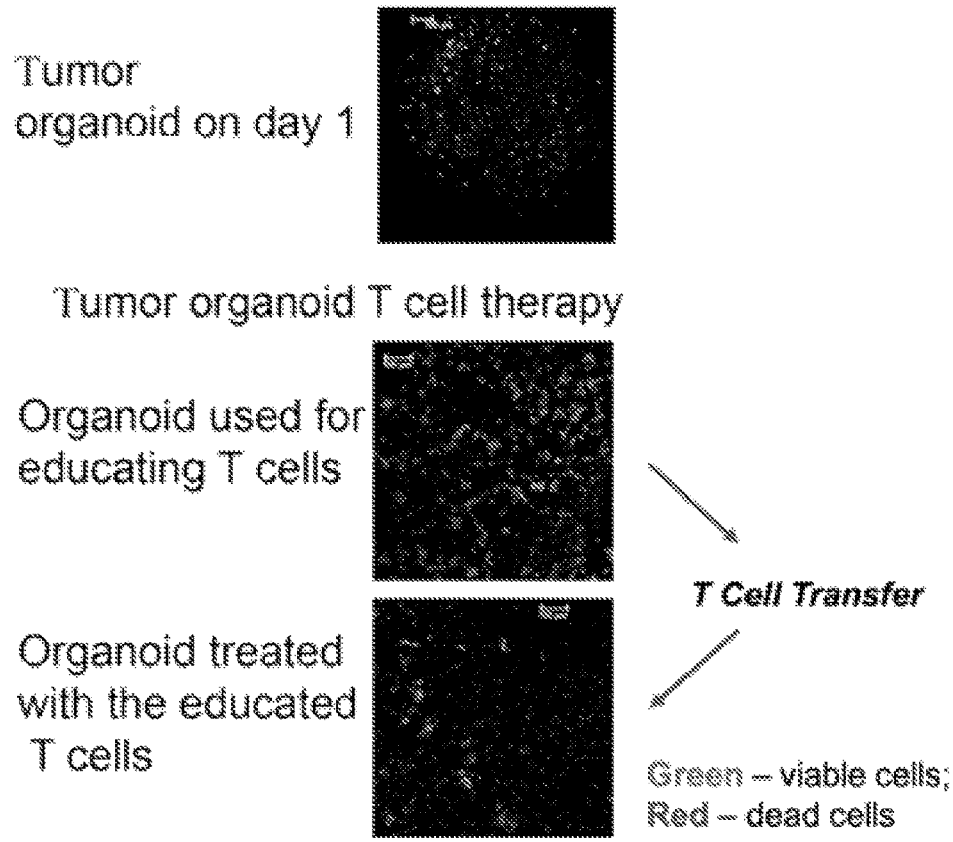
FIG. 11E shows LIVE/DEAD staining of PTOs at different stages of the process illustrated in FIG. 11D. Staining is shown prior to therapy (top image), following priming (middle image), and after transfer to previously untouched PTOs where they induce tumor cell killing (bottom image).

A patient's own peripheral T cells were provided in circulation with medium exposed to a tumor immune organoid for 7 days (FIG. 11D). These exposed T cells were collected and then transferred to tumor organoids from the same patient tumor biospecimen, which were not formed with immune cells from the patient or previously exposed to the T cells, and T cell mediated killing of the tumor was observed, indicated by visual staining of viable versus dead cells (FIG. 11E). Organoids were prepared as described in the Examples above, using hydrogels including thiolated HA, thiolated gelatin, and PEGDA crosslinker or thiolated HA and methacrylated collagen.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A method of activating an immune cell ex vivo, the method comprising:
    circulating a first immune cell through a chamber comprising a live tumor cell organoid to activate the first immune cell and provide an activated immune cell, wherein the live tumor cell organoid comprises a plurality of live tumor cells, a plurality of second immune cells, and wherein the first immune cell and the plurality of second immune cells are different;
    isolating the activated immune cell from the live tumor cell organoid to provide an isolated activated immune cell; and
    propagating the isolated activated immune cell to provide a population of activated immune cells.

2. The method of claim 1, wherein the plurality of live tumor cells are collected and/or derived from a tumor in a subject.

3. The method of claim 1, wherein the plurality of live tumor cells and the first immune cell are collected and/or derived from the same subject.

4. The method of claim 1, wherein the first immune cell is collected and/or derived from peripheral blood of a subject.

5. The method of claim 1, wherein the live tumor cell organoid further comprises a hydrogel and the plurality of live tumor cells are encapsulated by the hydrogel.

6. The method of claim 1, wherein the first immune cell is a follicular dendritic lymph cell, fibroblastic reticular lymph cell, leukocyte, B cell, T cell, a myeloid cell, or a lymphoid in origin cell.

7. The method of claim 1, wherein the first immune cell is a T cell.

8. The method of claim 1, wherein the first immune cell is a B cell.

9. The method of claim 1, wherein the plurality of live tumor cells comprises malignant cells.

10. The method of claim 1, wherein the plurality of live tumor cells and the first immune cell are mammalian cells.

11. The method of claim 1, wherein the plurality of live tumor cells and/or the first immune cell comprise a detectable compound.

12. The method of claim 1, wherein the live tumor cell organoid has a total number of cells in a range from about 1 million to about 100 million cells.

13. The method of claim 1, further comprising administering the population of activated immune cells to a patient.

14. The method of claim 1, wherein the plurality of second immune cells are antigen presenting cells, and the live tumor cell organoid further comprises a hydrogel, and wherein the plurality of live tumor cells and the plurality of second immune cells are intermixed and are encapsulated by the hydrogel.

15. The method of claim 1, wherein the plurality of second immune cells are antigen presenting cells and the plurality of second immune cells and the plurality of live tumor cells are intermixed in the live tumor cell organoid.

16. The method of claim 15, wherein the plurality of second immune cells are collected and/or derived from a lymph node in a subject.

17. The method of claim 15, wherein the plurality of second immune cells are collected and/or derived from bone marrow of a subject.

18. The method of claim 15, wherein the plurality of second immune cells are collected and/or derived from an organ of a subject.

19. The method of claim 15, wherein the plurality of second immune cells are follicular dendritic lymph cells, fibroblastic reticular lymph cells, leukocytes, B cells, T cells, myeloid cells, or lymphoid in origin cells.

20. The method of claim 15, wherein the plurality of live tumor cells and the plurality of second immune cells are present in the live tumor cell organoid in a ratio of about 1:1 to about 100:1 (live tumor cells: second immune cells).

* * * * *

UNITED STATES PATENT AND TRADEMARK OFFICE
CERTIFICATE OF CORRECTION

| | | |
|---|---|---|
| PATENT NO. | : 12,038,432 B2 | Page 1 of 1 |
| APPLICATION NO. | : 16/966406 | |
| DATED | : July 16, 2024 | |
| INVENTOR(S) | : Skardal et al. | |

It is certified that error appears in the above-identified patent and that said Letters Patent is hereby corrected as shown below:

On the Title Page

Item (56) References Cited, OTHER PUBLICATIONS, Page 6, 2nd Column, 4th citation: Please correct "(dated Apr. 1, 12, 2022)" to read --(dated April 12, 2022)--

In the Specification

Column 5, Line 59: Please correct "teal's)" to read --terms)--

Column 6, Line 33: Please correct "even±0.1%" to read --even ± 0.1%--

Column 6, Line 36: Please correct "even±0.1%" to read --even ± 0.1%--

Column 8, Line 13: Please correct "has" to read --have--

Column 9, Line 32: Please correct "A G," to read --AG,--

Column 30, Line 57: Please correct "mean±standard)" to read --mean ± standard)--

Column 30, Line 58: Please correct "$\alpha$=0.05." to read --$\alpha$ = 0.05.--

Column 38, Line 12: Please correct "mean±standard" to read --mean ± standard--

Column 38, Line 13: Please correct "$\alpha$=0.05." to read --$\alpha$ = 0.05.--

Signed and Sealed this
Twentieth Day of May, 2025

Coke Morgan Stewart
*Acting Director of the United States Patent and Trademark Office*